US010973894B2

(12) United States Patent
Tran et al.

(10) Patent No.: US 10,973,894 B2
(45) Date of Patent: *Apr. 13, 2021

(54) METHODS OF ISOLATING T CELLS HAVING ANTIGENIC SPECIFICITY FOR A CANCER-SPECIFIC MUTATION

(71) Applicant: The United States of America, as represented by the Secretary, Department of Health and Human Services, Bethesda, MD (US)

(72) Inventors: Eric Tran, North Bethesda, MD (US); Yong-Chen Lu, Rockville, MD (US); Paul Robbins, Chevy Chase, MD (US); Steven A. Rosenberg, Potomac, MD (US)

(73) Assignee: The United States of America, as represented by the Secretary, Department of Health and Human, Bethesda, MD (US)

( * ) Notice: Subject to any disclaimer, the term of this patent is extended or adjusted under 35 U.S.C. 154(b) by 278 days.

This patent is subject to a terminal disclaimer.

(21) Appl. No.: 15/515,055

(22) PCT Filed: Oct. 2, 2014

(86) PCT No.: PCT/US2014/058805
§ 371 (c)(1),
(2) Date: Mar. 28, 2017

(87) PCT Pub. No.: WO2016/053339
PCT Pub. Date: Apr. 7, 2016

(65) Prior Publication Data
US 2017/0224800 A1 Aug. 10, 2017

(51) Int. Cl.
*A61K 39/00* (2006.01)
*C12N 5/0783* (2010.01)
*C12Q 1/6886* (2018.01)

(52) U.S. Cl.
CPC ........ *A61K 39/0011* (2013.01); *C12N 5/0636* (2013.01); *C12Q 1/6886* (2013.01); *A61K 2039/5158* (2013.01); *C12Q 2600/156* (2013.01)

(58) Field of Classification Search
CPC ........ A61K 2039/5158; A61K 39/0011; C12N 5/0636; C07K 4/12; C07K 14/435; C12Q 1/6886; C12Q 2600/156
See application file for complete search history.

(56) References Cited

U.S. PATENT DOCUMENTS

| 8,034,334 B2 | 10/2011 | Dudley et al. |
| 8,383,099 B2 | 2/2013 | Dudley et al. |
| 2004/0101519 A1* | 5/2004 | June ............ C12N 5/0634 424/93.21 |
| 2010/0189728 A1 | 7/2010 | Schendel et al. |
| 2010/0310533 A1 | 12/2010 | Yee |
| 2011/0293637 A1 | 12/2011 | Hacohen et al. |
| 2012/0244133 A1 | 9/2012 | Rosenberg et al. |
| 2012/0269860 A1 | 10/2012 | Karlsson-Parra et al. |
| 2015/0203886 A1 | 7/2015 | Kishi et al. |
| 2015/0250864 A1 | 9/2015 | Wang-Johanning |
| 2017/0218042 A1 | 8/2017 | Tran et al. |
| 2017/0224800 A1 | 8/2017 | Tran et al. |

FOREIGN PATENT DOCUMENTS

| JP | 2012-213402 A | 11/2012 | |
| JP | 2013-507986 A | 3/2013 | |
| JP | 2014-023445 A | 2/2014 | |
| WO | WO-9740156 A1 * | 10/1997 | ............ C07K 14/82 |
| WO | WO 2012/129201 A1 | 9/2012 | |
| WO | WO 2012/159643 A1 | 11/2012 | |
| WO | WO 2012/159754 A2 | 11/2012 | |
| WO | WO 2013/039889 A1 | 3/2013 | |
| WO | WO 2013/088114 A1 | 6/2013 | |
| WO | WO 2014/012051 A1 | 1/2014 | |
| WO | WO 2014/043441 A1 | 3/2014 | |
| WO | WO 2014/133567 A1 | 4/2014 | |
| WO | WO 2014/133568 A1 | 9/2014 | |

OTHER PUBLICATIONS

Dudly et al, Journal of Immunotherapy, 2001, vol. 24, pp. 363-373 (Year: 2001)*
Huang et al (Journal of Immunology, 2004, vol. 172, pp. 6057-6064) (Year: 2004).*
Turcotte et al (Journal of Immunology, 2013, vol. 191, 9 pages) (Year: 2013).*
Dudley et al (Journal of Immunotherapy, 2003, vol. 26, pp. 332-342) (Year: 2003).*
Abate-Daga et al., "Transcriptomic Analysis of Human Melanoma Lesions Resected for TIL Production Reveals the Presence of B Cells in Association with T Lymphocytes," pp. S168-S169, *Molecular Therapy*, 22(1): S1-S305 (2014).
Castle et al., "Exploiting the Mutanome for Tumor Vaccination," *Cancer Research*, 72(5): 1081-91 (2012).
Dudley et al., "Adoptive Cell Therapy for Patients with Metastatic Melanoma: Evaluation of Intensive Myeloablative Chemoradiation Preparatibe Regimens," *Journal of Clinical Oncology*, 26: 5233-9 (2008).

(Continued)

*Primary Examiner* — Karen A. Canella
(74) *Attorney, Agent, or Firm* — Leydig, Voit & Mayer

(57) ABSTRACT

Disclosed are methods of isolating T cells having antigenic specificity for a mutated amino acid sequence encoded by a cancer-specific mutation, the method comprising: identifying one or more genes in the nucleic acid of a cancer cell of a patient, each gene containing a cancer-specific mutation that encodes a mutated amino acid sequence; inducing autologous APCs of the patient to present the mutated amino acid sequence; co-culturing autologous T cells of the patient with the autologous APCs that present the mutated amino acid sequence; and selecting the autologous T cells. Also disclosed are related methods of preparing a population of cells, populations of cells, pharmaceutical compositions, and methods of treating or preventing cancer.

15 Claims, 9 Drawing Sheets

Specification includes a Sequence Listing.

(56) References Cited

OTHER PUBLICATIONS

Dudley et al., "Generation of Tumor-Infiltrating Lymphocyte Cultures for Use in Adoptive Transfer Therapy for Melanoma Patients," *Journal of Immunotherapy*, 26(4): 332-342 (2003).
Fox, "New Immune Therapy Approach Tackles Woman's Rare Cancer," www.nbcnews.com, published May 8, 2014.
Grady, "Patient's Cells Deployed to Attack Aggressive Cancer," *The New York Times*, published May 8, 2014.
Gros et al., "PD-1 identifies the patient-specific $CD8^+$ tumor-reactive repertoire infiltrating human tumors," *The Journal of Clinical Investigation*, 124(5): 2246-59 (Mar. 25, 2014).
Hoof et al., "NetMHCpan, a method for MHC class I binding prediction beyond humans," *Immunogenetics*, 61(1): 1-13 (2009).
International Bureau, International Search Report in International Application No. PCT/US2014/058805, dated Jan. 21, 2015.
International Bureau, Written Opinion in International Application No. PCT/US2014/058805, dated Jan. 21, 2015.
Jin et al., "Simplified Methods of the Growth of Human Tumor Infiltrating Lymphocytes in Gas-permeable Flasks to Numbers Needed for Patient Treatment," *Journal of Immunotherapy*, 35(3): 283-292 (2012).
Jones et al., "Frequent Mutations of Chromatin Remodeling Gene ARID1A in Ovarian Clear Cell Carcinoma," *Science*, 330(6001): 228-231(2010).
Linnemann et al., "High-throughput identification of antigen-specific TCRs by TCR gene capture," *Nature Medicine*, 19(11): 1534-1541 (Oct. 13, 2013).
Lu et al., "Efficient Identification of Mutated Cancer Antigens Recognized by T Cells Associated with Durable Tumor Regressions," *Clinical Cancer Research*, 20(13): 3401-10 (Jul. 1, 2014).
NCI Press Release, "NIH Study demonstrates that a new cancer immunotherapy method could be effective against a wide range of cancers," www.cancer.gov/newscenter/newsfromnci/2014/ACTepithelial, published May 8, 2014.
Riddell et al., "Restoration of Viral Immunity in Immunodeficient Humans by the Adoptive Transfer of T Cell Clones," *Science*, 257:238-41 (1992).
Riddell et al., "The use of anti-CD3 and anti-CD28 monoclonal antibodies to clone and expand human antigen-specific T cells," *Journal of Immunological Methods*, 128: 189-201 (1990).
Robbins et al., "Mining Exomic Sequencing Data to Indentify Mutated Anitgens Recognized by Adoptively Transferred Tumor-reactive T cells," *Nature Medicine*, 19(6): 747-752 (May 5, 2013).
Robbins et al., "Tumor Regression in Patients with Metastic Synovial Cell Sarcoma and Melanoma Using Genetically Engineered Lymphocytes Reactive with NY-ESO-1," *Journal of Clinical Oncology*, 29: 917-924 (2011).
Ronaghi et al., "A Sequencing Method Based on Real-Time Pyrophosphate," *Science*, 281(5375): 363-365 (1998).
Rosenberg, "The Curative Potential of T Cell Immunotherapy for Cancer," *Plenary Talk given at the American Association for Cancer Research*, presented on Apr. 7, 2014.
Tran et al., "Cancer Immunotherapy Based on Mutation-Specific CD4+ T Cells in a Patient with Epithelial Cancer," *Science*, 344: 641-645 (May 9, 2014).
Tran et al., "Supplementary Materials for Cancer Immunotherapy Based on Mutation-Specific CD4+ T Cells in a Patient with Epithelial Cancer," *Science*, 344: 641-645, (May 8, 2014—corrected May 30, 2014).
Tran et al., "T-cell therapy against cancer mutations," *Oncotarget*, 5(13): 4579-4580 (Jul. 19, 2014).
Turcotte et al., "Tumor-Reactive $CD8^+$ T Cells in Metastatic Gastrointestinal Cancer Refractory to Chemotherapy," *Clinical Cancer Research*, 20(2): 331-43 (Nov. 11, 2013).
Voelkerding et al., "Next-Generation Sequencing: From Basic Research to Diagnostics," *Clinical Chemistry*, 55(4): 641-658 (2009).

Winslow, "Patient's Immune System Harnessed to Attack Cancer," *The Wall Street Journal*, published May 8, 2014.
Zhang et al., "The impact of next-generation sequencing on genomics," *Journal of Genetics and Genomics*, 38(3): 95-109 (2011).
Tran et al., "T-Cell Transfer Therapy Targeting Mutant KRAS in Cancer," *New Engl. J. Med.*, 375(23): 2255-2262 (2016).
Zacharakis et al., "Immune recognition of somatic mutations leading to complete durable regression in metastatic breast cancer," *Nat. Med.*, 24: 724-730 (2018).
Japanese Patent Office, Notice of Reasons for Refusal in counterpart Japanese Application No. 517677/2017, dated Jul. 31, 2018.
Restifo et al., "Adoptive immunotherapy for cancer: harnessing the T cell response," *Nat. Rev. Immunol.*, 12(4): 269-281 (2012).
Robbins, "Use of High Throughput Sequencing Methods to Identify Cancer Immunotherapy Targets," *Annual Meeting of the Japanese Society for Immunology*, 42: 12 (S7-2) (2013).
International Bureau, International Search Report in International Application No. PCT/US2014/058796, dated Jun. 10, 2015.
International Bureau, Written Opinion in International Application No. PCT/US2014/058796, dated Jun. 10, 2015.
An et al., "Multivalent Minigene Vaccine, Containing B-Cell, Cytotoxic T-Lymphocyte, and $T_h$ Epitopes from Several Microbes, Induces Appropriate Responses In Vivo and Confers Protection against More than One Pathogen," *J. Virology*, 71(3): 2292-2302 (1997).
"Article Metrics—Immune recognition of somatic mutations leading to complete durable regression in metastatic brain cancer," accessed online at <nature.com/articles/s41591-018-0040-8/metrics>, on Oct. 18, 2019.
"Article Metrics—T-Cell Transfer Therapy Targeting Mutant KRAS in Cancer," accessed online at <nejm.org/doi/metrics/10.1056/NEJMoa1609279#media_coverage>, on Oct. 18, 2019.
"Cancer Immunotherapy Based on Mutation-Specific CD+ T Cells in a Patient with Epithelial Cancer—Overview of attention for article published in Science, May 2014," accessed online at <altmetric.com/details/2336865>, on Oct. 18, 2019.
Grady, D., "1 Patient, 7 Tumors and 100 Billion Cells Equal 1 Striking Recovery," *The New York Times*, accessed online at <nytimes.com/2016/12/07/health/cancer-immunotherapy.html>, on Oct. 21, 2019, published on Dec. 7, 2016.
Japanese Patent Office, Notice of Reasons for Refusal in counterpart Japanese Application No. 517662/2017, dated Aug. 14, 2018.
Kobayashi et al., "A new cloning and expression system yields and validates TCRs from blood lymphocytes of patients with cancer within 10 days," *Nat. Med.*, 19(11): 1542-1546 (2013).
Lu et al., "Mutated PPP1R3B is Recognized by T Cells Used to Treat a Melanoma Patient Who Experienced a Durable Complete Tumor Regression," *J. Immunology*, 190: 6034-6042 (2013).
"One Woman's Cancer Battle Highlights Promise of New Treatment," *U.S. News & World Report*, accessed online at <health.usnews.com/health-news/articles/2014/05/08/one-womans-cancer-battle-highlights-promise-of-new-treatment>, on Oct. 21, 2019, published May 8, 2014.
Radvanyi, L. G., Targeting the cancer mutanome of breast cancer, *Nat. Med.*, 24(6): 703-704 (2018).
Leifert et al., "Targeting plasmid-encoded proteins to the antigen presentation pathways," *Immunol. Rev.*, 199: 40-53 (2004).
Parkhurst et al., "Unique Neoantigens Arise from Somatic Mutations in Patients with Gastrointestinal Cancers," *Cancer Discov.*, 9(8): 1022-1035 (2019).
Tan et al., "Isolation of T cell receptor specifically reactive with autologous tumour cells from tumour-infiltrating lymphocytes and construction of T cell receptor engineered T cells for esophageal squamous cell carcinoma," *J. Immunother. Cancer*, 7(1): 232 (2019).
Tran et al., "Immunogenicity of somatic mutations in human gastrointestinal cancers," and Supplementary Materials, *Science*, 350(6266): 1387-1390 (2015).
U.S. Appl. No. 15/514,942, filed Mar. 28, 2017.

* cited by examiner

METHODS OF ISOLATING T CELLS HAVING ANTIGENIC SPECIFICITY FOR A CANCER-SPECIFIC MUTATION

STATEMENT REGARDING FEDERALLY SPONSORED RESEARCH AND DEVELOPMENT

This invention was made with Government support under project number ZIABC010984 by the National Institutes of Health, National Cancer Institute. The Government has certain rights in the invention.

CROSS-REFERENCE TO RELATED APPLICATION

This patent application is a U.S. national stage of PCT/US2014/058805, filed Oct. 2, 2014.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 29,615 29,568 Byte ASCII (Text) file named "728037_ST25.TXT" dated Mar. 22, 2017.

BACKGROUND OF THE INVENTION

Adoptive cell therapy (ACT) using tumor infiltrating lymphocytes (TIL) can produce positive clinical responses in some cancer patients. Nevertheless, obstacles to the successful use of ACT for the widespread treatment of cancer and other diseases remain. For example, T cells that specifically recognize cancer antigens may be difficult to identify and/or isolate from a patient. Accordingly, there is a need for improved methods of obtaining cancer-reactive T cells.

BRIEF SUMMARY OF THE INVENTION

An embodiment of the invention provides a method of isolating T cells having antigenic specificity for a mutated amino acid sequence encoded by a cancer-specific mutation, the method comprising: identifying one or more genes in the nucleic acid of a cancer cell of a patient, each gene containing a cancer-specific mutation that encodes a mutated amino acid sequence; inducing autologous antigen presenting cells (APCs) of the patient to present the mutated amino acid sequence; co-culturing autologous T cells of the patient with the autologous APCs that present the mutated amino acid sequence; and selecting the autologous T cells that (a) were co-cultured with the autologous APCs that present the mutated amino acid sequence and (b) have antigenic specificity for the mutated amino acid sequence presented in the context of a major histocompatability complex (MHC) molecule expressed by the patient to provide isolated T cells having antigenic specificity for the mutated amino acid sequence encoded by the cancer-specific mutation.

Another embodiment of the invention provides a method of preparing a population of T cells that have antigenic specificity for a mutated amino acid sequence encoded by a cancer-specific mutation, the method comprising: identifying one or more genes in the nucleic acid of a cancer cell of a patient, each gene containing a cancer-specific mutation that encodes a mutated amino acid sequence; inducing autologous APCs of the patient to present the mutated amino acid sequence; co-culturing autologous T cells of the patient with the autologous APCs that present the mutated amino acid sequence; selecting the autologous T cells that (a) were co-cultured with the autologous APCs that present the mutated amino acid sequence and (b) have antigenic specificity for the mutated amino acid sequence presented in the context of a MHC molecule expressed by the patient; and expanding the number of selected autologous T cells to obtain a population of T cells that have antigenic specificity for the mutated amino acid sequence encoded by the cancer-specific mutation.

Additional embodiments of the invention provide related populations of cells, pharmaceutical compositions, and methods of treating or preventing cancer.

BRIEF DESCRIPTION OF THE SEVERAL VIEWS OF THE DRAWING(S)

FIG. 1A is a graph showing the number of spots per $1\times10^3$ (1e3) cells measured by interferon (IFN)-$\gamma$ enzyme-linked immunosorbent spot (ELISPOT) assay after a 20 hour co-culture of 3737-TIL with OKT3 or dendritic cells (DCs) transfected with green fluorescent protein (GFP) RNA, or the indicated tandem mini-gene (TMG) construct. ">" denotes greater than 500 spots per $1\times10^3$ cells. Mock-transfected cells were treated with transfection reagent only without addition of nucleic acid.

FIG. 1B is a graph showing the percentage of CD4+3737-TIL that were OX40+ following co-culture with OKT3 or DCs transfected with GFP RNA, TMG-1, or the indicated wild type (wt) gene ALK, CD93, ERBB2IP, FCER1A, GRXCR1, KIF9, NAGS, NLRP2, or RAC3. Mock-transfected cells were treated with transfection reagent only without addition of nucleic acid.

FIGS. 2A-2C are graphs showing the number of spots per $1\times10^3$ (1e3) cells measured by IFN-$\gamma$ ELISPOT assay at 20 hours for 3737-TIL (A), DMFS T cells (B), or T4 T cells (C) that were co-cultured with DCs transfected with TMG-1 (A) or 624-CIITA cells (B) and (C) that had been pre-incubated with nothing, or the indicated HLA-blocking antibodies (against MHC-I, MHC-II, HLA-DP, HLA-DQ, or HLA-DR) (A-C).

FIG. 2D is a graph showing the number of spots per $1\times10^3$ (1e3) cells measured by IFN-$\gamma$ ELISPOT assay at 20 hours for 3737-TIL co-cultured with autologous DQ-0301/-0601 B cells (grey bars) or allogeneic EBV-B cells partially matched at the HLA-DQ 05/0601 locus (black bars) or the HLA-DQ-0201/0301 locus (unshaded bars) that had been pulsed overnight with DMSO, mutated (mut) ALK or mut ERBB2IP 25-AA long peptides. ETGHLENGNKYPNLE (SEQ ID NO: 53);

FIG. 2E is a graph showing the number of spots per $1\times10^3$ (1e3) cells measured by IFN-$\gamma$ ELISPOT assay at 20 hours for 3737-TIL co-cultured with autologous B cells that had been pulsed overnight with the mut ERBB2IP 25-AA peptide TSFLSINSKEETGHLENGNKYPNLE (SEQ ID NO: 73), or the indicated truncated mut ERBB2IP peptides FLSINSKEETGHLENGNKYPNLE (SEQ ID NO: 30), SINSKEETGHLENGNKYPNLE (SEQ ID NO: 31), NSKEETGHLENGNKYPNLE (SEQ ID NO: 32), KEETGHLENGNKYPNLE (SEQ ID NO: 33), ETGHLENGNKYPNLE (SEQ ID NO: 53), TSFLSINSKEETGHL (SEQ ID NO: 34), TSFLSINSKEETGHLEN (SEQ ID NO: 35), TSFLSINSKEETGHLENG (SEQ ID NO: 36), TSFLSINSKEETGHLENGNKY (SEQ ID NO: 37), or TSFLSINSKEETGHLENGNKYPN (SEQ ID NO: 38).

Figure 4:
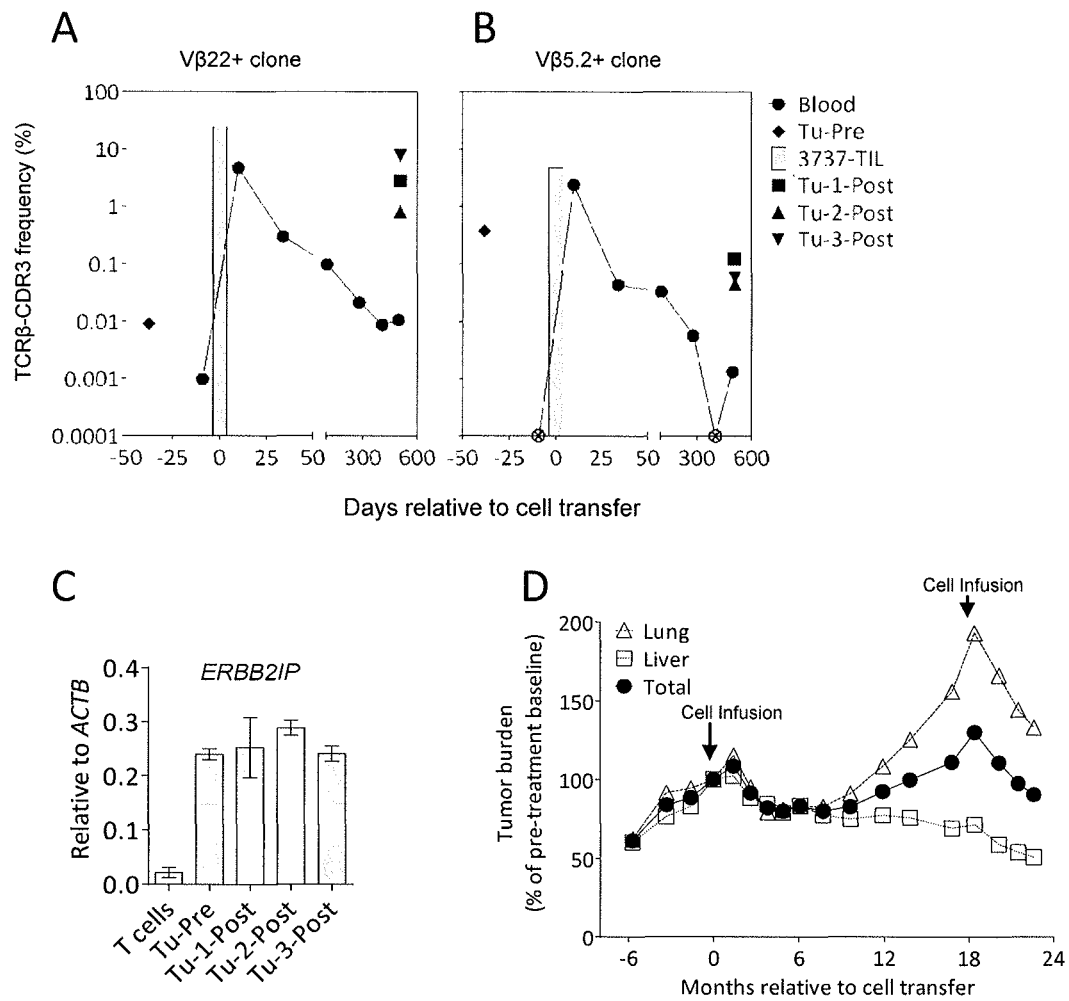

FIGS. 4A and 4B are graphs showing the frequency of the two ERBB2IP-mutation-specific TCRβ-CDR3 clonotypes Vβ22+(A) and Vβ5.2+(B) in the blood (circles) of patient 3737 at various times pre- and post-adoptive cell transfer with 3737-TIL, a tumor before cell transfer (diamonds), and various tumors after cell transfer (Tu-1-Post (squares), Tu-2-Post (▲), and Tu-3-Post (▼)). Shaded bars indicate the frequency of the two ERBB2IP-mutation-specific TCRβ-CDR3 clonotypes Vβ22+(A) and Vβ5.2+(B) in the transferred cells (3737-TIL). "X" indicates "Not detected."

FIG. 4C is a graph showing ERBB2IP expression relative to ACTB in 3737-TIL (T cells) and various tumors pre (Tu-Pre) and post (Tu-1-post, Tu-2-post, and Tu-3-post) adoptive cell transfer.

FIG. 4D is a graph showing the total tumor burden (circles) (measured as % of pre-treatment baseline) or tumor burden in the lung (triangles) or liver (squares) at the indicated number of months relative to cell transfer (indicated by arrows).

Figures 5A, 5B, 5C:
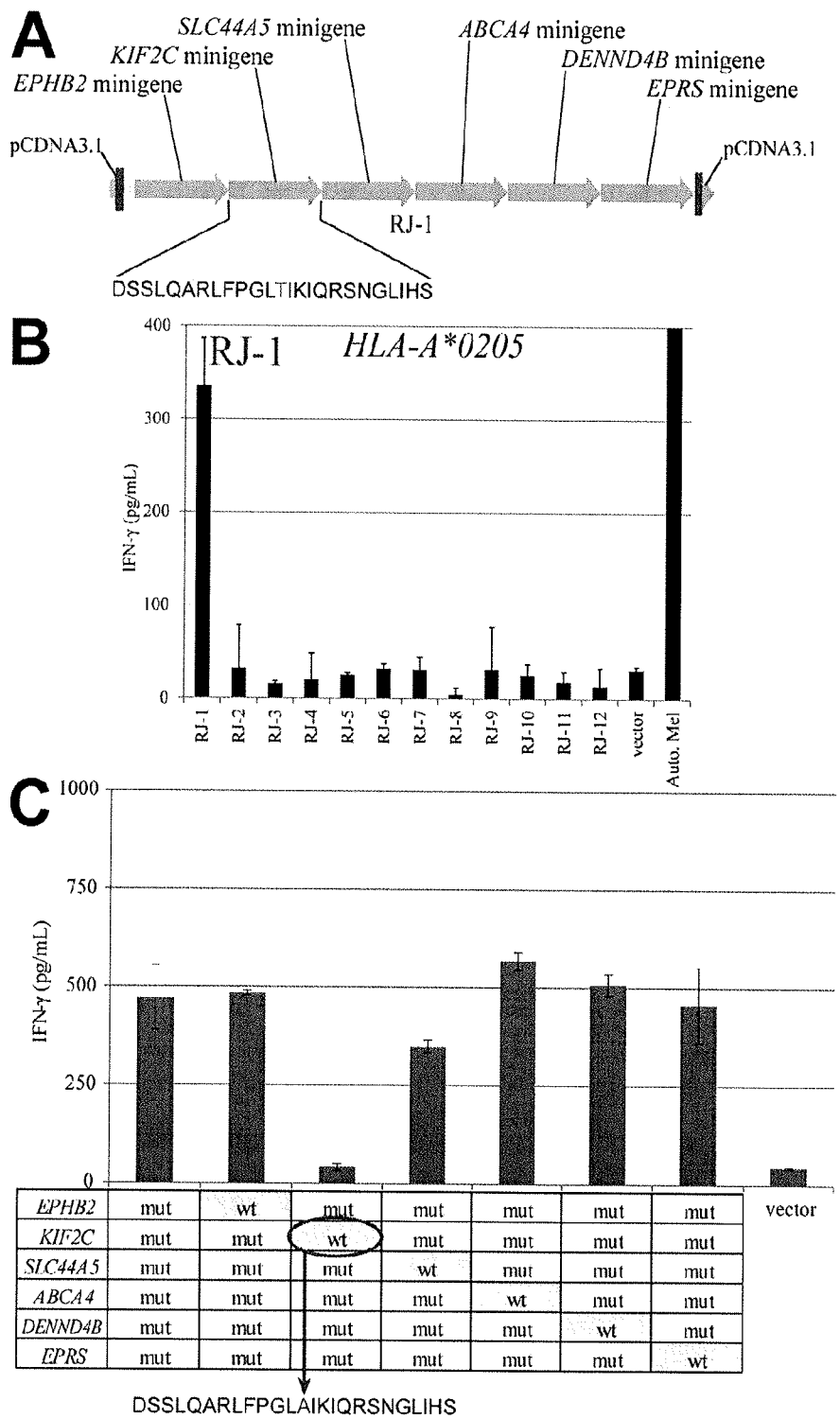

FIG. 5A is a schematic of an example of tandem minigene (TMG) construct, which encoded polypeptides containing 6 identified mutated amino acid residues flanked on their N- and C-termini, 12 amino acids on both sides. The mutated KIF2C sequence is DSSLQARLFPGLTIKIQRSNGLIHS (SEQ ID NO: 57).

FIG. 5B is a graph showing the level of IFN-γ (pg/mL) secreted by TIL 2359 T cells co-cultured overnight with autologous melanocytes or COS-7 cells co-transfected with HLA-A*0205 and TMG construct RJ-1 (structure shown in FIG. 9A), RJ-2, RJ-3, RJ-4, RJ-5, RJ-6, RJ-7, RJ-8, RJ-9, RJ-10, RJ-11, RJ-12, or an empty vector.

FIG. 5C is a graph showing the level of IFN-γ (pg/mL) secreted by TIL 2359 co-cultured with COS-7 cells transfected with HLA-A*0205 and an RJ-1 variant in which the gene indicated "wt" in the table was converted back to the WT sequence. The KIF2C WT sequence is DSSLQARLFPGLAIKIQRSNGLIHS (SEQ ID NO: 65).

Figure 5D:
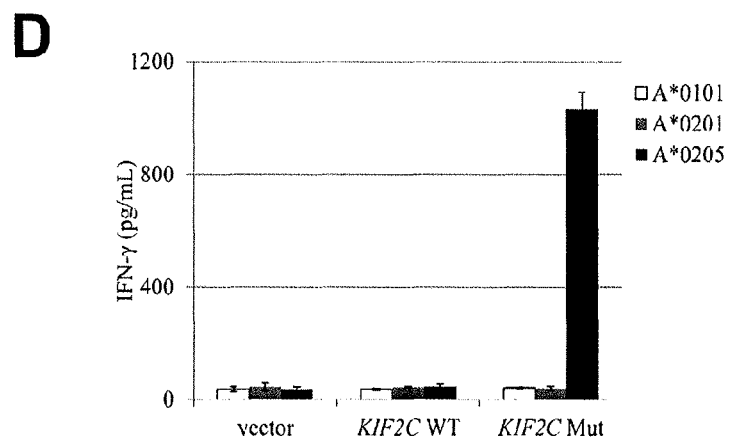

FIG. 5D is a graph showing the level of IFN-γ (pg/mL) secreted by TIL 2359 co-cultured with COS-7 cells transfected with an empty vector, KIF2C WT, or mutated KIF2C cDNA construct, together with HLA cDNA construct (identifying each shaded bar from left to right): HLA-A*0101 (unshaded bars), HLA-A*0201 (grey bars), or HLA-A*0205 (black bars).

Figure 5E:
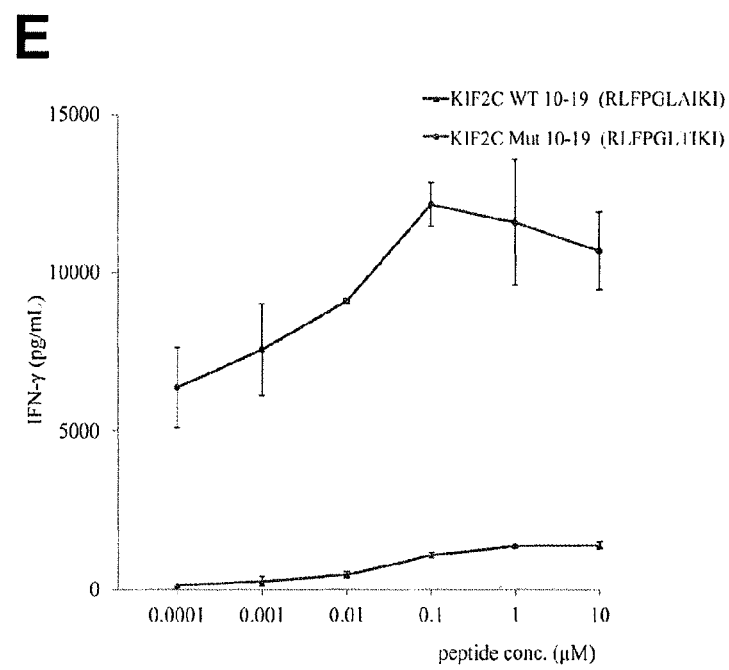

FIG. 5E is a graph showing the level of IFN-γ (pg/mL) secreted by TIL 2359 T cells co-cultured overnight with HEK293 cells stably expressing HLA-A*0205 that were pulsed with various concentrations (μM) of $KIF2C_{10-19}$ WT (RLFPGLAIKI; SEQ ID NO: 58) (bottom line in graph) or mutated $KIF2C_{10-19}$ (RLFPGLTIKI; SEQ ID NO: 59) (top line in graph).

Figures 6A, 6B, 6C:
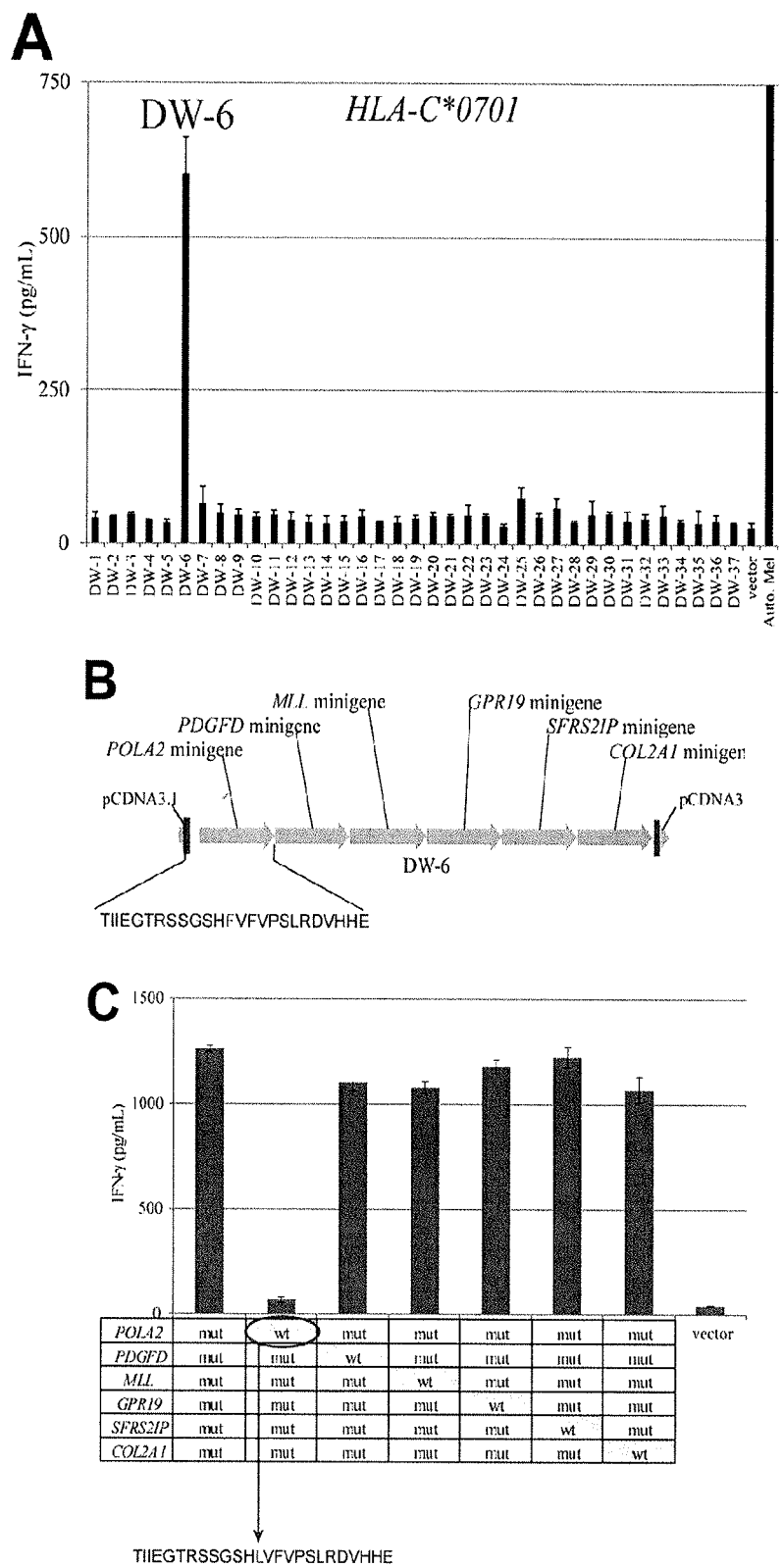

FIG. 6A is a graph showing the level of IFN-γ (pg/mL) secreted by TIL 2591 T cells co-cultured with autologous melanocytes or HEK293 cells stably expressing HLA-C*0701 transfected with an empty vector or a TMG construct selected from the group consisting of DW-1 to DW-37.

FIG. 6B is a schematic showing the structure of TMG construct DW-6. The mutated POLA2 sequence is TIIEGTRSSGSHFVFVPSLRDVHHE (SEQ ID NO: 64).

FIG. 6C is a graph showing the level of IFN-γ (pg/mL) secreted by TIL 2591 co-cultured with COS-7 cells transfected with HLA-C*0701 and a DW-6 variant in which the gene indicated "wt" in the table was converted back to the WT sequence. The POLA2 WT sequence is TIIEGTRSSGSHLVFVPSLRDVHHE (SEQ ID NO: 66).

Figures 6D, 6E:
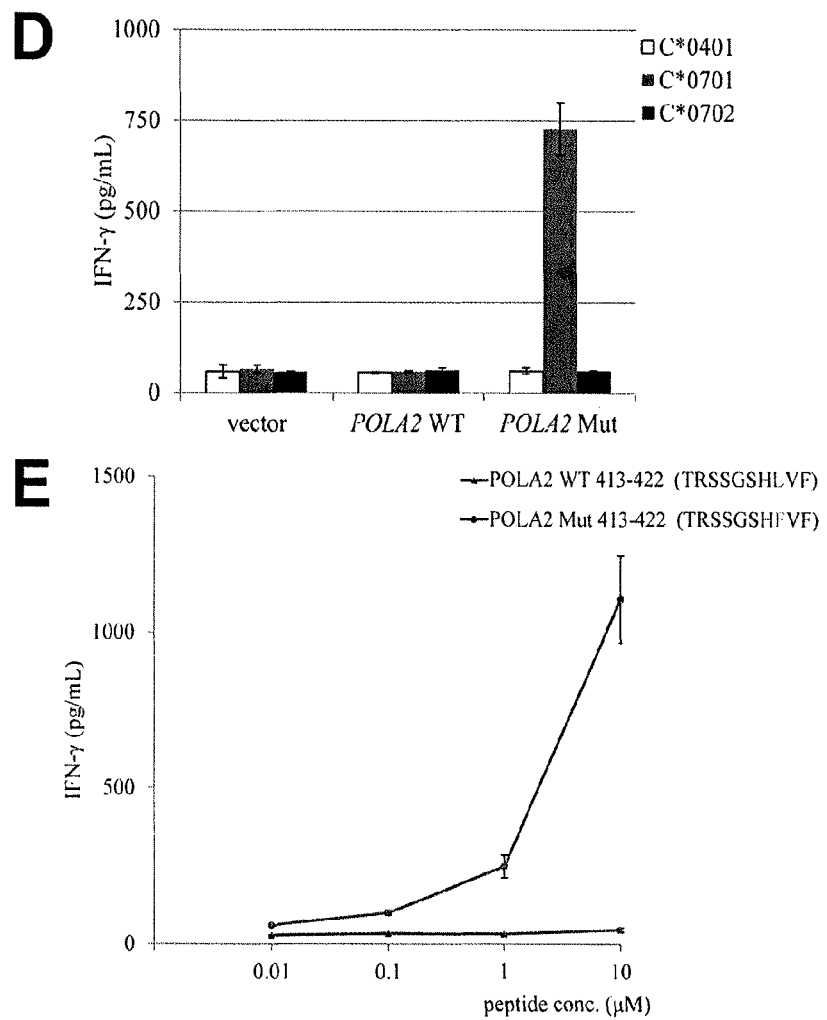

FIG. 6D is a graph showing the level of IFN-γ (pg/mL) secreted by TIL 2591 co-cultured with COS-7 cells transfected with an empty vector, POLA2 WT, or mutated POLA2 cDNA construct, together with HLA cDNA construct (identifying each bar from left to right): HLA-C*0401 (unshaded bars), HLA-C*0701 (grey bars), or HLA-C*0702 (black bars).

FIG. 6E is a graph showing the level of IFN-γ (pg/mL) secreted by TIL 2591 T cells co-cultured overnight with HEK293 cells stably expressing HLA-C*0701 that were pulsed with various concentrations (μM) of $POLA2_{413-422}$ WT (TRSSGSHLVF; SEQ ID NO: 67) (bottom line in graph) or mutated $POLA2_{413-422}$ (TRSSGSHFVF; SEQ ID NO: 68) (top line in graph).

FIGS. 7A-7F are computerized tomography (CT) scans of the lungs of Patient 3737 taken prior to (A-C) and six months after (D-F) the second administration of mutation-reactive cells. The arrows point to cancerous lesions.

DETAILED DESCRIPTION OF THE INVENTION

An embodiment of the invention provides a method of isolating T cells having antigenic specificity for a mutated amino acid sequence encoded by a cancer-specific mutation. The invention provides many advantages. For example, the inventive methods may rapidly assess a large number of mutations restricted by all of the patient's MHC molecules at one time, which may identify the full repertoire of the patient's mutation-reactive T cells. Additionally, by distinguishing immunogenic cancer mutations from (a) silent cancer-specific mutations (which do not encode a mutated amino acid sequence) and (b) cancer-specific mutations that encode a non-immunogenic amino acid sequence, the inventive methods may identify one or more cancer-specific, mutated amino acid sequences that may be targeted by a T cell. In addition, the invention may provide T cells having antigenic specificity for mutated amino acid sequences encoded by cancer-specific mutations that are unique to the patient, thereby providing an isolated, "personalized" population of T cells that may be useful for preparing cells for adoptive cell therapies, e.g., for treating or preventing the patient's cancer. The inventive methods may also avoid the technical biases inherent in traditional methods of identifying cancer antigens such as, for example, those using cDNA libraries, and may also be less time-consuming and laborious than those methods. For example, the inventive methods may select mutation-reactive T cells without co-culturing the T cells with tumor cell lines, which may be difficult to generate, particularly for e.g., epithelial cancers. Without being bound to a particular theory or mechanism, it is believed that the inventive methods may identify and isolate T cells that target the destruction of cancer cells while minimizing or eliminating the destruction of normal, noncancerous cells, thereby reducing or eliminating toxicity. Accordingly, the invention may also provide T cells that successfully treat or prevent cancer such as, for example, cancers that do not respond to other types of treatment such as, for example, chemotherapy alone, surgery, or radiation.

The method may comprise identifying one or more genes in the nucleic acid of a cancer cell of a patient, each gene containing a cancer-specific mutation that encodes a mutated amino acid sequence. The cancer cell may be obtained from any bodily sample derived from a patient which contains or is expected to contain tumor or cancer cells. The bodily sample may be any tissue sample such as blood, a tissue sample obtained from the primary tumor or from tumor metastases, or any other sample containing tumor or cancer cells. The nucleic acid of the cancer cell may be DNA or RNA.

In order to identify cancer-specific mutations, the method may further comprise sequencing nucleic acid such as DNA or RNA of normal, noncancerous cells and comparing the sequence of the cancer cell with the sequence of the normal, noncancerous cell. The normal, noncancerous cell may be obtained from the patient or a different individual.

The cancer-specific mutation may be any mutation in any gene which encodes a mutated amino acid sequence (also referred to as a "non-silent mutation") and which is expressed in a cancer cell but not in a normal, noncancerous cell. Non-limiting examples of cancer-specific mutations that may be identified in the inventive methods include missense, nonsense, insertion, deletion, duplication, frameshift, and repeat expansion mutations. In an embodiment of the invention, the method comprises identifying at least one gene containing a cancer-specific mutation which encodes a mutated amino acid sequence. However, the number of genes containing such a cancer-specific mutation that may be identified using the inventive methods is not limited and may include more than one gene (for example, about 2, about 3, about 4, about 5, about 10, about 11, about 12, about 13, about 14, about 15, about 20, about 25, about 30, about 40, about 50, about 60, about 70, about 80, about 90, about 100, about 150, about 200, about 400, about 600, about 800, about 1000, about 1500, about 2000 or more, or a range defined by any two of the foregoing values). Likewise, in an embodiment of the invention, the method comprises identifying at least one cancer-specific mutation which encodes a mutated amino acid sequence. However, the number of such cancer-specific mutations that may be identified using the inventive methods is not limited and may include more than one cancer-specific mutation (for example, about 2, about 3, about 4, about 5, about 10, about 11, about 12, about 13, about 14, about 15, about 20, about 25, about 30, about 40, about 50, about 60, about 70, about 80, about 90, about 100, about 150, about 200, about 400, about 600, about 800, about 1000, about 1500, about 2000 or more, or a range defined by any two of the foregoing values). In an embodiment in which more than one cancer-specific mutation is identified, the cancer-specific mutations may be located in the same gene or in different genes.

In an embodiment, identifying one or more genes in the nucleic acid of a cancer cell comprises sequencing the whole exome, the whole genome, or the whole transcriptome of the cancer cell. Sequencing may be carried out in any suitable manner known in the art. Examples of sequencing techniques that may be useful in the inventive methods include Next Generation Sequencing (NGS) (also referred to as "massively parallel sequencing technology") or Third Generation Sequencing. NGS refers to non-Sanger-based high-throughput DNA sequencing technologies. With NGS, millions or billions of DNA strands may be sequenced in parallel, yielding substantially more throughput and minimizing the need for the fragment-cloning methods that are often used in Sanger sequencing of genomes. In NGS, nucleic acid templates may be randomly read in parallel along the entire genome by breaking the entire genome into small pieces. NGS may, advantageously, provide nucleic acid sequence information of a whole genome, exome, or transcriptome in very short time periods, e.g., within about 1 to about 2 weeks, preferably within about 1 to about 7 days, or most preferably, within less than about 24 hours. Multiple NGS platforms which are commercially available or which are described in the literature can be used in the context of the inventive methods, e.g., those described in Zhang et al., *J. Genet. Genomics,* 38(3): 95-109 (2011) and Voelkerding et al., *Clinical Chemistry,* 55: 641-658 (2009).

Non-limiting examples of NGS technologies and platforms include sequencing-by-synthesis (also known as "pyrosequencing") (as implemented, e.g., using the GS-FLX 454 Genome Sequencer, 454 Life Sciences (Branford, Conn.), ILLUMINA SOLEXA Genome Analyzer (Illumina Inc., San Diego, Calif.), or the ILLUMINA HISEQ 2000 Genome Analyzer (Illumina), or as described in, e.g., Ronaghi et al., *Science,* 281(5375): 363-365 (1998)), sequencing-by-ligation (as implemented, e.g., using the SOLID platform (Life Technologies Corporation, Carlsbad, Calif.) or the POLONATOR G.007 platform (Dover Systems, Salem, N.H.)), single-molecule sequencing (as implemented, e.g., using the PACBIO RS system (Pacific Biosciences (Menlo Park, Calif.) or the HELISCOPE platform (Helicos Biosciences (Cambridge, Mass.)), nano-technology for single-molecule sequencing (as implemented, e.g., using the GRIDON platform of Oxford Nanopore Technologies (Oxford, UK), the hybridization-assisted nano-pore sequencing (HANS) platforms developed by Nabsys (Providence, R.I.), and the ligase-based DNA sequencing platform with DNA nanoball (DNB) technology referred to as probe-anchor ligation (cPAL)), electron microscopy-based technology for single-molecule sequencing, and ion semiconductor sequencing.

The method may comprise inducing autologous antigen presenting cells (APCs) of the patient to present the mutated amino acid sequence. The APCs may include any cells which present peptide fragments of proteins in association with major histocompatibility complex (MHC) molecules on their cell surface. The APCs may include, for example, any one or more of macrophages, DCs, langerhans cells, B-lymphocytes, and T-cells. Preferably, the APCs are DCs. By using autologous APCs from the patient, the inventive methods may, advantageously, identify T cells that have antigenic specificity for a mutated amino acid sequence encoded by a cancer-specific mutation that is presented in the context of an MHC molecule expressed by the patient. The MHC molecule can be any MHC molecule expressed by the patient including, but not limited to, MHC Class I, MHC Class II, HLA-A, HLA-B, HLA-C, HLA-DM, HLA-DO, HLA-DP, HLA-DQ, and HLA-DR molecules. The inventive methods may, advantageously, identify mutated amino acid sequences presented in the context of any MHC molecule expressed by the patient without using, for example, epitope prediction algorithms to identify MHC molecules or mutated amino acid sequences, which may be useful only for a select few MHC class I alleles and may be constrained by the limited availability of reagents to select mutation-reactive T cells (e.g., an incomplete set of MHC tetramers). Accordingly, in an embodiment of the invention, the inventive methods advantageously identify mutated amino acid sequences presented in the context of any MHC molecule expressed by the patient and are not limited to any particular MHC molecule. Preferably, the autologous APCs are antigen-negative autologous APCs.

Inducing autologous APCs of the patient to present the mutated amino acid sequence may be carried out using any suitable method known in the art. In an embodiment of the invention, inducing autologous APCs of the patient to present the mutated amino acid sequence comprises pulsing the autologous APCs with peptides comprising the mutated amino acid sequence or a pool of peptides, each peptide in the pool comprising a different mutated amino acid sequence. Each of the mutated amino acid sequences in the pool may be encoded by a gene containing a cancer specific mutation. In this regard, the autologous APCs may be cultured with a peptide or a pool of peptides comprising the mutated amino acid sequence in a manner such that the APCs internalize the peptide(s) and display the mutated amino acid sequence(s), bound to an MHC molecule, on the cell membrane. In an embodiment in which more than one gene is identified, each gene containing a cancer-specific mutation that encodes a mutated amino acid sequence, the method may comprise pulsing the autologous APCs with a pool of peptides, each peptide in the pool comprising a different mutated amino acid sequence. Methods of pulsing APCs are known in the art and are described in, e.g., Solheim (Ed.), *Antigen Processing and Presentation Protocols* (*Methods in Molecular Biology*), Human Press, (2010). The peptide(s) used to pulse the APCs may include the mutated amino acid(s) encoded by the cancer-specific mutation. The peptide(s) may further comprise any suitable number of contiguous amino acids from the endogenous protein encoded by the identified gene on each of the carboxyl side and the amino side of the mutated amino acid(s). The number of contiguous amino acids from the endogenous protein flanking each side of the mutation is not limited and may be, for example, about 4, about 5, about 6, about 7, about 8, about 9, about 10, about 11, about 12, about 13, about 14, about 15, about 16, about 17, about 18, about 19, about 20, or a range defined by any two of the foregoing values. Preferably, the peptide(s) comprise(s) about 12 contiguous amino acids from the endogenous protein on each side of the mutated amino acid(s).

In an embodiment of the invention, inducing autologous APCs of the patient to present the mutated amino acid sequence comprises introducing a nucleotide sequence encoding the mutated amino acid sequence into the APCs. The nucleotide sequence is introduced into the APCs so that the APCs express and display the mutated amino acid sequence, bound to an MHC molecule, on the cell membrane. The nucleotide sequence encoding the mutated amino acid may be RNA or DNA. Introducing a nucleotide sequence into APCs may be carried out in any of a variety of different ways known in the art as described in, e.g., Solheim et al. supra. Non-limiting examples of techniques that are useful for introducing a nucleotide sequence into APCs include transformation, transduction, transfection, and electroporation. In an embodiment in which more than one gene is identified, the method may comprise preparing more than one nucleotide sequence, each encoding a mutated amino acid sequence encoded by a different gene, and introducing each nucleotide sequence into a different population of autologous APCs. In this regard, multiple populations of autologous APCs, each population expressing and displaying a different mutated amino acid sequence, may be obtained.

In an embodiment in which more than one gene is identified, each gene containing a cancer-specific mutation that encodes a mutated amino acid sequence, the method may comprise introducing a nucleotide sequence encoding the more than one gene. In this regard, in an embodiment of the invention, the nucleotide sequence introduced into the autologous APCs is a TMG construct, each minigene comprising a different gene, each gene including a cancer-specific mutation that encodes a mutated amino acid sequence. Each minigene may encode one mutation identified by the inventive methods flanked on each side of the mutation by any suitable number of contiguous amino acids from the endogenous protein encoded by the identified gene, as described herein with respect to other aspects of the invention. The number of minigenes in the construct is not limited and may include for example, about 5, about 10, about 11, about 12, about 13, about 14, about 15, about 20, about 25, or more, or a range defined by any two of the foregoing values. The APCs express the mutated amino acid sequences encoded by the TMG construct and display the mutated amino acid sequences, bound to an MHC molecule, on the cell membranes. In an embodiment, the method may comprise preparing more than one TMG construct, each construct encoding a different set of mutated amino acid sequences encoded by different genes, and introducing each TMG construct into a different population of autologous APCs. In this regard, multiple populations of autologous APCs, each population expressing and displaying mutated amino acid sequences encoded by different TMG constructs, may be obtained.

The method may comprise culturing autologous T cells of the patient with the autologous APCs that present the mutated amino acid sequence. The T cells can be obtained from numerous sources in the patient, including but not limited to tumor, blood, bone marrow, lymph node, the thymus, or other tissues or fluids. The T cells can include any type of T cell and can be of any developmental stage, including but not limited to, CD4+/CD8+ double positive T cells, CD4+ helper T cells, e.g., Th1 and Th2 cells, CD8+ T cells (e.g., cytotoxic T cells), tumor infiltrating cells (e.g., tumor infiltrating lymphocytes (TIL)), peripheral blood T cells, memory T cells, naïve T cells, and the like. The T cells may be CD8+ T cells, CD4+ T cells, or both CD4+ and CD8+ T cells. The method may comprise co-culturing the autologous T cells and autologous APCs so that the T cells encounter the mutated amino acid sequence presented by the APCs in such a manner that the autologous T cells specifically bind to and immunologically recognize a mutated amino acid sequence presented by the APCs. In an embodiment of the invention, the autologous T cells are co-cultured in direct contact with the autologous APCs.

The method may comprise selecting the autologous T cells that (a) were co-cultured with the autologous APCs that present the mutated amino acid sequence and (b) have antigenic specificity for the mutated amino acid sequence presented in the context of a MHC molecule expressed by the patient. The phrase "antigenic specificity," as used herein, means that the autologous T cells can specifically bind to and immunologically recognize the mutated amino acid sequence encoded by the cancer-specific mutation. The selecting may comprise identifying the T cells that have antigenic specificity for the mutated amino acid sequence and separating them from T cells that do not have antigenic specificity for the mutated amino acid sequence. Selecting the autologous T cells having antigenic specificity for the mutated amino acid sequence may be carried out in any suitable manner. In an embodiment of the invention, the method comprises expanding the numbers of autologous T cells, e.g., by co-culturing with a T cell growth factor, such as interleukin (IL)-2 or IL-15, or as described herein with respect to other aspects of the invention, prior to selecting the autologous T cells. In an embodiment of the invention, the method does not comprise expanding the numbers of autologous T cells with a T cell growth factor, such as IL-2 or IL-15 prior to selecting the autologous T cells.

For example, upon co-culture of the autologous T cells with the APCs that present the mutated amino acid sequence, T cells having antigenic specificity for the mutated amino acid sequence may express any one or more of a variety of T cell activation markers which may be used to identify those T cells having antigenic specificity for the mutated amino acid sequence. Such T cell activation markers may include, but are not limited to, programmed cell death 1 (PD-1), lymphocyte-activation gene 3 (LAG-3), T cell immunoglobulin and mucin domain 3 (TIM-3), 4-1BB, OX40, and CD107a. Accordingly, in an embodiment of the invention, selecting the autologous T cells that have antigenic specificity for the mutated amino acid sequence comprises selecting the T cells that express any one or more of PD-1, LAG-3, TIM-3, 4-1BB, OX40, and CD107a. Cells expressing one or more T cell activation markers may be sorted on the basis of expression of the marker using any of a variety of techniques known in the art such as, for example, fluorescence-activated cell sorting (FACS) or magnetic-activated cell sorting (MACS) as described in, e.g., Turcotte et al., *Clin. Cancer Res.*, 20(2): 331-43 (2013) and Gros et al., *J. Clin. Invest.*, 124(5): 2246-59 (2014).

In another embodiment of the invention, selecting the autologous T cells that have antigenic specificity for the mutated amino acid sequence comprises selecting the T cells (i) that secrete a greater amount of one or more cytokines upon co-culture with APCs that present the mutated amino acid sequence as compared to the amount of the one or more cytokines secreted by a negative control or (ii) in which at least twice as many of the numbers of T cells secrete one or more cytokines upon co-culture with APCs that present the mutated amino acid sequence as compared to the numbers of negative control T cells that secrete the one or more cytokines. The one or more cytokines may comprise any cytokine the secretion of which by a T cell is characteristic of T cell activation (e.g., a T cell receptor (TCR) expressed by the T cells specifically binding to and immunologically recognizing the mutated amino acid sequence). Non-limiting examples of cytokines, the secretion of which is characteristic of T cell activation, include IFN-γ, IL-2, and tumor necrosis factor alpha (TNF-α), granulocyte/monocyte colony stimulating factor (GM-CSF), IL-4, IL-5, IL-9, IL-10, IL-17, and IL-22.

For example, the autologous T cells may be considered to have "antigenic specificity" for the mutated amino acid sequence if the T cells secrete at least twice as much IFN-γ upon co-culture with (a) antigen-negative APCs pulsed with a concentration of a peptide comprising the mutated amino acid sequence (e.g., about 0.05 ng/mL to about 10 µg/mL, e.g., 0.05 ng/mL, 0.1 ng/mL, 0.5 ng/mL, 1 ng/mL, 5 ng/mL, 100 ng/mL, 1 µg/mL, 5 µg/mL, or 10 µg/mL) or (b) APCs into which a nucleotide sequence encoding the mutated amino acid sequence has been introduced as compared to the amount of IFN-γ secreted by a negative control. The negative control may be, for example, autologous T cells (e.g., derived from peripheral blood mononuclear cells (PBMC)) co-cultured with (a) antigen-negative APCs pulsed with the same concentration of an irrelevant peptide (e.g., the wild-type amino acid sequence, or some other peptide with a different sequence from the mutated amino acid sequence) or (b) APCs into which a nucleotide sequence encoding an irrelevant peptide sequence has been introduced. The autologous T cells may also have "antigenic specificity" for the mutated amino acid sequence if the T cells secrete a greater amount of IFN-γ upon co-culture with antigen-negative APCs pulsed with higher concentrations of a peptide comprising the mutated amino acid sequence as compared to a negative control, for example, the negative control described above. IFN-γ secretion may be measured by methods known in the art such as, for example, enzyme-linked immunosorbent assay (ELISA).

Alternatively or additionally, the autologous T cells may be considered to have "antigenic specificity" for the mutated amino acid sequence if at least twice as many of the numbers of T cells secrete IFN-γ upon co-culture with (a) antigen-negative APCs pulsed with a concentration of a peptide comprising the mutated amino acid sequence or (b) APCs into which a nucleotide sequence encoding the mutated amino acid sequence has been introduced as compared to the numbers of negative control T cells that secrete IFN-γ. The concentration of peptide and the negative control may be as described herein with respect to other aspects of the invention. The numbers of cells secreting IFN-γ may be measured by methods known in the art such as, for example, ELISPOT.

While T cells having antigenic specificity for the mutated amino acid sequence may both (1) express any one or more T cells activation markers described herein and (2) secrete a greater amount of one or more cytokines as described herein, in an embodiment of the invention, T cells having antigenic specificity for the mutated amino acid sequence may express any one or more T cell activation markers without secreting a greater amount of one or more cytokines or may secrete a greater amount of one or more cytokines without expressing any one or more T cell activation markers.

In another embodiment of the invention, selecting the autologous T cells that have antigenic specificity for the mutated amino acid sequence comprises selectively growing the autologous T cells that have antigenic specificity for the mutated amino acid sequence. In this regard, the method may comprise co-culturing the autologous T cells with autologous APCs in such a manner as to favor the growth of the T cells that have antigenic specificity for the mutated amino acid sequence over the T cells that do not have antigenic specificity for the mutated amino acid sequence. Accordingly, a population of T cells is provided that has a higher proportion of T cells that have antigenic specificity for the mutated amino acid sequence as compared to T cells that do not have antigenic specificity for the mutated amino acid sequence.

In an embodiment of the invention, the method further comprises obtaining multiple fragments of a tumor from the patient, separately co-culturing autologous T cells from each of the multiple fragments with the autologous APCs that present the mutated amino acid sequence as described herein with respect to other aspects of the invention, and separately assessing the T cells from each of the multiple fragments for antigenic specificity for the mutated amino acid sequence, as described herein with respect to other aspects of the invention.

In an embodiment of the invention in which T cells are co-cultured with autologous APCs expressing multiple mutated amino acid sequences (e.g., multiple mutated amino acid sequences encoded by a TMG construct or multiple mutated amino acid sequences in a pool of peptides pulsed onto autologous APCs), selecting the autologous T cells may further comprise separately assessing autologous T cells for an antigenic specificity for each of the multiple mutated amino acid sequences. For example, the inventive method may further comprise separately inducing autologous APCs of the patient to present each mutated amino acid sequence encoded by the construct (or included in the pool), as described herein with respect to other aspects of the invention (for example, by providing separate APC populations, each presenting a different mutated amino acid sequence encoded by the construct (or included in the pool)). The method may further comprise separately co-culturing autologous T cells of the patient with the different populations of autologous APCs that present each mutated amino acid sequence, as described herein with respect to other aspects of the invention. The method may further comprise separately selecting the autologous T cells that (a) were co-cultured with the autologous APCs that present the mutated amino acid sequence and (b) have antigenic specificity for the mutated amino acid sequence presented in the context of a MHC molecule expressed by the patient, as described herein with respect to other aspects of the invention. In this regard, the method may comprise determining which mutated amino acid sequence encoded by a TMG construct that encodes multiple mutated amino acid sequences (or included in the pool) are immunologically recognized by the autologous T cells (e.g., by process of elimination).

In an embodiment of the invention, the method further comprises expanding the numbers of selected autologous T cells to obtain a population of T cells that have antigenic specificity for the mutated amino acid sequence encoded by the cancer-specific mutation. Expansion of the numbers of selected cells can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.*, 26:332-42 (2003); and Riddell et al., *J. Immunol. Methods*, 128:189-201 (1990). In an embodiment, expansion of the numbers of T cells is carried out by culturing the T cells with OKT3 antibody, IL-2, and feeder PBMC (e.g., irradiated allogeneic PBMC). In this regard, the inventive methods may, advantageously, generate a large number of T cells having antigenic specificity for the mutated amino acid sequence.

The T cells isolated by the inventive methods may be useful for preparing cells for adoptive cell therapies. In this regard, an embodiment of the invention provides a method of preparing a population of T cells that have antigenic specificity for a mutated amino acid sequence encoded by a cancer-specific mutation, the method comprising isolating T cells as described herein with respect to other aspects of the invention, and expanding the numbers of selected autologous T cells to obtain a population of T cells that have antigenic specificity for the mutated amino acid sequence encoded by the cancer-specific mutation. Expanding the numbers of selected cells may be carried out as described herein with respect to other aspects of the invention.

Another embodiment of the invention provides an isolated population of cells prepared according to any of the methods described herein with respect to other aspects of the invention. The population of cells can be a heterogeneous population comprising the T cells having antigenic specificity for the mutated amino acid sequence encoded by the cancer-specific mutation in addition to at least one other cell, e.g., a PBMC which does not have antigenic specificity for the mutated amino acid sequence encoded by the cancer-specific mutation, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of (e.g., consisting essentially of) T cells having antigenic specificity for the mutated amino acid sequence encoded by the cancer-specific mutation. The population also can be a clonal population of cells, in which all cells of the population are clones of a single T cell, such that all cells of the population have antigenic specificity for the mutated amino acid sequence encoded by the cancer-specific mutation. In one embodiment of the invention, the population of cells is a clonal population comprising T cell having antigenic specificity for the mutated amino acid sequence encoded by the cancer-specific mutation, as described herein. In an embodiment of the invention, about 1% to about 100%, for example, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 96%, about 97%, about 98%, about 99%, or about 100%, or a range defined by any two of the foregoing values, of the population of cells comprises T cells that have antigenic specificity for the mutated amino acid sequence. Without being bound to a particular theory or mechanism, it is believed that populations of cells that comprise a high proportion of T cells that have antigenic specificity for the mutated amino acid sequence advantageously may have a lower proportion of irrelevant cells that may hinder the function of the T cell, e.g., the ability of the T cell to target the destruction of cancer cells and/or treat or prevent cancer.

The inventive populations of cells can be formulated into a composition, such as a pharmaceutical composition. In this regard, the invention provides a pharmaceutical composition comprising any of the inventive populations of cells and a pharmaceutically acceptable carrier. The inventive pharmaceutical composition can comprise an inventive population of cells in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive population of cells under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive population of cells, as well as by the particular method used to administer the inventive population of cells. Accordingly, there are a variety of suitable formulations of the pharmaceutical composition of the invention. Suitable formulations may include any of those for oral, parenteral, subcutaneous, intravenous, intramuscular, intraarterial, intrathecal, or interperitoneal administration. More than one route can be used to administer the inventive population of cells, and in certain instances, a particular route can provide a more immediate and more effective response than another route.

Preferably, the inventive population of cells is administered by injection, e.g., intravenously. When the inventive population of cells is to be administered, the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumin.

It is contemplated that the inventive populations of cells and pharmaceutical compositions can be used in methods of treating or preventing cancer. Without being bound to a particular theory or mechanism, the inventive T cells, are believed to bind specifically to a mutated amino acid sequence encoded by a cancer-specific mutation, such that a TCRexpressed by the cell, is able to mediate an immune response against a target cell expressing the mutated amino acid sequence. In this regard, the invention provides a method of treating or preventing cancer in a mammal, comprising administering to the mammal any of the pharmaceutical compositions or populations of cells described herein, in an amount effective to treat or prevent cancer in the mammal.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the cancer being treated or prevented. For example, treatment or prevention can include promoting the regression of a tumor. Also, for purposes herein, "prevention" can encompass delaying the onset of the cancer, or a symptom or condition thereof.

For purposes of the invention, the amount or dose of the inventive population of cells or pharmaceutical composition administered (e.g., numbers of cells when the inventive population of cells is administered) should be sufficient to effect, e.g., a therapeutic or prophylactic response, in the mammal over a reasonable time frame. For example, the dose of the inventive population of cells or pharmaceutical composition should be sufficient to bind to a mutated amino acid sequence encoded by a cancer-specific mutation, or detect, treat or prevent cancer in a period of from about 2 hours or longer, e.g., 12 to 24 or more hours, from the time of administration. In certain embodiments, the time period could be even longer. The dose will be determined by the efficacy of the particular inventive population of cells or pharmaceutical composition administered and the condition of the mammal (e.g., human), as well as the body weight of the mammal (e.g., human) to be treated.

Many assays for determining an administered dose are known in the art. For purposes of the invention, an assay, which comprises comparing the extent to which target cells are lysed or IFN-γ is secreted by T cells upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art.

The dose of the inventive population of cells or pharmaceutical composition also will be determined by the existence, nature and extent of any adverse side effects that might accompany the administration of a particular inventive population of cells or pharmaceutical composition. Typically, the attending physician will decide the dosage of the inventive population of cells or pharmaceutical composition with which to treat each individual patient, taking into consideration a variety of factors, such as age, body weight, general health, diet, sex, inventive population of cells or pharmaceutical composition to be administered, route of administration, and the severity of the condition being treated.

In an embodiment in which the inventive population of cells is to be administered, the number of cells administered per infusion may vary, for example, in the range of one million to 100 billion cells; however, amounts below or above this exemplary range are within the scope of the invention. For example, the daily dose of inventive host cells can be about 1 million to about 150 billion cells (e.g., about 5 million cells, about 25 million cells, about 500 million cells, about 1 billion cells, about 5 billion cells, about 20 billion cells, about 30 billion cells, about 40 billion cells, about 60 billion cells, about 80 billion cells, about 100 billion cells, about 120 billion cells, about 130 billion cells, about 150 billion cells, or a range defined by any two of the foregoing values), preferably about 10 million to about 130 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, about 100 billion cells, about 110 billion cells, about 120 billion cells, about 130 billion cells, or a range defined by any two of the foregoing values), more preferably about 100 million cells to about 130 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells, about 50 billion cells, about 75 billion cells, about 90 billion cells, about 100 billion cells, about 110 billion cells, about 120 billion cells, about 130 billion cells, or a range defined by any two of the foregoing values).

For purposes of the inventive methods, wherein populations of cells are administered, the cells can be cells that are allogeneic or autologous to the mammal. Preferably, the cells are autologous to the mammal.

Another embodiment of the invention provides any of the isolated population of cells or pharmaceutical compositions described herein for use in treating or preventing cancer in a mammal.

The cancer may, advantageously, be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, cholangiocarcinoma, chronic lymphocytic leukemia, chronic myeloid cancer, colon cancer, esophageal cancer, uterine cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, urinary bladder cancer, solid tumors, and liquid tumors. Preferably, the cancer is an epithelial cancer. In an embodiment, the cancer is cholangiocarcinoma, melanoma, colon cancer, or rectal cancer.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). Preferably, the mammals are from the order Artiodactyla, including Bovines (cows) and Swines (pigs) or of the order Perssodactyla, including Equines (horses). Preferably, the mammals are of the order Primates, Ceboids, or Simoids (monkeys) or of the order Anthropoids (humans and apes). A more preferred mammal is the human. In an especially preferred embodiment, the mammal is the patient expressing the cancer-specific mutation.

The following examples further illustrate the invention but, of course, should not be construed as in any way limiting its scope.

EXAMPLES

The materials and methods for Examples 1-7 are set forth below.
Whole-Exomic Sequencing
Whole-exomic sequencing of cryopreserved tumor tissue (embedded in OCT) and normal peripheral blood cells was performed by Personal Genome Diagnostics (PGDx, Baltimore, Md.) as described in Jones et al., *Science* 330: 228-231 (2010). The average number of distinct high quality sequence reads at each base was 155 and 160 for tumor and normal (PBMC) DNA, respectively.
Patient Treatment and Generation of Tumor Infiltrating Lymphocytes (TIL) for Adoptive Cell Therapy
Patient 3737 was enrolled in the institutional-review board (IRB)-approved protocol: "A Phase II Study Using Short-Term Cultured, Autologous Tumor-Infiltrating Lymphocytes Following a Lymphocyte Depleting Regimen in Metastatic Digestive Tract Cancers" (Trial registration ID: NCT01174121), which was designed to evaluate the safety and effectiveness of the adoptive transfer of autologous, ex vivo expanded tumor-infiltrating lymphocytes (TIL) in patients with gastrointestinal cancers.

TIL used for patient's first treatment was generated as described in Jin et al., *J. Immunother.*, 35: 283-292 (2012). Briefly, resected tumors were minced into approximately 1-2 mm fragments and individual fragments were placed in wells of a 24-well plate containing 2 ml of complete media (CM) containing high dose IL-2 (6000 IU/ml, Chiron, Emeryville, Calif.). CM consisted of RPMI supplemented with 10% in-house human serum, 2 mM L-glutamine, 25 mM HEPES and 10 μg/ml gentamicin. Additionally, a mixed tumor digest was also cultured in CM with high dose IL-2. After the initial outgrowth of T cells (between 2-3 weeks), $5\times10^6$ T cells from select cultures were rapidly expanded in gas-permeable G-Rex100 flasks using irradiated allogeneic PBMC at a ratio of 1 to 100 in 400 ml of 50/50 medium, supplemented with 5% human AB serum, 3000 IU/ml of IL-2, and 30 ng/ml of OKT3 antibody (Miltenyi Biotec, Bergisch Gladbach, Germany). 50/50 media was composed of a 1 to 1 mixture of CM with AIM-V media. All cells were cultured at 37° C. with 5% $CO_2$. The numbers of cells were rapidly expanded for two weeks prior to infusion. Patient 3737 underwent a non-myeloablative lymphodepleting regimen composed of cyclophosphamide and fludarabine prior to receiving 42.4 billion total T cells in conjunction with four doses of high dose IL-2.

TIL used for the patient's second treatment was generated in a similar manner as the first treatment with the following changes. The first treatment product (Patient 3737-TIL) was composed of a combination of 5 individual TIL cultures. These 5 cultures were individually assessed for expression of CD4 and Vβ22, and reactivity against mutated ERBB2IP, and one culture was found to be highly enriched in Vβ22+ ERBB2IP-mutation-reactive CD4+ T cells. This one TIL culture (after the initial outgrowth with high dose IL-2) was then rapidly expanded as described above. The patient underwent an identical non-myeloablative lymphodepleting regimen as the first treatment prior to receiving 126 billion total T cells in conjunction with four doses of high dose IL-2.
Generation of TMG Constructs
Briefly, for each non-synonymous substitution mutation identified by whole exome sequencing, a "minigene" construct encoding the corresponding amino acid change flanked by 12 amino acids of the wild-type protein sequence was made. Multiple minigenes were genetically fused together to generate a TMG construct. These minigene constructs were codon optimized and synthesized as DNA String constructs (Life Technologies, Carlsbad Calif.). TMGs were then cloned into the pcDNA3.1 vector using In-Fusion technology (Clontech, Mountain View, Calif.). Site-directed mutagenesis was used to generate the nine "wild-type reversion" TMG-1 constructs (Gene Oracle, Mountain View, Calif.). The nucleotide sequence of all TMGs was verified by standard Sanger sequencing (Macrogen and Gene Oracle).
Generation of Autologous APCs
Monocyte-derived, immature DCs were generated using the plastic adherence method. Briefly, autologous pheresis samples were thawed, washed, set to $5\text{-}10\times10^6$ cells/ml with neat AIM-V media (Life Technologies) and then incubated at approximately $1\times10^6$ cells/cm$^2$ in an appropriate sized tissue culture flask and incubated at 37° C., 5% $CO_2$. After 90 minutes (min), non-adherent cells were collected, and the flasks were vigorously washed with AIM-V media, and then incubated with AIM-V media for another 60 min. The flasks were then vigorously washed again with AIM-V media and then the adherent cells were incubated with DC media. DC media comprised of RPMI containing 5% human serum (collected and processed in-house), 100 U/ml penicillin and 100 μg/ml streptomycin, 2 mM L-glutamine, 800 IU/ml GM-CSF and 800 U/ml IL-4 (media supplements were from Life Technologies and cytokines were from Peprotech). On day 3, fresh DC media was added to the cultures. Fresh or freeze/thawed DCs were used in experiments on day 5-7 after initial stimulation. In all experiments, flow cytometry was used to phenotype the cells for expression of CD11c, CD14, CD80, CD86, and HLA-DR (all from BD Bioscience) to ensure that the cells were predominantly immature DCs (CD11c+, CD14−, CD80$^{low}$, CD86+, and HLA-DR+; data not shown).

Antigen presenting B cells were generated using the CD40L and IL-4 stimulation method. Briefly, human CD19- microbeads (Miltenyi Biotec) were used to positively select B cells from autologous pheresis samples. CD19+ cells were then cultured with irradiated (6000 rad) 3T3 cells stably expressing CD40L (3T3-CD40L) at approximately a 1:1 ratio in B-cell media. B-cell media comprised of IMDM media (Life Technologies) supplemented with 7.5-10% human serum (in-house), 100 U/ml penicillin and 100 µg/ml streptomycin (Life Technologies), 10 µg/ml gentamicin (CellGro, Manassas, Va.), 2 mM L-glutamine (Life Technologies), and 200 U/ml IL-4 (Peprotech). Fresh B-cell media was added starting on day 3, and media added or replaced every 2-3 days thereafter. Additional irradiated 3T3-CD40L feeder cells were also added as required. Antigen presenting B cells were typically used in experiments 2-3 weeks after initial stimulation.

Generation of In Vitro Transcribed RNA (IVT) RNA

Plasmids encoding the tandem minigenes were linearized with the restriction enzyme Sac II. A control pcDNA3.1/V5-His-TOPO vector encoding GFP was linearized with Not I. Restriction digests were terminated with EDTA, sodium acetate and ethanol precipitation. Complete plasmid digestion was verified by standard agarose gel electrophoresis. Approximately 1 µg of linearized plasmid was used for the generation of IVT RNA using the message machine T7 Ultra kit (Life Technologies) as directed by the manufacturer. RNA was precipitated using the $LiCl_2$ method, and RNA purity and concentrations were assessed using a NanoDrop spectrophotometer. RNA was then aliquoted into microtubes and stored at −80° C. until use.

RNA Transfections

APCs (DCs or B cells) were harvested, washed 1× with PBS, and then resuspended in Opti-MEM (Life Technologies) at $10-30\times10^6$ cells/ml. IVT RNA (4 µg or 8 µg) was aliquoted to the bottom of a 2 mm gap electroporation cuvette, and 50 µl or 100 µl of APCs were added directly to the cuvette. The final RNA concentration used in electroporations was thus 80 µg/ml. Electroporations were carried out using a BTX-830 square wave electroporator. DCs were electroporated with 150 V, 10 ms, and 1 pulse, and B cells were electroporated with 150 V, 20 ms, and 1 pulse. Transfection efficiencies using these settings were routinely between 70-90% as assessed with GFP RNA (data not shown). All steps were carried out at room temperature. Following electroporation, cells were immediately transferred to polypropylene tubes containing DC- or B-cell media supplemented with the appropriate cytokines. Transfected cells were incubated overnight (12-14 h) at 37° C., 5% $CO_2$. Cells were washed 1× with PBS prior to use in co-culture assays.

Peptide Pulsing

Autologous B cells were harvested, washed, and then resuspended at $1\times10^6$ cells/ml in B-cell media supplemented with IL-4, and then incubated with 1 µg/ml of a 25-mer peptide overnight (12-14 h) at 37° C., 5% $CO_2$. After overnight pulsing, B cells were then washed 2× with PBS, and then resuspended in T-cell media and immediately used in co-culture assays. The peptides used were: mutated ERBB2IP (TSFLSINSKEETGHLENGNKYPNLE (SEQ ID NO: 73)); wild-type ERBB2IP (TSFLSINSKEETEHLENGNKYPNLE (SEQ ID NO: 45)); and, as a negative control, mutated ALK (RVLKGGSVRKLRHAKQLVLELGEEA (SEQ ID NO: 46)). The mutated ERBB2IP peptide was purchased from three different sources (GenScript, Piscataway, N.J., Peptide 2.0, Chantilly, Va., and SelleckChem, Houston Tex.) with all yielding the same in vitro results, while the wild-type ERBB2IP and mutated ALK peptides were purchased from Peptide 2.0. For culturing allogeneic EBV-B cells, RPMI media containing 10% FBS, 100 U/ml penicillin and 100 µg/ml streptomycin (Life Technologies), 10 µg/ml gentamicin (CeliGro), and 2 mM L-glutamine was used instead of B-cell media.

T-Cell Sorting, Expansion, and Cloning

The BD FACSAria IIu and BD FACSJazz were used in all experiments requiring cell sorting. In indicated experiments, sorted T cells were expanded using excess irradiated (4000 rad) allogeneic feeder cells (pool of three different donor leukapheresis samples) in 50/50 media containing 30 ng/ml anti-CD3 antibody (OKT3) and 3000 IU/ml IL-2. Limiting dilution cloning was carried out in 96-well round bottom plates using the above stimulation conditions with 5e4 feeder cells per well and 1-2 T cells per well. Media was exchanged starting at approximately 1 week post stimulation and then every other day or as required. Cells were typically used in assays, or further expanded, at approximately 2-3 weeks after the initial stimulation.

Co-Culture Assays: IFN-γ ELISPOT and ELISA, Flow Cytometry for Cell Surface Activation Markers, and Intracellular Cytokine Staining (ICS)

When DCs were used as APCs, approximately $3.5\times10^4$ to $7\times10^4$ DCs were used per well of a 96-well flat or round-bottom plate. When B cells were used as APCs, approximately $2\times10^5$ cells were used per well of a 96-well round-bottom plate. In ELISPOT assays, $1\times10^3$ to $1\times10^4$ effector T cells were used per well, and in flow cytometry assays, $1\times10^5$ effector T cells were used per well. T cells were typically thawed and rested in IL-2 containing 50/50 media (3000 IU/ml IL-2) for two days and then washed with PBS (3×) prior to co-culture assays. All co-cultures were performed in the absence of exogenously added cytokines. For all assays, plate-bound OKT3 (0.1 µg/ml or 1 µg/ml) was used as a positive control.

In experiments involving HLA blocking antibodies, the following antibodies were used: pan-class-II (clone: IVA12), pan-class-I (clone: W6/32), HLA-DR (clone: HB55), HLA-DP (clone: B7/21), and HLA-DQ (clone: SPV-L3). Cells were blocked with 20-50 µg/ml of the indicated antibody for 1-2 h at 37° C., 5% $CO_2$ prior to co-culture with T cells. T4 are T cells that have been transduced with an HLA-DR4-restricted TCR that is reactive against an epitope in tyrosinase. DMFS is an HLA-A2-restricted T-cell line reactive against MART-1. 624-CIITA is a HLA-A2 and HLA-DR4-positive melanoma cell line that stably expresses MHC-II due to ectopic expression of CIITA (class II, MHC, transactivator), and is positive for MART-1 and tyrosinase expression.

For IFN-γ ELISPOT assays, briefly, ELIIP plates (Millipore, MAIPSWU) were pre-treated with 50 µl of 70% ethanol per well for 2 min, washed 3× with PBS, and then coated with 50 µl of 10 µg/ml IFN-γ capture antibody (Mabtech, clone: 1-D1K) and incubated overnight in the fridge. For OKT3 controls, wells were coated with a mixture of IFN-γ capture antibody (10 µg/ml) and OKT3 (1 µg/ml). Prior to co-culture, the plates were washed 3× with PBS, followed by blocking with 50/50 media for at least 1 h at room temperature (RT). After 20-24 h of co-culture, cells were flicked out of the plate, washed 6× with PBS+0.05% Tween-20 (PBS-T), and then incubated for 2 h at RT with 100 µl/well of a 0.22 µm filtered 1 µg/ml biotinylated anti-human IFN-γ detection antibody solution (Mabtech, clone: 7-B6-1). The plate was then washed 3× with PBS-T, followed by a 1 h incubation with 100 µl/well of streptavidin-ALP (Mabtech, Cincinnati, Ohio, diluted 1:3000). The plate was then washed 6× with PBS followed by development with 100 µl/well of 0.45 µm filtered BCIP/NBT substrate solution (KPL, Inc.). The reaction was stopped by rinsing thoroughly with cold tap water. ELISPOT plates were scanned and counted using an ImmunoSpot plate reader and associated software (Cellular Technologies, Ltd, Shaker Heights, Ohio).

Expression of the T-cell activation markers OX40 and 4-1BB was assessed by flow cytometry at approximately t=22-26 h post-stimulation. Briefly, cells were pelleted, washed with FACS buffer (1×PBS supplemented with 1% FBS and 2 mM EDTA), and then stained with the appropriate antibodies for approximately 30 min, at 4° C. in the dark. Cells were washed at least once with FACS buffer prior to acquisition on a BD FACSCanto II flow cytometer. All data were gated on live (PI negative), single cells.

Cytokine production was assessed using intracellular cytokine staining (ICS) and flow cytometry. Briefly, after target and effector cells were combined in the wells of a 96-well plate, both GolgiStop and GolgiPlug were added to the culture (BD Biosciences). GolgiStop and GolgiPlug were used at ½ of the concentration recommended by the manufacturer. At t=6 h post stimulation, cells were processed using the Cytofix/Cytoperm kit (BD Biosciences, San Jose, Calif.) according to the manufacturer's instructions. Briefly, cells were pelleted, washed with FACS buffer, and then stained for cell surface markers (described above). Cells were then washed 2× with FACS buffer prior to fixation and permeabilization. Cells were then washed with Perm/Wash buffer and stained with antibodies against cytokines for 30 min, at 4° C. in the dark. Cells were washed 2× with Perm/Wash buffer and resuspended in FACS buffer prior to acquisition on a FACSCantoII flow cytometer. All flow cytometry data were analyzed using FLOWJO software (TreeStar Inc).

IFN-γ in serum samples was detected using a human IFN-γ ELISA kit as directed by the manufacturer (Thermo Scientific, Waltham, Mass.).

Flow Cytometry Antibodies

The following titrated anti-human antibodies were used for cell surface staining: CCR7-FITC (clone: 150503), CD45RO-PE-Cy7 (clone: UCHL1), CD62L-APC (clone: DREG-56), CD27-APC-1-17 (clone: M-T271), CD4-efluor 605NC (clone: OKT4), CD57-FITC (clone: NK-1), CD28-PE-Cy7 (clone: CD28.2), CD127-APC (clone: eBioRDR5), CD3-AF700 (clone: UCHT1), CD4-FITC, PE-Cy7, APC-H7 (clone: SK3), CD8-PE-Cy7 (clone: SK1), Vβ22-PE (clone: IMMU 546), Vβ5.2-PE (clone: 36213), OX40-PE-Cy7 or FITC (clone: Ber-ACT35), 4-1BB-APC (clone: 4B4-1), and CD107a-APC-H7 (clone: H4A3). All antibodies were from BD Biosciences, except CD4-efluor605NC (eBioscience), Vβ22-PE and Vβ5.2-PE (Beckman Coulter), and 4-1BB-APC and OX40-PE-Cy7 (BioLegend). The following optimally titrated anti-human antibodies were used for intracellular cytokine staining: IFN-γ-FITC (clone: 4S.B3), IL-2-APC (clone: MQ1-17H12), TNF-PerCPCy5.5 or APC (clone: MAb11), IL-17-PE (clone: eBio64DEC17), and IL-4-PE-Cy7 (clone: 8D4-8). All ICS antibodies were from eBioscience except IL-4-PE-Cy7 (BD Bioscience). The IO Mark B Mark TCR V kit was used to assess the TCR-Vβ repertoire (Beckman Coulter).

Sequencing of the ERBB2IP Mutation

Sanger sequencing was used to validate the ERBB2IP mutation found by whole-exomic sequencing. Total RNA was extracted from snap frozen T cells or tumor tissues (OCT block) using the RNeasy Mini kit (Qiagen). Total RNA was then reverse transcribed to cDNA using ThermoScript reverse transcriptase with oligo-dT primers (Life Technologies). Normal and tumor cDNA were then used as templates in a PCR with the following ERBB2IP primers flanking the mutation: ERBB2IP Seq Forward: 5'-TGT TGA CTC AAC AGC CAC AG-3' (SEQ ID NO: 47); and ERBB2IP Seq Reverse: 5'-CTG GAC CAC TTT TCT GAG GG-3' (SEQ ID NO: 48). Phusion DNA polymerase (Thermo Scientific) was used with the recommended 3-step protocol with a 58° C. annealing temperature (15 sec) and a 72° C. extension (30 sec). PCR products were isolated by standard agarose gel electrophoresis and gel extraction (Clontech). Products were directly sequenced using the same PCR primers (Macrogen).

Quantitative PCR

Total RNA was extracted from snap frozen T cells or tumor tissues (OCT block) using the RNeasy Mini kit (Qiagen, Venlo, Netherlands). Total RNA was then reverse transcribed to cDNA using qScript cDNA Supermix (Quanta Biosciences, Gaithersburg, Md.). Gene-specific Taqman primer and probe sets for human β-actin (catalogue #: 401846) and ERBB2IP (catalogue #: 4331182) were purchased from Life Technologies. Quantitative PCR was carried out with TAQMAN Fast Advanced Master Mix using the 7500 Fast Real Time PCR machine (both from Applied Biosystems). Specificity of amplified products was verified by standard agarose gel electrophoresis. All calculated threshold cycles (Ct) were 30 or below.

TCR-Vβ Deep Sequencing

TCR-Vβ deep sequencing was performed by immunoSEQ, Adaptive Biotechnologies (Seattle, Wash.) on genomic DNA isolated from peripheral blood, T cells, and frozen tumor tissue using the DNeasy blood and tissue kit (Qiagen). The number of total productive TCR reads per sample ranged from 279,482 to 934,672. Only productive TCR rearrangements were used in the calculations of TCR frequencies.

TCR Sequencing and Construction of the ERBB2IP-Mutation Reactive TCR

T cells were pelleted and total RNA isolated (RNeasy Mini kit, Qiagen). Total RNA then underwent 5'RACE as directed by manufacturer (SMARTer RACE cDNA amplification kit, Clontech) using TCR-α and -β chain constant primers. Program 1 of the kit was used for the PCR, with a modification to the extension time (2 min instead of 3 min). The sequences of the α and β chain constant primers are: TCR-α, 5'-GCC ACA GCA CTG TGC TCT TGA AGT CC-3' (SEQ ID NO: 49); TCR-β, 5'-CAG GCA GTA TCT GGA GTC ATT GAG-3' (SEQ ID NO: 50). TCR PCR products were then isolated by standard agarose gel electrophoresis and gel extraction (Clontech). Products were then either directly sequenced or TOPO-TA cloned followed by sequencing of individual colonies (Macrogen). For sequencing of known Vβ22+ T-cell clones, cDNA was generated from RNA using qScript cDNA Supermix (Quanta Biosciences). These cDNAs then were used as templates in a PCR using the TCR-β constant primer (above) and the Vβ22-specific primer: 5'-CAC CAT GGA TAC CTG GCT CGT ATG C-3' (SEQ ID NO: 51). PCR products were isolated by standard agarose gel electrophoresis and gel extraction (Clontech). Products were directly sequenced (Macrogen) using the nested TCR-β chain constant primer: 5'-ATT CAC CCA CCA GCT CAG-3' (SEQ ID NO: 52).

Construction of the Vβ22+ ERBB2IP-mutation TCR was done by fusing the Vβ22+ TCR-α V-D-J regions to the mouse TCR-α constant chain, and the Vβ22+ TCR-β-V-D-J regions to the mouse TCR-β constant chains. The α and β chains were separated by a furin SGSG P2A linker. Use of mouse TCR constant regions promotes pairing of the introduced TCR and also facilitates identification of positively transduced T cells by flow cytometry using an antibody specific for the mouse TCR-β chain (eBioscience). The TCR construct was synthesized and cloned into the MSGV1 retroviral vector (Gene Oracle).

TCR Transduction of Peripheral Blood T Cells

Autologous pheresis samples were thawed and set to $2\times10^6$ cells/ml in T-cell media, which consists of a 50/50 mixture of RPMI and AIM-V media supplemented with 5% in-house human serum, 10 µg/ml gentamicin (CeliGro), 100 U/ml penicillin and 100 µg/ml streptomycin, 1.25 µg/ml amphotericin B (Fungizone) and 2 mM L-glutamine (all from Life Technologies). $2\times10^6$ cells (1 ml) were stimulated in a 24-well plate with 50 ng/ml soluble OKT3 (Miltenyi Biotec) and 300 IU/ml rhu IL-2 (Chiron) for 2 days prior to retroviral transduction. To generate transient retroviral supernatants, the retroviral vector MSGV1 encoding the Vβ22-positive, ERBB2IP-mutation-specific TCR (1.5 µg/well) and the envelope encoding plasmid RD114 (0.75 µg/well) were co-transfected into the retroviral packaging cell line 293 GP ($1\times10^6$ cells per well of a 6-well poly-D-lysine-coated plates, plated the day prior to transfection) using lipofectamine 2000 (Life Technologies). Retroviral supernatants were collected at 42-48 h after transfection, diluted 1:1 with DMEM media, and then centrifuged onto retronectin-coated (10 µg/ml, Takara), non-tissue culture-treated 6-well plates at 2,000 g for 2 h at 32° C. Activated T cells ($2\times10^6$ per well, at $0.5\times10^6$ cells/ml in IL-2 containing T-cell media) were then spun onto the retrovirus plates for 10 min at 300 g. Activated T cells were transduced overnight, removed from the plates and further cultured in IL-2 containing T-cell media. GFP and mock transduction controls were included in transduction experiments. Cells were typically assayed 10-14 days post-retroviral transduction.

Example 1

This example demonstrates a method of identifying one or more genes in the nucleic acid of a cancer cell of a patient, each gene containing a cancer-specific mutation that encodes a mutated amino acid sequence.

A 43-year old woman with widely metastatic cholangiocarcinoma (Patient (Pt.) 3737) who progressed through multiple chemotherapy regimens was enrolled onto a TIL-based adoptive cell therapy (ACT) protocol for patients with gastrointestinal (GI) cancers. The clinical characteristics of patient 3737 are shown in Table 1.

TABLE 1

| Sex | Age | Primary | Metastatic sites | Prior Therapy | Prior IL-2 | Harvest site* | ECOG+ Status | HLA-I | HLA-II |
|---|---|---|---|---|---|---|---|---|---|
| F | 43 | Intrahepatic cholangiocarcinoma (poorly differentiated) | Lungs, liver | Cisplatin + gemcitibine, gemcitibine, taxotere | No | Lung | 0 | A*26 B*38 B*52 C*12 | DRB1*0405 DRB1*1502 DQB1*0301 DQB1*0601 DPB1*0401 DPB1*10401 |

*Harvest site for generation of TIL and for whole exomic sequencing.
+Performance status: ECOG, Eastern Cooperative Oncology Group Lung metastases were resected and used as a source for whole-exomic sequencing and generation of T cells for treatment. Table 2 shows the somatic mutations identified by whole-exome sequencing of a metastatic lung nodule from patient 3737. The tumor nodule was estimated to be approximately 70% tumor by pathological analysis of a hematoxylin and eosin (H&E) stained section. Whole-exomic sequencing revealed 26 non-synonymous mutations (Table 2).

TABLE 2

| | | | Mutation Position | | | | |
|---|---|---|---|---|---|---|---|
| Gene Symbol | Gene Description | Transcript Accession | Nucleotide (genomic) | Amino Acid (protein) | Mutation Type | Consequence | % Mutant Reads* |
| ALK | anaplastic lymphoma receptor tyrosine kinase | CCDS33172.1 | chr2_29996620-29996620_C_T | 137R > H | Substitution | Nonsynonymous coding | 30% |
| AR | androgen receptor | CCDS14387.1 | chrX_66858483-66858483_C | NA | Insertion | Frameshift | 31% |
| CD93 | CD93 molecule | CCDS13149.1 | chr20_23012929-23012929_C_T | 634R > Q | Substitution | Nonsynonymous coding | 26% |
| DIP2C | DIP2 disco-interacting protein 2 homolog C (*Drosophila*) | CCDS7054.1 | chr10_365545-365545_C_T | NA | Substitution | Splice site acceptor | 25% |
| ERBB2IP | erbb2 interacting protein | CCDS3990.1 | chr5_65385316-65385316_A_G | 805E > G | Substitution | Nonsynonymous coding | 59% |
| FCER1A | Fc fragment of IgE; high affinity I; receptor for; α polypeptide | CCDS1184.1 | chr1_157544227-157544227_G_C | 219D > H | Substitution | Nonsynonymous coding | 30% |
| GRXCR1 | glutaredoxin; cysteine rich 1 | CCDS43225.1 | chr4_42590102-42590102_C_T | 21A > V | Substitution | Nonsynonymous coding | 18% |
| HLA-DOA | HLA class II histocompatibility antigen, DO α chain precursor | CCDS4763.1 | chr6_33085209-33085209_C_T | NA | Substitution | Splice site donor | 36% |

TABLE 2-continued

| Gene Symbol | Gene Description | Transcript Accession | Mutation Position Nucleotide (genomic) | Mutation Position Amino Acid (protein) | Mutation Type | Consequence | % Mutant Reads* |
|---|---|---|---|---|---|---|---|
| KIF9 | kinesin family member 9 | CCDS2752.1 | chr3__47287859-47287859__T__C | 155T > A | Substitution | Nonsynonymous coding | 20% |
| KLHL6 | kelch-like 6 (Drosophila) | CCDS3245.2 | chr3__184692410-184692413__CAGA__ | NA | Deletion | Frameshift | 20% |
| LHX9 | LIM homeobox 9 | CCDS1393.1 | chr1__196164923-196164923__A__ | NA | Deletion | Frameshift | 21% |
| LONRF3 | LON peptidase N-terminal domain and ring finger 3 | CCDS35374.1 | chrX__118007666-118007666__A__C | NA | Substitution | Splice site donor | 10% |
| NAGS | N-acetylglutamate synthase | CCDS11473.1 | chr17__39440355-39440355__G__A | 412R > H | Substitution | Nonsynonymous coding | 29% |
| NLRP2 | NLR family; pyrin domain containing 2 | CCDS12913.1 | chr19__60186650-60186650__G__T | 591S > I | Substitution | Nonsynonymous coding | 32% |
| PDZD2 | PDZ domain containing 2 | CCDS34137.1 | chr5__32124833-32124833__A__ | NA | Deletion | Frameshift | 30% |
| POU5F2 | POD domain, class 5, transcription factor 2 | NM__153216 | chr5__93102847-93102847__A__C | 60V > G | Substitution | Nonsynonymous coding | 34% |
| RAC3 | ras-related C3 botulinum toxin substrate 3 (rho family; small GTP binding protein Rac3) | CCDS11798.1 | chr17__77584690-77584690__C__A | 125T > N | Substitution | Nonsynonymous coding | 27% |
| RAP1GDS1 | RAP1; GTP-GDP dissociation stimulator 1 | CCDS43253.1 | chr4__99532209-99532209__C__A | 198L > I | Substitution | Nonsynonymous coding | 19% |
| RASA1 | RAS p21 protein activator (GTPase activating protein) 1 | CCDS34200.1 | chr5__86703757-86703757__C__T | 589R > C | Substitution | Nonsynonymous coding | 63% |
| RETSAT | retinol saturase (all-trans-retinol 13; 14-reductase) | CCDS1972.1 | chr2__85424308-85424308__C__T | 553R > K | Substitution | Nonsynonymous coding | 11% |
| SEC24D | SEC24 family; member D (S. cerevisiae) | CCDS3710.1 | chr4__119872085-119872085__A__G | 901M > T | Substitution | Nonsynonymous coding | 18% |
| SENP3 | SUMO1/sentrin/SMT3 specific peptidase 3 | ENST00000321337 | chr17__7408824-7408824__A__G | 292M > V | Substitution | Nonsynonymous coding | 33% |
| SLIT1 | slit homolog 1 (Drosophila) | CCDS7453.1 | chr10__98753840-98753840__G__C | 1280N > K | Substitution | Nonsynonymous coding | 45% |
| TARBP1 | TAR (HIV-1) RNA binding protein 1 | CCDS1601.1 | chr1__232649342-232649342__C__A | 655G > V | Substitution | Nonsynonymous coding | 18% |
| TGM6 | transglutaminase 6 | CCDS13025.1 | chr20__2332325-2332325__G__A | 398D > N | Substitution | Nonsynonymous coding | 51% |
| TTC39C | tetratricopeptide repeat domain 39C | CCDS32804.1 | chr18__19966475-19966475__A__C | 503N > T | Substitution | Nonsynonymous coding | 24% |

Example 2

This example demonstrates a method of inducing autologous APCs of a patient to present the mutated amino acid sequence; co-culturing a population of autologous T cells of the patient with the autologous APCs that present the mutated amino acid sequence; and selecting the autologous T cells that (a) were co-cultured with the autologous APCs that present the mutated amino acid sequence and (b) have antigenic specificity for the mutated amino acid sequence presented in the context of a MHC molecule expressed by the patient.

For each mutation identified in Example 1, a mini-gene construct was designed that encoded for the mutated amino acid flanked on each side by 12 amino acids from the endogenous protein. Multiple mini-genes were synthesized in tandem to generate tandem mini-gene (TMG) constructs (Table 3). In Table 3, the underlining denotes mutated amino acids and neo-sequences encoded by point mutations, or nucleotide insertions or deletions. For splice-site donor mutations (HLA-DOA and LONRF3), mutant minigene transcripts were designed that continued into the downstream intron until the next stop codon, based on the assumption that the mutations prevented splicing at that site. The splice-site acceptor mutation in DIP2C was not assessed.

TABLE 3

| TMG | Mutated Gene | Mutated Minigene Amino Acid Sequence | TMG Amino Acid Sequence |
|---|---|---|---|
| 1 | ALK | RVLKGGSVRKLRHAKQLVLELGEEA (SEQ ID NO: 1) | RVLKGGSVRKLRHAKQLVLELGEEAQNAADSYSWVPE QAESRAMENQYSPTSFLSINSKEETGHLENGNKYPNLEF IPLLVVILFAVHTGLFISTQQQVIESDRPRKVRFRIVSSHS GRVLKEVYEIYNESLFDLLSALPYVGPSVTPMTGKKLRDD YLASLHPRLHSIYVSEGYPDIKQELLRCDIICKGGHSTVTD LQVGTKLDLRDDKDNIERLRDKKLAPI (SEQ ID NO: 26) |
| | CD93 | QNAADSYSWVPEQAESRAMENQYSP (SEQ ID NO: 2) | |
| | ERBB2IP | TSFLSINSKEETGHLENGNKYPNLE (SEQ ID NO: 3) | |
| | FCER1A | FIPLLVVILFAVHTGLFISTQQQVT (SEQ ID NO: 4) | |
| | GRXCR1 | ESDRPRKVRFRIVSSHSGRVLKEVY (SEQ ID NO: 5) | |

TABLE 3-continued

| TMG | Mutated Gene | Mutated Minigene Amino Acid Sequence | TMG Amino Acid Sequence |
|---|---|---|---|
| | KIF9 | E1YNESLFDLLSALPYVGPSVIPMT (SEQ ID NO: 6) | |
| | NAGS | GKKLRDDYLASLHPRLHSIYVSEGY (SEQ ID NO: 7) | |
| | NLRP2 | PDIKQELLRCDIICKGGHSTVTDLQ (SEQ ID NO: 8) | |
| | RAC3 | VGTKLDLRDDKDNIERLRDKKLAPI (SEQ ID NO: 9) | |
| 2 | RAP1GDS1 | VKLLGIHCQNAAITEMCLVAFGNLA (SEQ ID NO: 10) | VKLLGIHCQNAAITEMCLVAFGNLANLRKSSPGTSNKCL |
| | RASA1 | NLRKSSPGTSNKCLRQVSSLVLHIE (SEQ ID NO: 11) | RQVSSLVLHIELGRLHPCVMASLKAQSPIPNLYLTGLLPI |
| | RETSAT | LGRLHPCVMASLKAQSPIPNLYLTG (SEQ ID NO: 12) | HTLDVKSTTLPAAVRCSESRLMTMDNFGKHYTLKSEAP |
| | | | LYVGGMPVMTMDNFGKHYTLKSEAPLYVGGMPVHD |
| | SEC24D | LLPIHTLDVKSTTLPAAVRCSESRL (SEQ ID NO: 13) | GPFVFAEVNANYITWLWHEDESRQAKEDFSGYDFETRL |
| | | | HVRIHAALASPAVRPGICPGPDGWRIPLGPLPHEF (SEQ |
| | SLIT1 | MTMDNFGKHYTLKSEAPLYVGGMPV (SEQ ID NO: 14) | ID NO: 27) |
| | TARBP1 | AVDVEGMKTQYSVKQRTENVLRIFL (SEQ ID NO: 15) | |
| | TGM6 | HDGPFVFAEVNANYITWLWHEDESR (SEQ ID NO: 16) | |
| | TTC39C | QAKEDFSGYDFETRLHVRIHAALA (SEQ ID NO: 17) | |
| | POU5F2 | PAVRPGICPGPDGWRIPLGPLPHEF (SEQ ID NO: 18) | |
| 3 | SENP3 | VAQELFQGSDLGVAEEAERPGEKAG (SEQ ID NO: 19) | VAQELFQGSDLGVAEEAERPGEKAGGTATTLTDLTNPL |
| | LHX9 | GTATTLTDLTNPLSL (SEQ ID NO: 20) | SLTHIRRIVPGAVSDGRMGSWRAPPTLSVPASPLTLLQS |
| | KLHL6 | THIRRIVPGAVSDGRMGSWRAPPTLSV PASPLTLLQSHFRQQARV (SEQ ID NO: 21) | HFRQQARVRHLSQEFGWLQITPPGIPVHESTATLQHYS |
| | | | SGWAEKSKILSPDSKIQMVSSSQKRALLCLIALLSRKQT |
| | AR | RHLSQEFGWLQITPPGIPVHESTATLQH YSSGWAEKSKIL (SEQ ID NO: 22) | WKIRTCLRRVRQKCFTLLSPQEAGATKDECEGEEGAAG |
| | | | SRDLRSWVTEETGMPNKASKQGPGSTQREGSLEEIPGL |
| | PDZD2 | SPDSKIQMVSSSQKRALLCLIALLSRKQT WKIRTCLRRVRQKCF (SEQ ID NO: 23) | TNIYKLLTSVWGWILWVWGPALAFTSCVTSEIAMRLL (SEQ ID NO: 28) |
| | HLA-DOA | TLLSPQEAGATKDECEGEEGAAGSRDLR SWVT (SEQ ID NO: 24) | |
| | LONRF3 | EETGMPNKASKQGPGSTQREGSLEEIPG LTNIYKLLTSVWGLLRLWVWGPALAFTS CVTSEIAMRLL (SEQ ID NO: 25) | |

Figure 1:
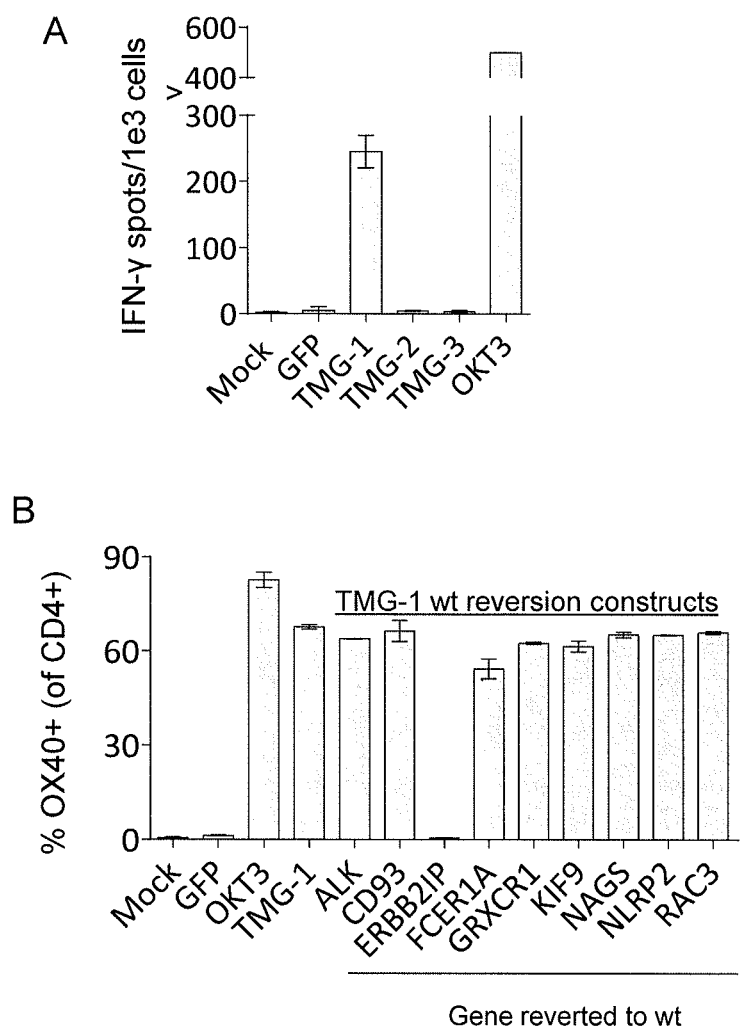

The TMG constructs were then used as templates for the generation of in vitro transcribed (IVT) RNA. Each of these IVT TMG RNAs was then individually transfected into autologous APCs (DCs) followed by a co-culture with TIL to determine whether any of the processed and presented mutated antigens were recognized by TIL. It was observed that 3737-TIL were reactive to a mutated antigen present in TMG-1, but not TMG-2 or TMG-3 (FIG. 1A). Moreover, the reactivity predominated in the CD4+ T-cell population as demonstrated by up-regulation of the activation markers OX40 and 4-1BB (Tables 4A and 4B). Tables 4A and 4B show the percentage of 3737-TIL detected by flow cytometry as having the indicated phenotype following coculture with DCs cultured with the non-specific stimulator OKT3 or DCs transfected with green fluorescent protein (GFP) RNA, or the indicated tandem mini-gene (TMG) construct encoding the various mutations identified by whole-exomic sequencing. Mock-transfected cells were treated with transfection reagent only without addition of nucleic acid. Data were gated on live CD3+ cells.

TABLE 4A

| | 4-1BB−/CD4− | 4-1BB+/CD4− | 4-1BB−/CD4+ | 4-1BB+/CD4+ |
|---|---|---|---|---|
| Mock | 49 | 0 | 51 | 0 |
| GFP | 49 | 0 | 51 | 0 |
| TMG-1 | 47 | 4 | 38 | 11 |
| TMG-2 | 47 | 0 | 53 | 0 |
| TMG-3 | 48 | 0 | 52 | 0 |
| OKT3 | 4 | 41 | 23 | 32 |

TABLE 4B

| | OX40−/CD4− | OX40+/CD4− | OX40−/CD4+ | OX40+/CD4+ |
|---|---|---|---|---|
| Mock | 49 | 0 | 51 | 0 |
| GFP | 48 | 0 | 51 | 1 |
| TMG-1 | 49 | 2 | 16 | 33 |
| TMG-2 | 47 | 0 | 53 | 0 |
| TMG-3 | 48 | 0 | 52 | 0 |
| OKT3 | 38 | 6 | 11 | 45 |

Although some 4-1BB up-regulation was observed in the CD4-negative (CD8+) T-cell population, these cells were sorted and no reactivity against the TMG was found. To determine which of the 9 mutations in TMG-1 was being recognized by 3737-TIL, 9 additional TMG-1 constructs were synthesized, each one containing a reversion of one of the mutations back to the wild-type sequence. Reactivity of 3737-TIL to TMG-1 was abrogated only when the ERBB2 interacting protein (ERBB2IP) mutation was reverted back to the wild-type sequence, indicating that the TIL specifically recognized the ERBB2IP$^{E805G}$ mutation (FIG. 1B).

Figure 2:
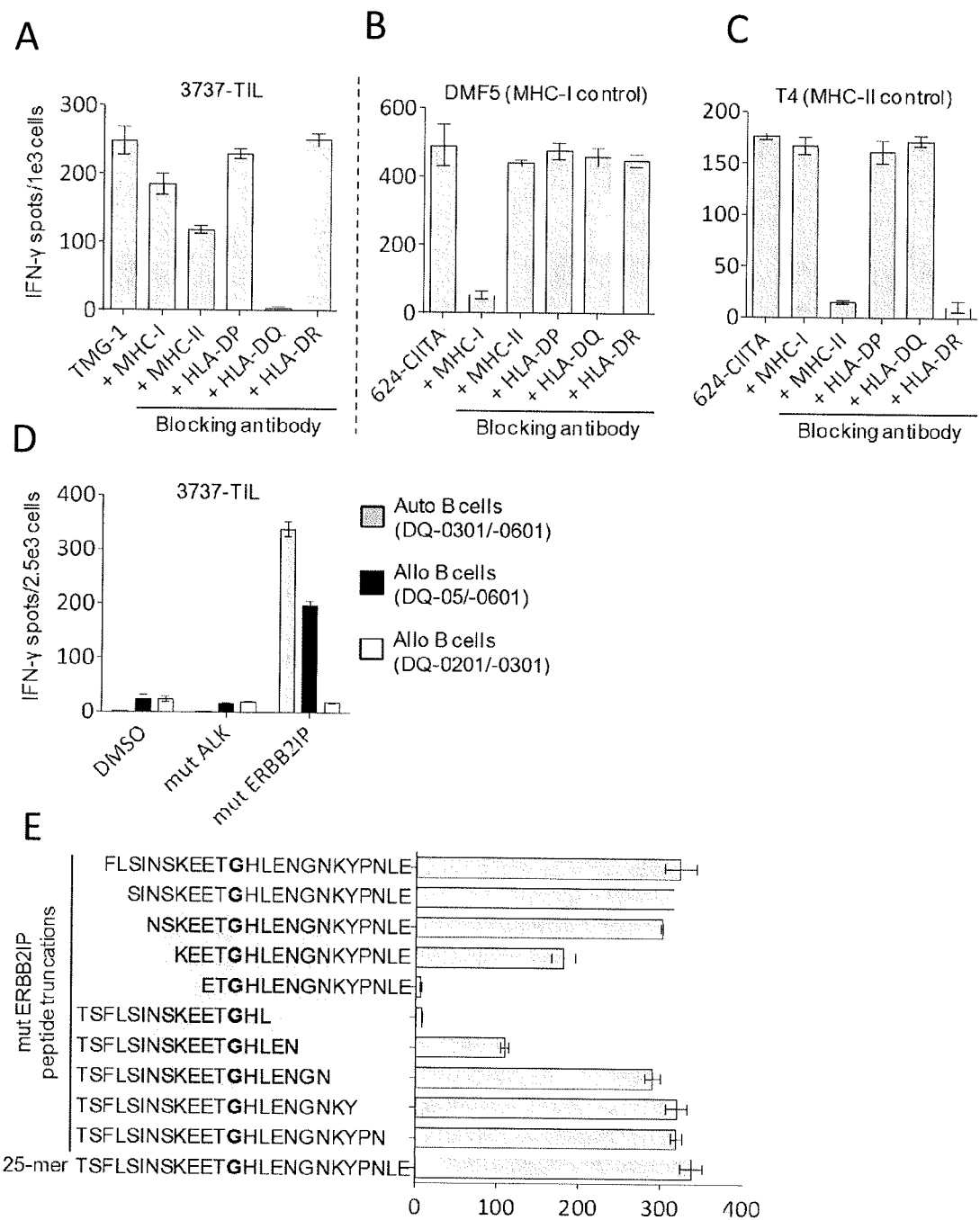

The ERBB2IP-mutation reactive T-cell response was characterized molecularly. An IFN-γ ELISPOT assay was performed, and the results were measured at 20 hours. Patient 3737-TIL were co-cultured with DCs transfected with TMG-1 that had been pre-incubated with nothing, or the indicated HLA-blocking antibodies (against MHC-I, MHC-II, HLA-DP, HLA-DQ, or HLA-DR) (FIG. 2A). As controls for antibody blocking, the HLA-A2 restricted MART-reactive T cell DMFS (FIG. 2B) and the HLA-DR-restricted tyrosinase-reactive T cell T4 (FIG. 2C) were co-cultured with the MART and tyrosinase-positive 624-CIITA melanoma cell line that had been pre-incubated with nothing, or the indicated HLA-blocking antibodies. The response of 3737-TIL was blocked by anti-HLA-DQ antibodies (FIG. 2A).

Another IFN-γ ELISPOT assay was performed, and the results were measured at 20 hours. Patient 3737-TIL were co-cultured with autologous B cells or allogeneic EBV-B cells partially matched at the HLA-DQ locus that had been pulsed overnight with DMSO, mutated (mut) ALK or mut ERBB2IP 25-AA long peptides (FIG. 2D).

Another IFN-γ ELISPOT assay was performed, and the results were measured at 20 hours. Patient 3737-TIL were co-cultured with autologous B cells that had been pulsed overnight with the mut ERBB2IP 25-AA peptide, or the indicated truncated mut ERBB2IP peptides (FIG. 2E).

As shown in FIGS. 2A-2E, the 3737-TIL response was restricted by the HLA-DQB1*0601 allele and the minimal epitope was located within the 13 amino acid sequence NSKEETGHLENGN (SEQ ID NO: 29).

Example 3

This example demonstrates that autologous open repertoire peripheral blood T cells genetically modified with the TCR-Vβ22 chain of the ERBB2IP-specific CD4+ T-cells identified in Example 2 matched with its α chain conferred specific reactivity to the mutated ERBB2IP peptide.

The clonality of the mutated ERBB2IP-specific CD4+ T-cells identified in Example 2 were characterized by sorting them after antigen-specific activation, using OX40 as a marker of activation. These cells were then bulk expanded and cloned by limiting dilution. A flow cytometry-based survey of the TCR-Vβ repertoire demonstrated that the bulk-expanded population was >95% Vβ22+, and that 10/11 clones assessed were purely Vβ22+. TCR sequence analysis revealed the same TCRβ V-D-J sequence in 6/6 Vβ22+ clones tested (Table 5), showing that the majority of the ERBB2IP-mutation reactive T cells was comprised of a dominant Vβ22+ T-cell clone.

TABLE 5

| TCR Vβ | V-D-J nucleotide sequence (CDR3 underlined) | V-D-J amino acid sequence (CDR3 underlined) | Number of Vβ22 (TRBV2) clones with indicated V-D-J |
|---|---|---|---|
| Vβ22 (TRBV2) | GAACCTGAAGTCACCCAGACTCCCAGCCATCAGGT CACACAGATGGGACAGGAAGTGATCTTGCGCTGT GTCCCCATCTCTAATCACTTATACTTCTATTGGTACA GACAAATCTTGGGGCAGAAAGTCGAGTTTCTGGTT TCCTTTTATAATAATGAAATCTCAGAGAAGTCTGAA ATATTCGATGATCAATTCTCAGTTGAAAGGCCTGAT GGATCAAATTTCACTCTGAAGATCCGGTCCACAAA GCTGGAGGACTCAGCCATGTACTTCTGT<u>GCCAGC AGCCTGGGTGACAGGGGTAATGAAAAACTGT TTTTT</u>GGCAGTGGAACCCAGCTCTCTGTCTTGG (SEQ ID NO: 39) | EPEVTQTPSHQVTQMG QEVILRCVPISNHLYFYYR QILGQKVEFLVSFYNNEIS EKSEIFDDQFSVERPDGS NFTLKIRSTKLEDSAMYF <u>CASSLGDRGNEKLFFGS</u> GTQLSVL (SEQ ID NO: 40) | 6/6 |

T-cell clones expressing this Vβ22 TCR specifically produced the cytokine IFN-γ upon stimulation with the mutated ERBB2IP peptide (Table 6). CD4+Vβ22+ clones were co-cultured for 6 hours with OKT3 or autologous B cells pulsed overnight with wild-type (wt) ERBB2IP, mutated (mut) ALK, or mut ERBB2IP 25-AA long peptides. Table 6 shows the percentage of CD4+Vβ22+ and Vβ22− clones that produce intracellular IFN-γ (IFN-γ+) or do not produce intracellular IFN-γ (IFN-γ−) after co-culture as measured by flow cytometry. Data are representative of 2 clones sharing the same TCR-Vβ sequence.

TABLE 6

|  | IFN-γ−/Vβ22− | IFN-γ+/Vβ22− | IFN-γ−/Vβ22+ | IFN-γ+/Vβ22+ |
|---|---|---|---|---|
| mutALK | 1 | 0 | 98 | 1 |
| wtERBB2IP | 1 | 0 | 99 | 0 |
| mutERBB2IP | 1 | 0 | 19 | 80 |
| OKT3 | 3 | 4 | 59 | 34 |

Moreover, autologous open repertoire peripheral blood T cells genetically modified with this TCR-Vβ22 chain matched with its α chain (Table 7) conferred specific reactivity to the mutated ERBB2IP peptide (Tables 8A and 8B), demonstrating that this TCR specifically recognized the ERBB2IP$^{E805G}$ mutation. Autologous open-repertoire peripheral blood T cells were transduced (Td) with the TCR derived from the Vβ22+ clone (Table 8A), or were treated with transduction reagent only without addition of nucleic acid (Mock) (Table 8B), and then assessed for reactivity as described for Table 6. The endogenous Vβ22+ TCR constant regions were swapped with mouse constant regions, allowing for the detection of the introduced TCR using antibodies against the mouse TCRβ constant region (mTCRβ). Plate-bound OKT3 was used as a control in all assays. Tables 8A and 8B show the percentage of mTCRβ+ and mTCRβ-cells that produce intracellular IFN-γ (IFN-γ+) or do not produce intracellular IFN-γ (IFN-γ−) as measured by flow cytometry.

3737-TIL were co-cultured with DCs transfected with TMG-1 or TMG-1 encoding the wild-type (wt) ERBB2IP reversion, and flow cytometry was used to assess OX40 and Vβ22 expression on CD4+ T cells at 24 hours post-stimulation. Plate-bound OKT3 stimulation was used as a positive control. Flow cytometry analysis demonstrated that approximately 25% of the entire 3737-TIL product administered was comprised of the Vβ22+, mutation-reactive T cells (FIG. 3A, Table 9), equating to the infusion of over 10

TABLE 7

| TCR Vα | V-J nucleotide sequence (CDR3 underlined) | V-J amino acid sequence (CDR3 underlined) |
|---|---|---|
| TRAV26-2 | GATGCTAAGACCACACAGCCAAATTCAATGGAG AGTAACGAAGAAGAGCCTGTTCACTTGCCTTGTA ACCACTCCACAATCAGTGGAACTGATTACATACA TTGGTATCGACAGCTTCCCTCCCAGGGTCCAGAG TACGTGATTCATGGTCTTACAAGCAATGTGAACA ACAGAATGGCCTCTCTGGCAATCGCTGAAGACA GAAAGTCCAGTACCTTGATCCTGCACCGTGCTAC CTTGAGAGATGCTGCTGTGTACTACTGC<u>ATCCT GAGACGTCTTAACGACTACAAGCTCAGCTTT GGAGCCGGAACCACAGTAACTGTAAGAGCAA</u> (SEQ ID NO: 41) | DAKTTQPNSMESNEEEPVHLP CNHSTISGTDYIHWYRQLPSQ GPEYVIHGLTSNVNNRMA SLAIAEDRKSSTLILHRATLRDA AVYYC<u>ILRRLNDYKLSFGAGT</u> TVTVRA (SEQ ID NO: 42) |

TABLE 8A

|  | IFN-γ−/mTCRβ− | IFN-γ+/mTCRβ− | IFN-γ−/mTCRβ+ | IFN-γ+/mTCRβ+ |
|---|---|---|---|---|
| mutALK | 16 | 0 | 84 | 0 |
| wtERBB2IP | 15 | 0 | 85 | 0 |
| mutERBB2IP | 19 | 0 | 69 | 12 |
| OKT3 | 14 | 2 | 74 | 10 |

TABLE 8B

|  | IFN-γ−/mTCRβ− | IFN-γ+/mTCRβ− | IFN-γ−/mTCRβ+ | IFN-γ+/mTCRβ+ |
|---|---|---|---|---|
| mutALK | 99 | 1 | 0 | 0 |
| wtERBB2IP | 100 | 0 | 0 | 0 |
| mutERBB2IP | 100 | 0 | 0 | 0 |
| OKT3 | 83 | 17 | 0 | 0 |

Example 4

This example demonstrates a method of treating cancer using the autologous cells identified in Example 2.

Patient 3737 underwent adoptive transfer of 42.4 billion TIL containing CD4+ ERBB2IP mutation-reactive T cells followed by four doses of IL-2 to enhance T-cell proliferation and function. For treatment, Patient 3737 underwent a resection of lung lesions. Tumors were then minced into small fragments and incubated with high dose IL-2 to expand tumor infiltrating lymphocytes (TIL). After an initial expansion of the numbers of cells in IL-2, the numbers of select TIL cultures were further expanded for 2 weeks using a rapid expansion protocol (REP) including irradiated allogeneic peripheral blood feeder cells, OKT3 and IL-2. Prior to cell infusion, the patient was pre-conditioned with cyclophosphamide (CTX: 60 mg/kg, once a day for two days) followed by fludarabine (Flu: 25 mg/m$^2$ for 5 days). Patient 3737-TIL included 42.4 billion TIL containing over 10 billion (25%) ERBB2IP-mutation reactive T cells, and was administered on day 0, followed by IL-2 (Aldesleukin, 7.2e5 IU/kg) every 8 hours. The patient received a total of 4 doses of IL-2.

billion ERBB2IP-mutation specific CD4+ T cells. Table 9 shows the percentage of Vβ22+ and Vβ22− cells that express OX40 (OX40+) or do not express OX40 (OX40−) as measured by flow cytometry.

Figure 3:
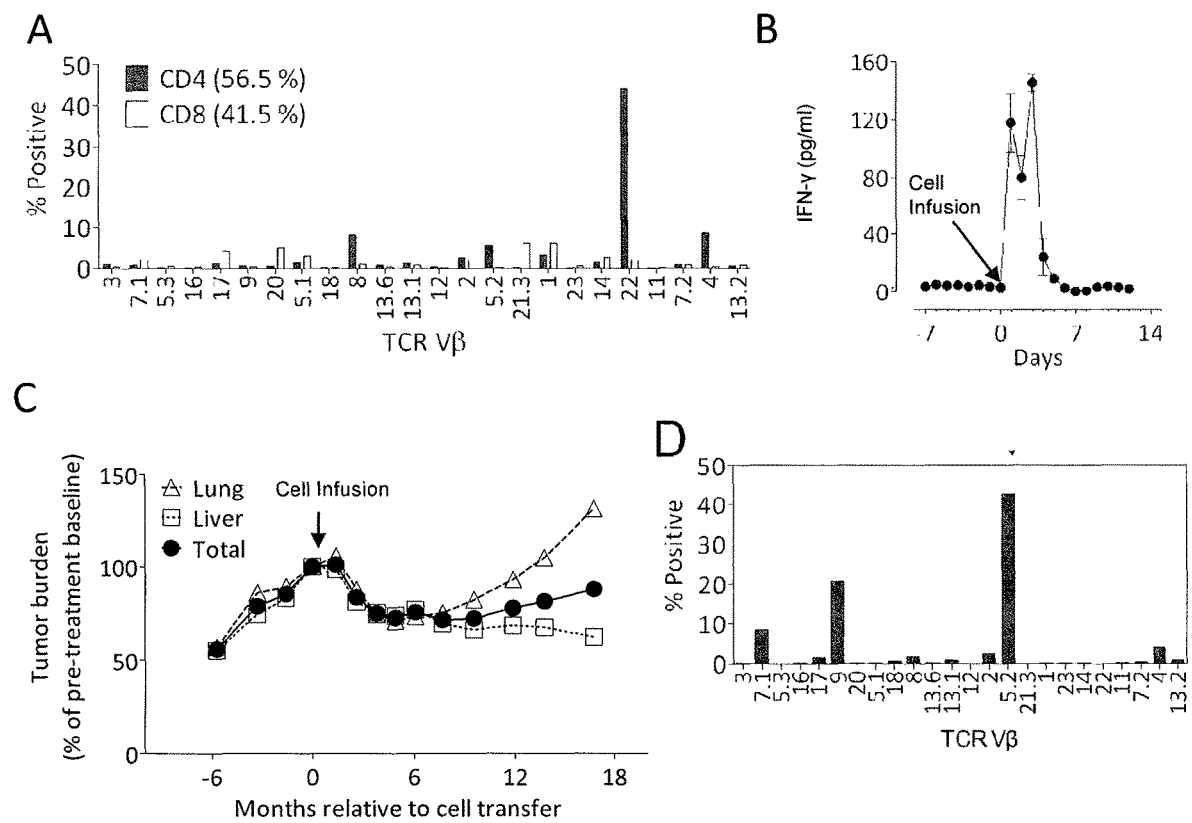
FIG. 3A is a graph showing the percentage of various TCR Vβ clonotypes in 3737-TIL, measured by flow cytometry gated on live CD4+(shaded) or CD8+(unshaded) T cells.
FIG. 3B is a graph showing the IFN-γ levels (pg/ml) detected in patient 3737 serum samples measured at the indicated number of days pre- and post-adoptive cell transfer of 3737-TIL on Day 0 (indicated by arrow). Error bars are standard error of the mean (SEM).
FIG. 3C is a graph showing the total tumor burden (circles) (measured as % of pre-treatment baseline) or tumor burden in the lung (triangles) or liver (squares) at the indicated number of months relative to cell transfer on day 0 (indicated by arrow).
FIG. 3D is a graph showing the percentage of various TCR Vβ clonotypes in CD4+Vβ22–OX40+3737-TIL, as measured by flow cytometry.

An IFN-γ ELISA assay was performed on patient 3737 serum samples pre- and post-adoptive cell transfer of 3737-TIL. The results are shown in FIG. 3B. As shown in FIG. 3B, elevated levels of IFN-γ were detected in the patient's serum for the first five days after cell infusion.

Although the patient had clear evidence of progressive disease prior to the cell infusion, tumor regression was observed by the two month follow-up, and all target lung and liver lesions continued to regress, reaching a maximum reduction of 30% at 7 months post-treatment (FIG. 3C). The patient experienced disease stabilization for approximately 13 months after cell infusion, after which disease progression was observed only in the lungs but not liver.

TABLE 9

|  | Vβ22−/OX40− | Vβ22−/OX40+ | Vβ22+/OX40− | Vβ22+/OX40+ |
|---|---|---|---|---|
| TMG-1 wtERBB2IP | 45 | 0 | 55 | 0 |
| TMG-1 | 33 | 12 | 3 | 52 |
| OKT3 | 19 | 31 | 6 | 44 |

Example 5

This example demonstrates the in vitro phenotype and function of the cells of Example 4.

To determine whether there was evidence that the CD4+ ERBB2IP-mutation-reactive T cells played a role in the disease stabilization, the in vitro phenotype and function of the cells were evaluated. 3737-TIL were co-cultured for 6 hours with autologous B cells pulsed overnight with wild-type (wt) ERBB2IP, mutated (mut) ALK or mut ERBB2IP 25-AA long peptides. Flow cytometry was used to assess expression of Vβ22 and to detect intracellular production of IFN-γ (Table 10A), tumor necrosis factor (TNF) (Table 10B), and IL-2 (Table 10C) in the CD4+ population. The percentage of cells having the indicated phenotypes is shown in Tables 10A-10C. Table 10D displays the percentage of Vβ22+ cells that expressed the indicated number of cytokines. It was found that the Vβ22+ ERBB2IP-mutation reactive CD4+ T cells were polyfunctional Th1 cells, as stimulation with the mutated ERBB2IP peptide induced the robust co-expression of IFN-γ, TNF, and IL-2 (Tables 10A-10C), but little to no IL-4 or IL-17.

TABLE 10A

|  | Vβ22−/IFN-γ− | Vβ22−/IFN-γ+ | Vβ22+/IFN-γ− | Vβ22+/IFN-γ+ |
|---|---|---|---|---|
| mutALK | 45 | 0 | 55 | 0 |
| wtERBB2IP | 44 | 0 | 56 | 0 |
| mutERBB2IP | 40 | 8 | 6 | 47 |
| OKT3 | 29 | 33 | 24 | 14 |

TABLE 10B

|  | Vβ22−/TNF− | Vβ22−/TNF+ | Vβ22+/TNF− | Vβ22+/TNF+ |
|---|---|---|---|---|
| mutALK | 45 | 0 | 55 | 0 |
| wtERBB2IP | 43 | 1 | 56 | 0 |
| mutERBB2IP | 37 | 10 | 3 | 50 |
| OKT3 | 10 | 52 | 6 | 32 |

TABLE 10C

|  | Vβ22−/IL-2− | Vβ22−/IL-2+ | Vβ22+/IL-2− | Vβ22+/IL-2+ |
|---|---|---|---|---|
| mutALK | 45 | 0 | 55 | 0 |
| wtERBB2IP | 43 | 1 | 56 | 0 |
| mutERBB2IP | 38 | 10 | 5 | 47 |
| OKT3 | 27 | 36 | 23 | 14 |

TABLE 10D

| No. cytokines (gated on Vβ22+) | mutALK | wtERBB2IP | OKT3 | mutERBB2IP |
|---|---|---|---|---|
| 0 | 99% | 98% | 12% | 11% |
| 1+ | 1% | 2% | 30% |  |
| 2+ | None | None | 24% |  |
| 3+ | None | None | 34% | 89% |

Further phenotypic characterization revealed that these cells were predominantly effector memory CD4+ T cells with cytolytic potential (Tables 11 and 12). Patient 3737-TIL were assessed by flow cytometry for expression of Vβ22 (representing ERBB2IP-mutation-reactive T cells) and the T-cell differentiation markers CD28, CD45RO, CD57, CCR7, CD127, CD62L, and CD27. Data were gated on live CD3+CD4+ cells. Positive and negative quadrant gates were set using isotype stained or unstained cells. The percentage of cells having the indicated phenotypes is shown in Table 11. Human peripheral blood cells (containing T cells of all differentiation stages) were included in experiments to ensure that the antibodies were working.

TABLE 11

| Vβ22−/CD28− | Vβ22−/CD28+ | Vβ22+/CD28− | Vβ22+/CD28+ |
|---|---|---|---|
| 1 | 56 | 1 | 42 |
| Vβ22−/CD45RO− | Vβ22−/CD45RO+ | Vβ22+/CD45RO− | Vβ22+/CD45RO+ |
| 0 | 57 | 0 | 43 |
| Vβ22−/CD57− | Vβ22−/CD57+ | Vβ22+/CD57− | Vβ22+/CD57+ |
| 48 | 9 | 42 | 1 |
| Vβ22−/CCR7− | Vβ22−/CCR7+ | Vβ22+/CCR7− | Vβ22+/CCR7+ |
| 57 | 0 | 43 | 0 |
| Vβ22−/CD127− | Vβ22−/CD127+ | Vβ22+/CD127− | Vβ22+/CD127+ |
| 25 | 32 | 21 | 22 |
| Vβ22−/CD62L− | Vβ22−/CD62L+ | Vβ22+/CD62L− | Vβ22+/CD62L+ |
| 49 | 8 | 42 | 1 |
| Vβ22−/CD27− | Vβ22−/CD27+ | Vβ22+/CD27− | Vβ22+/CD27+ |
| 57 | 0 | 43 | 0 |

Patient 3737-TIL were co-cultured for 6 hours with OKT3 or autologous B cells pulsed overnight with wild-type (wt) ERBB2IP, mutated (mut) ALK or mut ERBB2IP 25-AA long peptides. Antibodies specific for the degranulation marker CD107a were added at the beginning of the co-culture. Flow cytometry was used to assess expression of Vβ22 and to detect cell surface mobilization of CD107a. Data were gated on the CD4+ population. The percentage of cells having the indicated phenotypes is shown in Table 12.

TABLE 12

|  | Vβ22−/CD107a− | Vβ22−/CD107a+ | Vβ22+/CD107a− | Vβ22+/CD107a+ |
| --- | --- | --- | --- | --- |
| mutALK | 51 | 0 | 48 | 1 |
| wtERBB2IP | 51 | 1 | 48 | 0 |
| mutERBB2IP | 53 | 6 | 19 | 22 |
| OKT3 | 42 | 19 | 26 | 13 |

There also appeared to be a minor population of polyfunctional Vβ22-negative, ERBB2IP-mutation-reactive CD4+ T cells present in 3737-TIL (Tables 9 and 10). These Vβ22-negative cells were sorted by FACS and then rested in IL-2 containing media for 2 days prior to being co-cultured with autologous B cells pulsed overnight with wild-type (wt) ERBB2IP, mutated (mut) ALK or mut ERBB2IP 25-AA long peptides. Flow cytometry was used to assess expression of Vβ22 and to detect intracellular production of IL-2 (Table 13C), TNF (Table 13B), and IFN-γ (Table 13A) in the CD4+ population at 6 hours (h) post-stimulation. The percentage of cells having the indicated phenotypes are shown in Tables 13A-13C.

TABLE 13A

|  | Vβ22−/IFN-γ− | Vβ22−/IFN-γ+ | Vβ22+/IFN-γ− | Vβ22+/IFN-γ+ |
| --- | --- | --- | --- | --- |
| mutALK | 99 | 0 | 1 | 0 |
| wtERBB2IP | 99 | 0 | 1 | 0 |
| mutERBB2IP | 85 | 14 | 0 | 1 |
| OKT3 | 50 | 49 | 0 | 1 |

TABLE 13B

|  | Vβ22−/TNF− | Vβ22−/TNF+ | Vβ22+/TNF− | Vβ22+/TNF+ |
| --- | --- | --- | --- | --- |
| mutALK | 99 | 0 | 1 | 0 |
| wtERBB2IP | 97 | 2 | 1 | 0 |
| mutERBB2IP | 78 | 21 | 0 | 1 |
| OKT3 | 9 | 90 | 0 | 1 |

TABLE 13C

|  | Vβ22−/IL-2− | Vβ22−/IL-2+ | Vβ22+/IL-2− | Vβ22+/IL-2+ |
| --- | --- | --- | --- | --- |
| mutALK | 99 | 0 | 1 | 0 |
| wtERBB2IP | 97 | 2 | 1 | 0 |
| mutERBB2IP | 78 | 21 | 0 | 1 |
| OKT3 | 36 | 63 | 0 | 1 |

Flow cytometry was used to assess expression OX40 and Vβ22 in the CD4+ population at 24 h post stimulation. Cells that upregulated OX40 were sorted and the numbers of the cells were expanded, and the TCR-Vβ repertoire was analyzed by flow cytometry. The results are shown in FIG. 3D. Sorting of the Vβ22-negative cells followed by activation of these cells revealed that one or more additional clonotypes reactive to this epitope were present in 3737-TIL (Tables 13A-13C), the most dominant clonotype of which was Vβ5.2 (FIG. 3D).

The sorted cells described in FIG. 3D were co-cultured for 6 h with autologous B cells pulsed overnight with wt ERBB2IP, mut ALK or mut ERBB2IP 25-AA long peptides. Flow cytometry was used to assess expression of Vβ5.2 and to detect intracellular production of IL-2 (Table 14C), TNF (Table 14B), and IFN-γ (Table 14A) in the CD4+ population. Table 15 displays the percentage of Vβ5.2+ cells that expressed the indicated number of cytokines.

TABLE 14A

|  | Vβ5.2−/IFN-γ− | Vβ5.2−/IFN-γ+ | Vβ5.2+/IFN-γ− | Vβ5.2+/IFN-γ+ |
| --- | --- | --- | --- | --- |
| mutALK | 51 | 0 | 49 | 0 |
| wtERBB2IP | 54 | 0 | 46 | 0 |
| mutERBB2IP | 42 | 13 | 20 | 25 |
| OKT3 | 28 | 23 | 25 | 24 |

TABLE 14B

|  | Vβ5.2−/TNF− | Vβ5.2−/TNF+ | Vβ5.2+/TNF− | Vβ5.2+/TNF+ |
| --- | --- | --- | --- | --- |
| mutALK | 50 | 2 | 48 | 0 |
| wtERBB2IP | 52 | 2 | 46 | 0 |
| mutERBB2IP | 33 | 21 | 3 | 43 |
| OKT3 | 5 | 46 | 3 | 46 |

TABLE 14C

|  | Vβ5.2−/IL-2− | Vβ5.2−/IL-2+ | Vβ5.2+/IL-2− | Vβ5.2+/IL-2+ |
| --- | --- | --- | --- | --- |
| mutALK | 51 | 1 | 48 | 0 |
| wtERBB2IP | 54 | 1 | 45 | 0 |
| mutERBB2IP | 38 | 17 | 14 | 31 |
| OKT3 | 31 | 21 | 27 | 21 |

TABLE 15

| No. cytokines (gated on Vβ5.2+) | mutALK | wtERBB2IP | mutERBB2IP | OKT3 |
| --- | --- | --- | --- | --- |
| 0 | 98% | 98% | 3% | 6% |
| 1+ | 2% | 2% | 11% | 25% |
| 2+ | None | None | 36% | 36% |
| 3+ | None | None | 50% | 33% |

Vβ22-negative cells that upregulated OX40 upon stimulation with mutated ERBB2IP were sorted and the numbers of cells were expanded. RNA from these cells was then isolated and underwent rapid amplification of 5' complementary DNA ends (5'RACE) with TCR-β constant chain primers to identify the expressed TCR-Vβ sequences. TOPO-TA cloning was performed on the polymerase chain reaction (PCR) products and individual colonies were then sequenced. Flow cytometry demonstrated that 40-50% of these T cells were Vβ5.2 (TRBV5-6). By Sanger sequencing, 3/7 TOPO-TA colonies were Vβ5.2 (TRBV5-6) with the sequence shown in Table 16. Table 16 displays the most frequent TCRβ V-D-J sequence of Vβ22-negative ERBB2IP-mutation-reactive T cells.

TABLE 16

| TCR Vβ | V-D-J nucleotide sequence (CDR3 underlined) | V-D-J amino acid sequence (CDR3 underlined) | Number of TOPO-TA clones with indicated V-D-J |
|---|---|---|---|
| Vβ5.2 (TRBV5-6) | GACGCTGGAGTCACCCAAAGTCCCACACACCTGAT CAAAACGAGAGGACAGCAAGTGACTCTGAGATGC TCTCCTAAGTCTGGGCATGACACTGTGTCCTGGTAC CAACAGGCCCTGGGTCAGGGGCCCCAGTTTATCTT TCAGTATTATGAGGAGGAAGAGAGACAGAGAGGC AACTTCCCTGATCGATTCTCAGGTCACCAGTTCCCT AACTATAGCTCTGAGCTGAATGTGAACGCCTTGTT GCTGGGGGACTCGGCCCTCTATCTCTGT<u>GCCAGCA GCAAAGGCCCGGGAGGCAACTACGAGCAGTAC</u>TT CGGGCCGGGCACCAGGCTCACGGTCACAG (SEQ ID NO: 43) | DAGVTQSPTHLIKTR GQQVTLRCSPKSGHD TVSWYQQALGQGPQ FIFQYYEEEERQRGNF PDRFSGHQFPNYSSE LNVNALLLGDSALYLC <u>ASSKGPGGNYEQYFG</u> PGTRLTVT (SEQ ID NO: 44) | 3/7 |

The majority of the Vβ5.2+ cells produced multiple cytokines in an antigen-specific manner (Tables 14A-14C, 15, and 16). There also appeared to be a minor population of Vβ5.2-negative (and Vβ22-negative) CD4+ T cells that recognized mutated ERBB2IP (Tables 14A-14C and 15). Thus, the TIL used to treat patient 3737 contained at least three different polyfunctional CD4+ T-cell clones that recognized the same mutation in ERBB2IP, showing that this mutation was highly immunogenic.

Example 6

This example demonstrates the in vivo persistence of the cells of Example 4.

To determine whether there was evidence that the CD4+ ERBB2IP-mutation-reactive T cells played a role in the disease stabilization, the in vivo persistence of the cells was evaluated. TCR-VP deep sequencing revealed that these clonotypes were rare or not detectable in the peripheral blood prior to ACT (FIGS. 4A and 4B). Ten days after ACT, both clones were present at greater than 2% of the total T cells in the peripheral blood, but declined to less than 0.3% by day 34 post-cell infusion (FIGS. 4A and 4B). Three lung metastases, which were resected nearly a year and a half after ACT, were infiltrated by the ERBB2IP-mutation-reactive T cells (FIGS. 4A and 4B), showing that these cells contributed to the cancer regression and disease stabilization. The Vβ22+ ERBB2IP-mutation-reactive clone was the most frequent clone detected in tumor nodule-3 (Tu-3-Post) and represented nearly 8% of total T cells in the tumor (FIGS. 4A and 4B), whereas this clone was the second and twelfth most frequent in tumor nodules-1 and -2, respectively. The Vβ5.2+ ERBB2IP-mutation-reactive clone was also enriched compared to its frequency in blood in all three tumor nodules (FIGS. 4A and 4B). Thus, patient 3737 experienced tumor regression with stabilization of disease for more than one year after receiving over 10 billion ERBB2IP-mutation-specific polyfunctional Th1 cells which infiltrated and persisted in the metastatic lesions.

Reverse transcriptase quantitative PCR (RT-qPCR) analysis of ERBB2IP expression in Patient 3737-TIL (T cells) and tumors pre-(Tu-Pre) and post adoptive cell transfer was performed. Three separate metastatic lung lesions (Tu-1, -2, -3-Post) were resected approximately 17 months post cell infusion. The results are shown in FIG. 4C, and are relative to β-actin (ACTB). A 350 base pair (bp) segment of the ERBB2IP gene containing the mutation was PCR-amplified from the cDNA samples described for FIG. 4C and Sanger sequenced. The location of the mutation was at nucleotide position 2414 of the coding sequence, corresponding to a change at position 805 of the amino acid sequence. Relatively high levels of ERBB2IP expression in both the original and recurrent lung lesions, as determined by quantitative RT-PCR, were observed (FIG. 4C), and Sanger sequencing validated the presence of the ERBB2IP mutation in all tumor lesions.

Immunohistochemistry analyses of T-cell infiltrates and MHC expression pre- and post-ACT were performed. Post-ACT tumors were harvested approximately 17 months after the first ACT. A positive control (tonsil) was included for all stains. The T-cell infiltrate and MHC expression of the tumors in situ are summarized in Tables 17 and 18, respectively.

TABLE 17

| Tumor Nodule | CD3 | | CD8 | | CD4 | |
|---|---|---|---|---|---|---|
| | Tumor | Stroma | Tumor | Stroma | Tumor | Stroma |
| Pre-1A | 0-1 | 1 | 0-1 | 1 | 0-1 | 1 |
| Pre-2A | 0-1 | 1 | 0-1 | 1 | 0 | 0 |
| Pre-3A | 0 | 0-1 | 0 | 0-1 | 0 | 0 |
| Pre-3B | 0-1 | 1 | 0-1 | 0-1 | 0-1 | 1 |
| Post-1A | 1 | 1 | 1 | 1 | 0-1 | 1 |
| Post-1B | 1 | 2 | 1-2 | 2 | 1 | 2 |
| Post-2A | 0-1 | 1 | 0-1 | 1 | 0-1 | 0-1 |

0, no infiltrate
1, rare to few
2, moderately dense
3, very dense

TABLE 18

| Tumor Nodule | HLA-I | HLA-II (HLA-DR) |
|---|---|---|
| Pre-1A | 1-2, >50% | 0 |
| Pre-2A | 1-2, >50% | 0 |
| Pre-3A | 1, >50% | 0 |
| Pre-3B | 2, >50% | 0 |
| Post-1A | 2-3, >50% | 0 |
| Post-1B | 3, >50% | 0 |
| Post-2A | 2, >50% | 0 |

>50% denotes greater than 50% of the tumor cells were positive.
0, negative
1, weakly positive
2, moderately positive
3, strongly positive Example 7

This example demonstrates the contribution of mutation-reactive Th1 cells to the anti-tumor response of Example 4.

To specifically evaluate the contribution of mutation-reactive Th1 cells to the anti-tumor response in vivo, a TIL product that was comprised of >95% of the Vβ22+ ERBB2IP-mutation-reactive Th1 cells (about 120 billion mutation-reactive cells) was generated and adoptively transferred into patient 3737.

Flow cytometric analysis of the TIL-product used for re-treatment was performed. Table 19 shows that after gating on CD3, 97% were CD4+/CD8−, and of these, 98% were Vβ22+ after further gating on CD4+ cells (Table 20). Re-treatment TIL were co-cultured for 6 h with autologous B cells pulsed overnight with wild-type (wt) or mutated (mut) ERBB2IP 25-AA long peptides. Flow cytometry was used to detect intracellular TNF production in the CD4+ population (Table 20).

TABLE 19

| CD8−/CD4− | CD8−/CD4+ | CD8+/CD4− | CD8+/CD4+ |
|---|---|---|---|
| 0 | 97 | 3 | 0 |

TABLE 20

|  | Vβ22−/TNF− | Vβ22−/TNF+ | Vβ22+/TNF− | Vβ22+/TNF+ |
|---|---|---|---|---|
| wtERBB2IP | 2 | 0 | 98 | 0 |
| mutERBB2IP | 1 | 3 | 3 | 93 |

Again, the patient experienced a decrease in target lesions, but unlike the first treatment, tumor regression was observed even at the first month follow-up and continued as of the follow-up at 4 months after the second treatment (FIG. 4D). Tumor regression was continuing as of the follow up at 8 months after the second treatment.

Figure 7:
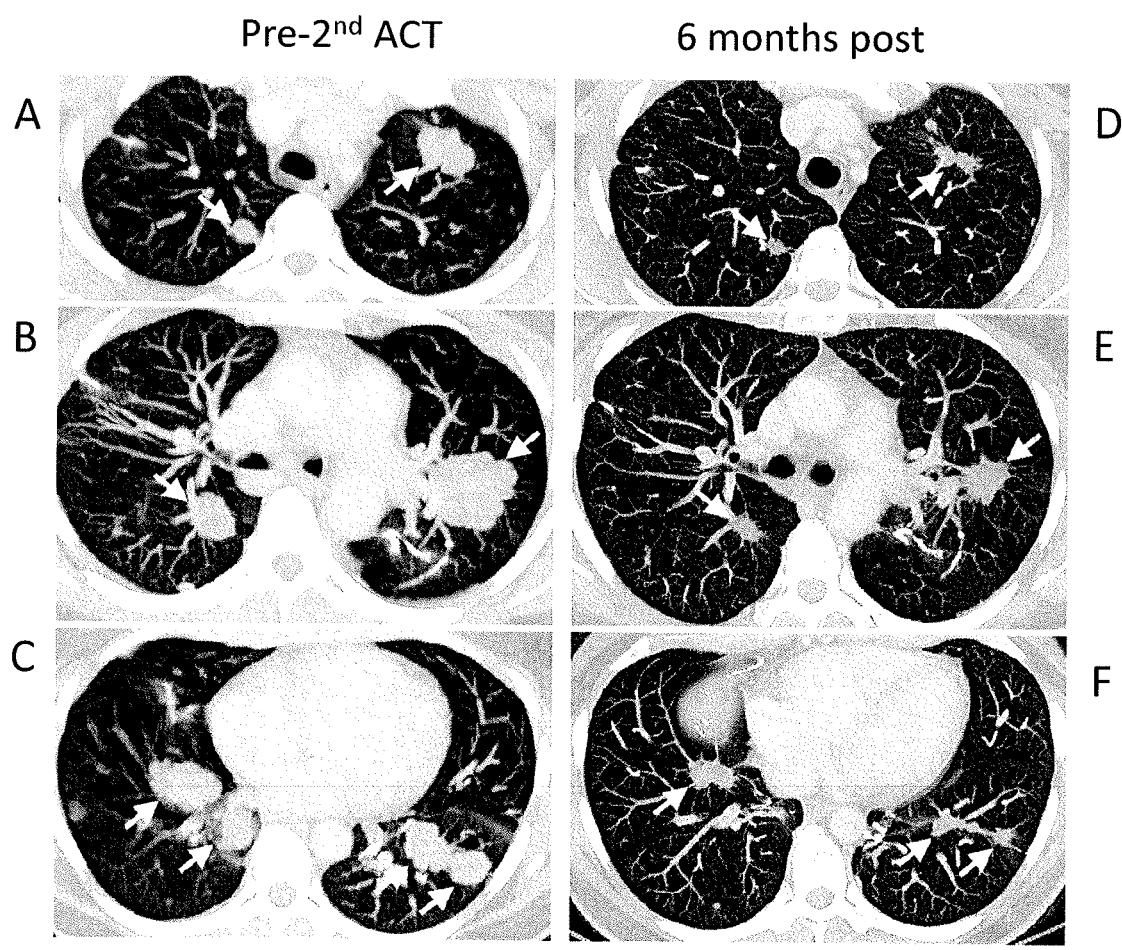

Six months after the second administration of mutation-reactive cells, computerized tomography (CT) scans of the lungs of Patient 3737 were taken, and the resulting images are shown in FIGS. 7A-C. These images were compared to those taken prior to the second administration of mutation-reactive cells (FIGS. 7D-7F). As shown in FIGS. 7A-7F, an approximately 36% decrease in cancerous lesions was observed which provided a partial response (PR) by Response Evaluation Criteria In Solid Tumors (RECIST) criteria.

Eight months after the second administration of mutation-reactive cells, positron emission tomography (PET) scans of the liver and lungs of Patient 3737 were taken. It was observed that the target lesions continued to shrink. The radio-labeled glucose analogue, FDG (fluorodeoxyglucose), was administered to assess the uptake of glucose by the tumors in order to measure the metabolic activity of the tumors. The PET scans demonstrated no glucose uptake in 2 liver lesions and only some uptake in lung lesions.

Examples 8-10

The materials and methods for Examples 8-10 are set forth below.
Patient Materials and Cell Lines All patient materials were obtained in the course of a National Cancer Institute Institutional Review Board approved clinical trial. Patient 2359 and Patient 2591 were enrolled in clinical trials (Trial registration ID: NCT00096382 and ID: NCT00335127, respectively) that have been described in Dudley et al., *J. Clin. Oncol.*, 26: 5233-9 (2008). The patients underwent resections from which both a TIL line and a tumor cell line were established. TILs used for this study were generated by methods described in Dudley et al., *J. Immunother.*, 26: 332-42 (2003). Briefly, tumor fragments were excised and cultured in media containing IL-2. The numbers of TIL cultures that expanded were screened for recognition of autologous or HLA-matched tumor, and the numbers of reactive TILs were expanded using a rapid expansion protocol (REP) with IL-2, anti-CD3 antibody and irradiated feeder cells to large numbers for patient infusion (Riddell et al., *Science*, 257: 238-41 (1992)). A small portion of TILs underwent a second REP. For co-culture assays, T cells and tumor cells were cultured at 1:1 ratio in a 96-well plate with 200 μL medium (AIM-V medium supplemented with 5% human serum) for 16 hours (hr).

To evaluate the antigen reactivity of TIL with clinical activity, two metastatic melanoma patients who experienced durable complete responses to adoptive TIL therapy were studied. Patient 2359 had a primary cutaneous melanoma at the right knee that metastasized to the thigh, iliac and inguinal lymph nodes. This individual experienced a complete regression of all metastatic lesions in response to autologous TIL transfer that was ongoing for over eight years following treatment. Patient 2591 had a primary back melanoma that metastasized to the abdominal wall, mesenteric lymph nodes, right colon, and supraclavicular lymph nodes. This individual experienced a complete regression of all metastatic lesions in response to autologous TIL transfer and remained disease free nine years after treatment.
Whole-Exome Sequencing The method has been described in Robbins et al., *Nat. Med.*, 19: 747-52 (2013). Genomic DNA purification, library construction, exome capture of approximately 20,000 coding genes and next-generation sequencing of tumor and normal samples were performed at Personal Genome Diagnostics (Baltimore, Md.). In brief, genomic DNA from tumor and normal samples was fragmented and used for Illumina TRUSEQ library construction (Illumina, San Diego, Calif.). Exonic regions were captured in solution using the Agilent SURESELECT 50 Mb kit (version 3) according to the manufacturer's instructions (Agilent, Santa Clara, Calif.). Paired-end sequencing, resulting in 100 bases from each end of each fragment, was performed using a HISEQ 2000 Genome Analyzer (Illumina). Sequence data were mapped to the reference human genome sequence, and sequence alterations were determined by comparison of over 50 million bases of tumor and normal DNA. Over 8 billion bases of sequence data were obtained for each sample, and a high fraction of the bases were from the captured coding regions. Over 43 million bases of target DNA were analyzed in the tumor and normal samples, and an average of 42-51 reads were obtained at each base in the normal and tumor DNA samples.

Bioinformatic analyses were carried out by Personal Genome Diagnostics and the Genome Technology Access Center, Genomics and Pathology Services of the Washington University School of Medicine. The tags were aligned to the human genome reference sequence (hg18) using the ELAND algorithm of the CASAVA 1.6 software (Illumina). The chastity filter of the BASECALL software of Illumina was used to select sequence reads for subsequent analyses. The ELANDv2 algorithm of the CASAVA 1.6 software was then applied to identify point mutations and small insertions and deletions. Known polymorphisms recorded in dbSNP were removed from the analysis. Potential somatic mutations were filtered and visually inspected as described in Jones et al., *Science*, 330: 228-31 (2010).

The Construction of Tandem Minigene Library

Non-synonymous mutations from melanoma samples were identified from whole-exome sequencing data. Tandem minigene constructs that encode polypeptides containing 6 identified mutated amino acid residues flanked on their N- and C-termini, 12 amino acids on both sides, were synthesized (Integrated DNA Technologies, Coralville, Iowa), and then cloned into pcDNA3.1 expression vector using the IN-FUSION Advantage PCR Cloning Kit (Clontech), according to the manufacturer's instructions.

IFN-γ ELISPOT Assay

The responses directed against tumor cell lines and peptide-pulsed target cells were quantified in an IFN-γ ELISPOT assay using 96-well PVDF-membrane filter plates (EMD Millipore, Billerica, Mass.) coated with 15 μg/ml of the monoclonal anti-IFN-γ antibody 1D1K (Mabtech, Inc., Cincinnati, Ohio). Bound cytokine was detected using 1 μg/ml of the biotinylated anti-IFN-γ antibody 7-B6-1 (Mabtech). HEK293 cells expressing HLA-A*0201, HLA-A*0205 or HLA-C*0701 were pulsed with peptides for 2 h at 37° C. The following peptides were used: MART-1: AAGIGILTV (SEQ ID NO: 54), mutated KIF2C: RLFPGLTIKI (SEQ ID NO: 55), mutated POLA2: TRSSGSHFVF (SEQ ID NO: 56). T cells were co-cultured overnight with target cells or medium containing 50 ng/ml PMA plus 1 μM ionomycin (PMA/I). The numbers of spots per $10^5$ T cells were calculated.

Example 8

This example demonstrates that TIL 2359 recognize a mutated antigen as assessed by minigene library screening.

The reactivity of TIL 2359 was evaluated using TMG constructs that were generated based on the non-synonymous mutations identified by exomic analysis of tumor and normal DNA. Each TMG construct encoded up to six individual minigene fragments that corresponded to the mutated codon flanked on either side by the 12 additional codons present in the normal gene product. One example is illustrated in FIG. 5A.

COS-7 cells were transiently transfected individually with one of twelve tandem minigenes encoding the 71 minigenes based on exomic DNA sequences containing non-synonymous point mutations identified from Mel 2359. These COS-7 cells were also co-transfected with HLA-A*0205, the dominant HLA restriction element used for autologous tumor cell recognition by this TIL. Co-culture of these transfectants with TIL 2359 resulted in the recognition of one of the 12 TMG constructs, RJ-1 (FIG. 5B). RJ-1 encoded mutated fragments of the EPHB2, KIF2C, SLC44A5, ABCA4, DENND4B, and EPRS genes, as shown in FIG. 5A. Subsequently, six RJ-1 variant constructs were generated, each of which encoded the WT rather than the mutated residue present in one of the six minigenes (FIG. 5C). TIL 2359 recognized COS-7 cells co-transfected with HLA-A*0205 plus five of the six individually transfected RJ-1 variants, but failed to recognize the variant encoding the WT KIF2C sequence, indicating that this minigene encoded a mutated epitope recognized by TIL 2359 (FIG. 5C). To further test this observation, COS-7 cells were co-transfected with either WT or mutated full-length KIF2C cDNA transcripts that were amplified from Mel 2359, together with either HLA-A*0101, HLA-A*0201 or HLA-A*0205 cDNA. The co-culture experiment indicated that TIL 2359 T cells recognized COS-7 cells co-transfected with the mutated but not WT KIF2C gene product, in a HLA-A*0205-restricted manner (FIG. 5D).

The mutated KIF2C coding region contained a single C to A transversion at nucleotide 46 that resulted in a substitution of threonine for alanine at position 16 in the native KIF2C protein. Exomic sequencing results indicated that DNA from Mel 2359 exclusively corresponded to the mutated but not the normal residue at position 46, results confirmed by direct Sanger sequencing of Mel 2359 DNA, indicating the loss of heterozygosity at this locus. In an attempt to identify the mutated KIF2C epitope recognized by TIL 2359, peptides encompassing the KIF2C mutation that were predicted to bind with high affinity to HLA-A*0205 were synthesized (Hoof et al., Immunogenetics, 61: 1-13 (2009)), and pulsed on HEK293 cells that stably expressed HLA-A*0205 (Table 21). HEK293-A*0205 cells pulsed with a decamer corresponding to residues 10-19 stimulated the release of high levels of IFN-γ from TIL 2359 T cells, and the peptide was recognized at a minimum concentration of 0.1 nM. In contrast, the corresponding WT peptide did not induce significant IFN-γ release at a concentration as high as 10 μM (FIG. 5E).

TABLE 21

| Amino acid position | Mutated Peptide | Predicted HLA-A*0205 binding affinity (nM) | Co-culture result [IFN-γ (pg/mL)] |
|---|---|---|---|
| 10-19 | RLFPGLTIKI (SEQ ID NO: 59) | 55.21 | 10690 |
| 10-17 | RLFPGLTI (SEQ ID NO: 60) | 132.35 | 121.5 |
| 15-25 | LTIKIQRSNGL (SEQ ID NO: 61) | 251.33 | 31.5 |
| 7-17 | LQARLFPGLTI (SEQ ID NO: 62) | 293.83 | 27 |
| 7-16 | LQARLFPGLT (SEQ ID NO: 63) | 1549.33 | 24 |

Example 9

This example demonstrates that TIL 2591 recognize a mutated antigen identified by minigene library screening.

The mutated T-cell antigen recognized by TIL 2591 was identified by synthesizing 37 TMG constructs encoding the 217 minigenes based on exomic DNA sequences containing non-synonymous point mutations identified from Mel 2591.

TIL 2591 recognized autologous tumor cells in the context of multiple HLA restriction elements. Therefore, HEK293 cell lines stably expressing each of the six MHC class I HLA molecules isolated from Mel 2591 were transiently transfected individually with the 37 TMG constructs, followed by an overnight co-culture with TIL 2591. Initial results indicated that TIL 2591 recognized HLA-C*0701+ HEK293 cells (HEK293-C*0701) cells that were transiently transfected with minigene DW-6, but failed to respond significantly to the other minigene constructs (FIG. 6A). Each of the six individual mutated minigenes in the DW-6 tandem construct (FIG. 6B) were then individually reverted to the WT sequence (FIG. 6C). Evaluation of responses to the WT variants indicated that TIL 2591 recognized COS-7 cells transfected with each of the DW-6 variants, with the exception of a construct encoding the WT POLA2 fragment (FIG. 6C). To test these findings, COS-7 cells were transfected with either a WT or mutated full-length POLA2 cDNA construct, together with HLA-C*0401, HLA-C*0701 or HLA-C*0702 cDNA. TIL 2591 T cells only recognized target cells transfected with HLA-C*0701 plus the mutated POLA2 construct, but not the corresponding WT transcript (FIG. 6D). The single C to T transition at nucleotide 1258 of the POLA2 coding region resulted in a substitution of leucine for phenylalanine at position 420 of the WT POLA2 protein. Sanger sequencing indicated that both genomic DNA and cDNA derived from Mel 2591 RNA contained both the WT and mutated nucleotide at position 1258, whereas genomic DNA isolated from PBMC of patient 2591 corresponded to the WT sequence, indicating that this represented a heterozygous somatic mutation in Mel 2591 cells.

An HLA-C*0701 binding algorithm was then used to identify candidate POLA2 peptides overlapping with the mutated leucine residue at position 420 (Table 22). Co-culture results indicated that HLA-C*0701+ HEK293 cells pulsed with a decamer corresponding to residues 413-422 of mutated POLA2 stimulated the release of IFN-γ from TIL 2591 T cells at a minimum concentration of 10 nM. In contrast, the corresponding WT peptide did not induce significant IFN-γ release at a concentration as high as 10 μM (FIG. 6E).

melanoma (Table 23). TIL 2591 generated greater than 7,000 spots in response to the HLA-A2 restricted MART-1 epitope, while only small fractions of T cells reacted against the HLA-C*0701-restricted mutated POLA2 epitope (Table 23).

TABLE 23

| | TIL 2359 Spots per 1 × 10⁵ cells |
|---|---|
| Mel 2359 | 1698 |
| 293-A*0205 | 189 |
| 293-A*0205 + KIF2C mut | 2057 |
| | TIL 2591 Spots per 1 × 10⁵ cells |
| Mel 2591 | 11344 |
| 293-A*02 | 999 |
| 293-A*02 + MART-1 | 7404 |
| 293-C*0701 | 906 |
| 293-C*0701 + POLA2 mut | 1280 |

Example 10

This example demonstrates a method of identifying T cells reactive against a mutated antigen present in gastrointestinal (GI) cancer identified by minigene library screening.

Whole-exome sequencing was performed on metastatic lesions from GI cancer patients to identify mutations. Next, minigene constructs that encoded each mutation were generated and transfected into autologous APCs to allow for the processing and presentation of all the mutations expressed by the tumor. These APCs were then co-cultured with tumor infiltrating lymphocytes (TIL) and T-cell reactivity against the mutations was determined by IFN-γ ELISPOT and 4-1BB and OX40 upregulation by flow cytometry.

In one patient with colon cancer, 119 mutations were evaluated for mutation-reactivity. Several, but not all, TIL cultures were found to contain highly variable proportions of CD8+ T cells that specifically recognized a mutation in

TABLE 22

| Amino acid position | Mutated Peptide | Predicted HLA-C*0701 binding affinity (nM) | Co-culture result [IFN-γ (pg/mL)] |
|---|---|---|---|
| 413-422 | TRSSGSHFVF (SEQ ID NO: 68) | 147.35 | 1106 |
| 413-423 | TRSSGSHFVFV (SEQ ID NO: 69) | 280.38 | 50 |
| 413-421 | TRSSGSHFV (SEQ ID NO: 70) | 285.90 | 60 |
| 413-420 | TRSSGSHF (SEQ ID NO: 71) | 518.82 | 48 |
| 420-429 | FVFVPSLRDV (SEQ ID NO: 72) | 599.44 | 39 |

The proportion of T cells in TIL 2359 and 2591 recognizing the mutated KIF2C and POLA2, respectively, was then estimated using IFN-γ enzyme-linked immunosorbent spot (ELISPOT) assays. TIL 2359 generated approximately 2,000 spots per 100,000 T cells in response to HLA-A*0205+ cells pulsed with the mutated KIF2C epitope, similar to that observed in response to the autologous CASP8 (67 F→V). Upon further expansion in vitro, these mutation-reactive CD8+ T cells were markedly outgrown by other cells in culture. Administration of 40.3×10⁹ TIL, which was estimated to contain about 0.31% (approximately 127 million) mutation-reactive cells, to the patient did not result in a clinical response at the first follow-up approximately six weeks after administration of cells. The patient died about six weeks later. Without being bound to a particular theory or mechanism, it is believed that any one or more of the very late stage of the disease prior to treatment, the patient's poor overall condition, and the patient's poor tolerance of the lymphodepleting chemotherapy administered prior to adoptive cell therapy may have been contributing factors in the patient's death. A TCR that was reactive against mutated CASP8 was isolated from the TIL, and T cells transduced to express the TCR were reactive against DCs pulsed with mutated CASP8.

In another patient with rectal cancer, 155 mutations were evaluated for mutation-reactivity. At least 3 different mutation-reactivities were found, two comprising CD8+ T-cell responses and one CD4+ response. Administration of mutation-reactive TIL to the patient initially resulted in a mixed response at approximately 1.5 months after treatment, but the patient later developed progressive disease at approximately 3.5 months after treatment. A potentially mutation-reactive TCR was isolated from the CD4+ TIL and from the CD8+ TIL.

In a third patient (cholangiocarcinoma), T cells reactive against 38 mutations tested were not detected. For this patient, the "mutation call" threshold was lowered, and an additional 125 putative mutations will be evaluated. The "mutation call" is an arbitrarily set threshold at which a sequence is identified as a mutation using bioinformatics. In this case, as a first pass, the threshold was relatively high (for example, providing a high level of confidence that the mutations identified were true mutations). The threshold was then lowered, providing a lower level of confidence that the mutations identified were true mutations, however, the possibility that the mutations identified were true mutations remained.

These data show that the ability of the human immune system to mount a T-cell response against somatic mutations in metastatic GI cancers may not be a rare event. The study is ongoing.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of isolating T cells having antigenic specificity for mutated amino acid sequences encoded by cancer-specific mutations, the method comprising:
- identifying more than one gene in the nucleic acid of tumor cells of a patient, each gene containing one of a cancer-specific mutation that encodes a mutated amino acid sequence;
- separately inducing autologous antigen presenting cells (APCs) of the patient to present the mutated amino acid sequence for each of the more than one identified genes;
- obtaining separate cultures of autologous T cells from multiple fragments of the patient's tumor;
- separately co-culturing each of the APCs presenting a mutated amino acid sequence with each of the separate cultures of autologous T cells
- assessing each co-culture for autologous T cells having antigenic specificity for the mutated amino acid sequence presented in the context of an MHC class I molecule of the patient;
- assessing each co-culture for autologous T cells having antigenic specificity for the mutated amino acid sequence presented in the context of an MHC class II molecule of the patient;
- selecting the autologous T cells having antigenic specificity for a mutated amino acid sequence presented in the context of major histocompatibility complex (MHC) molecule(s) expressed by the patient and
- isolating the selected autologous T cells.

2. The method according to claim 1, further comprising separating the selected autologous T cells from autologous T cells that do not have antigenic specificity for the mutated amino acid sequence.

3. The method of claim 1, wherein inducing autologous APCs of the patient to present the mutated amino acid sequences comprises pulsing APCs with peptides comprising the mutated amino acid sequences or a pool of peptides, each peptide in the pool comprising a different one of the mutated amino acid sequences.

4. The method of claim 1, wherein inducing autologous APCs of the patient to present the mutated amino acid sequences comprises introducing a nucleotide sequence encoding the mutated amino acid sequences into the APCs.

5. The method of claim 4,
- wherein the nucleotide sequence introduced into the autologous APCs is a tandem gene sequence construct, each gene sequence comprising a nucleotide sequence of a different gene, each gene sequence including one of the cancer-specific mutations that encodes one of the mutated amino acid sequences.

6. The method of claim 1, wherein selecting the autologous T cells that have antigenic specificity for a mutated amino acid sequence comprises selectively growing the autologous T cells that have antigenic specificity for a mutated amino acid sequence.

7. The method of claim 1, wherein selecting the autologous T cells that have antigenic specificity for a mutated amino acid sequence comprises selecting T cells that express any one or more of programmed cell death 1 (PD-1), lymphocyte-activation gene 3 (LAG-3), T cell immunoglobulin and mucin domain 3 (TIM-3), 4-1BB, OX40, and CD107a.

8. The method of claim 1, wherein selecting the autologous T cells that have antigenic specificity for a mutated amino acid sequence comprises selecting T cells
- (i) that secrete a greater amount of one or more cytokines upon culture with the APCs that present the mutated amino acid sequences as compared to the amount of the one or more cytokines secreted by negative control T cells, or
- (ii) in which at least twice the number of T cells secrete one or more cytokines upon co-culture with the APCs that present the mutated amino acid sequences as compared to the number of negative control T cells secreting one or more cytokines.

9. The method of claim 8, wherein the one or more cytokines comprise interferon (IFN)-γ, interleukin (IL)-2, tumor necrosis factor alpha (TNF-α), granulocyte/monocyte colony stimulating factor (GM-CSF), IL-4, IL-5, IL-9, IL-10, IL-17, and IL-22.

10. The method of claim 1, wherein identifying more than one gene in the nucleic acid of tumor cells comprises sequencing the whole exome, the whole genome, or the whole transcriptome of the tumor cells.

11. A method of preparing a population of T cells that have antigenic specificity for a mutated amino acid sequence encoded by a cancer specific mutation, the method comprising:
- isolating T cells according to the method of claim 1, and
- expanding the isolated T cells to obtain a population of T cells that have antigenic specificity for a mutated amino acid sequence encoded by a cancer-specific mutation.

12. The method of claim 11, wherein expanding the numbers of cells comprises culturing the selected cells with feeder PBMC, interleukin (IL)-2, and OKT3 antibody.

13. A method of treating a tumor in a patient, the method comprising:
- administering to the patient a population of T cells prepared according to the method of claim 11 in an amount effective to treat the tumor in the patient, wherein the T cells administered to the patient are autologous to the patient and have antigenic specificity for a mutated amino acid sequence expressed by the tumor in the patient.

14. The method according to claim 13, wherein the tumor is an epithelial cancer.

15. The method according to claim 13, wherein the tumor is cholangiocarcinoma, melanoma, colon cancer or rectal cancer.

\* \* \* \* \*

UNITED STATES PATENT AND TRADEMARK OFFICE
CERTIFICATE OF CORRECTION

PATENT NO. : 10,973,894 B2
APPLICATION NO. : 15/515055
DATED : April 13, 2021
INVENTOR(S) : Tran et al.

Page 1 of 1

It is certified that error appears in the above-identified patent and that said Letters Patent is hereby corrected as shown below:

In the Claims

Column 77, Line 13:
The words "one of" should be deleted from Claim 1.

Signed and Sealed this
Twentieth Day of July, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 73

<210> SEQ ID NO 1
<211> LENGTH: 25
<212> TYPE: PRT
<213> ORGANISM: Artificial Sequence
<220> FEATURE:
<223> OTHER INFORMATION: Synthetic

<400> SEQUENCE: 1

Arg Val Leu Lys Gly Gly Ser Val Arg Lys Leu Arg His Ala Lys Gln
1               5                   10                  15

Leu Val Leu Glu Leu Gly Glu Glu Ala
            20                  25

<210> SEQ ID NO 2
<211> LENGTH: 25
<212> TYPE: PRT
<213> ORGANISM: Artificial Sequence
<220> FEATURE:
<223> OTHER INFORMATION: Synthetic
```

-continued

<400> SEQUENCE: 2

Gln Asn Ala Ala Asp Ser Tyr Ser Trp Val Pro Glu Gln Ala Glu Ser
1               5                   10                  15

Arg Ala Met Glu Asn Gln Tyr Ser Pro
            20                  25

<210> SEQ ID NO 3
<211> LENGTH: 25
<212> TYPE: PRT
<213> ORGANISM: Artificial Sequence
<220> FEATURE:
<223> OTHER INFORMATION: Synthetic

<400> SEQUENCE: 3

Thr Ser Phe Leu Ser Ile Asn Ser Lys Glu Glu Thr Gly His Leu Glu
1               5                   10                  15

Asn Gly Asn Lys Tyr Pro Asn Leu Glu
            20                  25

<210> SEQ ID NO 4
<211> LENGTH: 25
<212> TYPE: PRT
<213> ORGANISM: Artificial Sequence
<220> FEATURE:
<223> OTHER INFORMATION: Synthetic

<400> SEQUENCE: 4

Phe Ile Pro Leu Leu Val Val Ile Leu Phe Ala Val His Thr Gly Leu
1               5                   10                  15

Phe Ile Ser Thr Gln Gln Gln Val Thr
            20                  25

<210> SEQ ID NO 5
<211> LENGTH: 25
<212> TYPE: PRT
<213> ORGANISM: Artificial Sequence
<220> FEATURE:
<223> OTHER INFORMATION: Synthetic

<400> SEQUENCE: 5

Glu Ser Asp Arg Pro Arg Lys Val Arg Phe Arg Ile Val Ser Ser His
1               5                   10                  15

Ser Gly Arg Val Leu Lys Glu Val Tyr
            20                  25

<210> SEQ ID NO 6
<211> LENGTH: 25
<212> TYPE: PRT
<213> ORGANISM: Artificial Sequence
<220> FEATURE:
<223> OTHER INFORMATION: Synthetic

<400> SEQUENCE: 6

Glu Ile Tyr Asn Glu Ser Leu Phe Asp Leu Leu Ser Ala Leu Pro Tyr
1               5                   10                  15

Val Gly Pro Ser Val Thr Pro Met Thr
            20                  25

<210> SEQ ID NO 7
<211> LENGTH: 25
<212> TYPE: PRT
<213> ORGANISM: Artificial Sequence
<220> FEATURE:

<223> OTHER INFORMATION: Synthetic

<400> SEQUENCE: 7

Gly Lys Lys Leu Arg Asp Asp Tyr Leu Ala Ser Leu His Pro Arg Leu
1               5                   10                  15

His Ser Ile Tyr Val Ser Glu Gly Tyr
            20                  25

<210> SEQ ID NO 8
<211> LENGTH: 25
<212> TYPE: PRT
<213> ORGANISM: Artificial Sequence
<220> FEATURE:
<223> OTHER INFORMATION: Synthetic

<400> SEQUENCE: 8

Pro Asp Ile Lys Gln Glu Leu Leu Arg Cys Asp Ile Ile Cys Lys Gly
1               5                   10                  15

Gly His Ser Thr Val Thr Asp Leu Gln
            20                  25

<210> SEQ ID NO 9
<211> LENGTH: 25
<212> TYPE: PRT
<213> ORGANISM: Artificial Sequence
<220> FEATURE:
<223> OTHER INFORMATION: Synthetic

<400> SEQUENCE: 9

Val Gly Thr Lys Leu Asp Leu Arg Asp Lys Asp Asn Ile Glu Arg
1               5                   10                  15

Leu Arg Asp Lys Lys Leu Ala Pro Ile
            20                  25

<210> SEQ ID NO 10
<211> LENGTH: 25
<212> TYPE: PRT
<213> ORGANISM: Artificial Sequence
<220> FEATURE:
<223> OTHER INFORMATION: Synthetic

<400> SEQUENCE: 10

Val Lys Leu Leu Gly Ile His Cys Gln Asn Ala Ala Ile Thr Glu Met
1               5                   10                  15

Cys Leu Val Ala Phe Gly Asn Leu Ala
            20                  25

<210> SEQ ID NO 11
<211> LENGTH: 25
<212> TYPE: PRT
<213> ORGANISM: Artificial Sequence
<220> FEATURE:
<223> OTHER INFORMATION: Synthetic

<400> SEQUENCE: 11

Asn Leu Arg Lys Ser Ser Pro Gly Thr Ser Asn Lys Cys Leu Arg Gln
1               5                   10                  15

Val Ser Ser Leu Val Leu His Ile Glu
            20                  25

<210> SEQ ID NO 12
<211> LENGTH: 25
<212> TYPE: PRT
<213> ORGANISM: Artificial Sequence
<220> FEATURE:
<223> OTHER INFORMATION: Synthetic

<400> SEQUENCE: 12

Leu Gly Arg Leu His Pro Cys Val Met Ala Ser Leu Lys Ala Gln Ser
1               5                   10                  15

Pro Ile Pro Asn Leu Tyr Leu Thr Gly
            20                  25

<210> SEQ ID NO 13
<211> LENGTH: 25
<212> TYPE: PRT
<213> ORGANISM: Artificial Sequence
<220> FEATURE:
<223> OTHER INFORMATION: Synthetic

<400> SEQUENCE: 13

Leu Leu Pro Ile His Thr Leu Asp Val Lys Ser Thr Thr Leu Pro Ala
1               5                   10                  15

Ala Val Arg Cys Ser Glu Ser Arg Leu
            20                  25

<210> SEQ ID NO 14
<211> LENGTH: 25
<212> TYPE: PRT
<213> ORGANISM: Artificial Sequence
<220> FEATURE:
<223> OTHER INFORMATION: Synthetic

<400> SEQUENCE: 14

Met Thr Met Asp Asn Phe Gly Lys His Tyr Thr Leu Lys Ser Glu Ala
1               5                   10                  15

Pro Leu Tyr Val Gly Gly Met Pro Val
            20                  25

<210> SEQ ID NO 15
<211> LENGTH: 25
<212> TYPE: PRT
<213> ORGANISM: Artificial Sequence
<220> FEATURE:
<223> OTHER INFORMATION: Synthetic

<400> SEQUENCE: 15

Ala Val Asp Val Glu Gly Met Lys Thr Gln Tyr Ser Val Lys Gln Arg
1               5                   10                  15

Thr Glu Asn Val Leu Arg Ile Phe Leu
            20                  25

<210> SEQ ID NO 16
<211> LENGTH: 25
<212> TYPE: PRT
<213> ORGANISM: Artificial Sequence
<220> FEATURE:
<223> OTHER INFORMATION: Synthetic

<400> SEQUENCE: 16

His Asp Gly Pro Phe Val Phe Ala Glu Val Asn Ala Asn Tyr Ile Thr
1               5                   10                  15

Trp Leu Trp His Glu Asp Glu Ser Arg
            20                  25

<210> SEQ ID NO 17
<211> LENGTH: 25
<212> TYPE: PRT

```
<213> ORGANISM: Artificial Sequence
<220> FEATURE:
<223> OTHER INFORMATION: Synthetic

<400> SEQUENCE: 17

Gln Ala Lys Glu Asp Phe Ser Gly Tyr Asp Phe Glu Thr Arg Leu His
1               5                   10                  15

Val Arg Ile His Ala Ala Leu Ala Ser
            20                  25

<210> SEQ ID NO 18
<211> LENGTH: 25
<212> TYPE: PRT
<213> ORGANISM: Artificial Sequence
<220> FEATURE:
<223> OTHER INFORMATION: Synthetic

<400> SEQUENCE: 18

Pro Ala Val Arg Pro Gly Ile Cys Pro Gly Pro Asp Gly Trp Arg Ile
1               5                   10                  15

Pro Leu Gly Pro Leu Pro His Glu Phe
            20                  25

<210> SEQ ID NO 19
<211> LENGTH: 25
<212> TYPE: PRT
<213> ORGANISM: Artificial Sequence
<220> FEATURE:
<223> OTHER INFORMATION: Synthetic

<400> SEQUENCE: 19

Val Ala Gln Glu Leu Phe Gln Gly Ser Asp Leu Gly Val Ala Glu Glu
1               5                   10                  15

Ala Glu Arg Pro Gly Glu Lys Ala Gly
            20                  25

<210> SEQ ID NO 20
<211> LENGTH: 15
<212> TYPE: PRT
<213> ORGANISM: Artificial Sequence
<220> FEATURE:
<223> OTHER INFORMATION: Synthetic

<400> SEQUENCE: 20

Gly Thr Ala Thr Thr Leu Thr Asp Leu Thr Asn Pro Leu Ser Leu
1               5                   10                  15

<210> SEQ ID NO 21
<211> LENGTH: 45
<212> TYPE: PRT
<213> ORGANISM: Artificial Sequence
<220> FEATURE:
<223> OTHER INFORMATION: Synthetic

<400> SEQUENCE: 21

Thr His Ile Arg Arg Ile Val Pro Gly Ala Val Ser Asp Gly Arg Met
1               5                   10                  15

Gly Ser Trp Arg Ala Pro Pro Thr Leu Ser Val Pro Ala Ser Pro Leu
            20                  25                  30

Thr Leu Leu Gln Ser His Phe Arg Gln Gln Ala Arg Val
        35                  40                  45

<210> SEQ ID NO 22
<211> LENGTH: 40
```

```
<212> TYPE: PRT
<213> ORGANISM: Artificial Sequence
<220> FEATURE:
<223> OTHER INFORMATION: Synthetic

<400> SEQUENCE: 22

Arg His Leu Ser Gln Glu Phe Gly Trp Leu Gln Ile Thr Pro Pro Gly
1               5                   10                  15

Ile Pro Val His Glu Ser Thr Ala Thr Leu Gln His Tyr Ser Ser Gly
            20                  25                  30

Trp Ala Glu Lys Ser Lys Ile Leu
        35                  40

<210> SEQ ID NO 23
<211> LENGTH: 44
<212> TYPE: PRT
<213> ORGANISM: Artificial Sequence
<220> FEATURE:
<223> OTHER INFORMATION: Synthetic

<400> SEQUENCE: 23

Ser Pro Asp Ser Lys Ile Gln Met Val Ser Ser Gln Lys Arg Ala
1               5                   10                  15

Leu Leu Cys Leu Ile Ala Leu Leu Ser Arg Lys Gln Thr Trp Lys Ile
            20                  25                  30

Arg Thr Cys Leu Arg Arg Val Arg Gln Lys Cys Phe
        35                  40

<210> SEQ ID NO 24
<211> LENGTH: 32
<212> TYPE: PRT
<213> ORGANISM: Artificial Sequence
<220> FEATURE:
<223> OTHER INFORMATION: Synthetic

<400> SEQUENCE: 24

Thr Leu Leu Ser Pro Gln Glu Ala Gly Ala Thr Lys Asp Glu Cys Glu
1               5                   10                  15

Gly Glu Glu Gly Ala Ala Gly Ser Arg Asp Leu Arg Ser Trp Val Thr
            20                  25                  30

<210> SEQ ID NO 25
<211> LENGTH: 67
<212> TYPE: PRT
<213> ORGANISM: Artificial Sequence
<220> FEATURE:
<223> OTHER INFORMATION: Synthetic

<400> SEQUENCE: 25

Glu Glu Thr Gly Met Pro Asn Lys Ala Ser Lys Gln Gly Pro Gly Ser
1               5                   10                  15

Thr Gln Arg Glu Gly Ser Leu Glu Glu Ile Pro Gly Leu Thr Asn Ile
            20                  25                  30

Tyr Lys Leu Leu Thr Ser Val Trp Gly Leu Leu Arg Leu Trp Val Trp
        35                  40                  45

Gly Pro Ala Leu Ala Phe Thr Ser Cys Val Thr Ser Glu Ile Ala Met
    50                  55                  60

Arg Leu Leu
65

<210> SEQ ID NO 26
<211> LENGTH: 225
```

```
<212> TYPE: PRT
<213> ORGANISM: Artificial Sequence
<220> FEATURE:
<223> OTHER INFORMATION: Synthetic

<400> SEQUENCE: 26

Arg Val Leu Lys Gly Gly Ser Val Arg Lys Leu Arg His Ala Lys Gln
1               5                   10                  15

Leu Val Leu Glu Leu Gly Glu Glu Ala Gln Asn Ala Ala Asp Ser Tyr
            20                  25                  30

Ser Trp Val Pro Glu Gln Ala Glu Ser Arg Ala Met Glu Asn Gln Tyr
        35                  40                  45

Ser Pro Thr Ser Phe Leu Ser Ile Asn Ser Lys Glu Glu Thr Gly His
    50                  55                  60

Leu Glu Asn Gly Asn Lys Tyr Pro Asn Leu Glu Phe Ile Pro Leu Leu
65                  70                  75                  80

Val Val Ile Leu Phe Ala Val His Thr Gly Leu Phe Ile Ser Thr Gln
                85                  90                  95

Gln Gln Val Thr Glu Ser Asp Arg Pro Arg Lys Val Arg Phe Arg Ile
            100                 105                 110

Val Ser Ser His Ser Gly Arg Val Leu Lys Glu Val Tyr Glu Ile Tyr
        115                 120                 125

Asn Glu Ser Leu Phe Asp Leu Leu Ser Ala Leu Pro Tyr Val Gly Pro
    130                 135                 140

Ser Val Thr Pro Met Thr Gly Lys Lys Leu Arg Asp Asp Tyr Leu Ala
145                 150                 155                 160

Ser Leu His Pro Arg Leu His Ser Ile Tyr Val Ser Glu Gly Tyr Pro
                165                 170                 175

Asp Ile Lys Gln Glu Leu Leu Arg Cys Asp Ile Ile Cys Lys Gly Gly
            180                 185                 190

His Ser Thr Val Thr Asp Leu Gln Val Gly Thr Lys Leu Asp Leu Arg
        195                 200                 205

Asp Asp Lys Asp Asn Ile Glu Arg Leu Arg Asp Lys Lys Leu Ala Pro
    210                 215                 220

Ile
225

<210> SEQ ID NO 27
<211> LENGTH: 225
<212> TYPE: PRT
<213> ORGANISM: Artificial Sequence
<220> FEATURE:
<223> OTHER INFORMATION: Synthetic

<400> SEQUENCE: 27

Val Lys Leu Leu Gly Ile His Cys Gln Asn Ala Ala Ile Thr Glu Met
1               5                   10                  15

Cys Leu Val Ala Phe Gly Asn Leu Ala Asn Leu Arg Lys Ser Ser Pro
            20                  25                  30

Gly Thr Ser Asn Lys Cys Leu Arg Gln Val Ser Ser Leu Val Leu His
        35                  40                  45

Ile Glu Leu Gly Arg Leu His Pro Cys Val Met Ala Ser Leu Lys Ala
    50                  55                  60

Gln Ser Pro Ile Pro Asn Leu Tyr Leu Thr Gly Leu Leu Pro Ile His
65                  70                  75                  80

Thr Leu Asp Val Lys Ser Thr Thr Leu Pro Ala Ala Val Arg Cys Ser
                85                  90                  95
```

Glu Ser Arg Leu Met Thr Met Asp Asn Phe Gly Lys His Tyr Thr Leu
            100                 105                 110

Lys Ser Glu Ala Pro Leu Tyr Val Gly Met Pro Val Met Thr Met
        115                 120                 125

Asp Asn Phe Gly Lys His Tyr Thr Leu Lys Ser Glu Ala Pro Leu Tyr
    130                 135                 140

Val Gly Met Pro Val His Asp Gly Pro Phe Val Phe Ala Glu Val
145                 150                 155                 160

Asn Ala Asn Tyr Ile Thr Trp Leu Trp His Glu Asp Glu Ser Arg Gln
                165                 170                 175

Ala Lys Glu Asp Phe Ser Gly Tyr Asp Phe Glu Thr Arg Leu His Val
            180                 185                 190

Arg Ile His Ala Ala Leu Ala Ser Pro Ala Val Arg Pro Gly Ile Cys
        195                 200                 205

Pro Gly Pro Asp Gly Trp Arg Ile Pro Leu Gly Pro Leu Pro His Glu
    210                 215                 220

Phe
225

<210> SEQ ID NO 28
<211> LENGTH: 268
<212> TYPE: PRT
<213> ORGANISM: Artificial Sequence
<220> FEATURE:
<223> OTHER INFORMATION: Synthetic

<400> SEQUENCE: 28

Val Ala Gln Glu Leu Phe Gln Gly Ser Asp Leu Gly Val Ala Glu Glu
1               5                   10                  15

Ala Glu Arg Pro Gly Glu Lys Ala Gly Gly Thr Ala Thr Thr Leu Thr
            20                  25                  30

Asp Leu Thr Asn Pro Leu Ser Leu Thr His Ile Arg Arg Ile Val Pro
        35                  40                  45

Gly Ala Val Ser Asp Gly Arg Met Gly Ser Trp Arg Ala Pro Pro Thr
    50                  55                  60

Leu Ser Val Pro Ala Ser Pro Leu Thr Leu Leu Gln Ser His Phe Arg
65                  70                  75                  80

Gln Gln Ala Arg Val Arg His Leu Ser Gln Glu Phe Gly Trp Leu Gln
                85                  90                  95

Ile Thr Pro Pro Gly Ile Pro Val His Glu Ser Thr Ala Thr Leu Gln
            100                 105                 110

His Tyr Ser Ser Gly Trp Ala Glu Lys Ser Lys Ile Leu Ser Pro Asp
        115                 120                 125

Ser Lys Ile Gln Met Val Ser Ser Gln Lys Arg Ala Leu Leu Cys
    130                 135                 140

Leu Ile Ala Leu Leu Ser Arg Lys Gln Thr Trp Lys Ile Arg Thr Cys
145                 150                 155                 160

Leu Arg Arg Val Arg Gln Lys Cys Phe Thr Leu Leu Ser Pro Gln Glu
                165                 170                 175

Ala Gly Ala Thr Lys Asp Glu Cys Glu Gly Glu Glu Gly Ala Ala Gly
            180                 185                 190

Ser Arg Asp Leu Arg Ser Trp Val Thr Glu Glu Thr Gly Met Pro Asn
        195                 200                 205

Lys Ala Ser Lys Gln Gly Pro Gly Ser Thr Gln Arg Glu Gly Ser Leu
    210                 215                 220

Glu Glu Ile Pro Gly Leu Thr Asn Ile Tyr Lys Leu Leu Thr Ser Val
225                 230                 235                 240

Trp Gly Leu Leu Arg Leu Trp Val Trp Gly Pro Ala Leu Ala Phe Thr
                245                 250                 255

Ser Cys Val Thr Ser Glu Ile Ala Met Arg Leu Leu
            260                 265

<210> SEQ ID NO 29
<211> LENGTH: 13
<212> TYPE: PRT
<213> ORGANISM: Artificial Sequence
<220> FEATURE:
<223> OTHER INFORMATION: Synthetic

<400> SEQUENCE: 29

Asn Ser Lys Glu Glu Thr Gly His Leu Glu Asn Gly Asn
1               5                   10

<210> SEQ ID NO 30
<211> LENGTH: 23
<212> TYPE: PRT
<213> ORGANISM: Artificial Sequence
<220> FEATURE:
<223> OTHER INFORMATION: Synthetic

<400> SEQUENCE: 30

Phe Leu Ser Ile Asn Ser Lys Glu Glu Thr Gly His Leu Glu Asn Gly
1               5                   10                  15

Asn Lys Tyr Pro Asn Leu Glu
            20

<210> SEQ ID NO 31
<211> LENGTH: 21
<212> TYPE: PRT
<213> ORGANISM: Artificial Sequence
<220> FEATURE:
<223> OTHER INFORMATION: Synthetic

<400> SEQUENCE: 31

Ser Ile Asn Ser Lys Glu Glu Thr Gly His Leu Glu Asn Gly Asn Lys
1               5                   10                  15

Tyr Pro Asn Leu Glu
            20

<210> SEQ ID NO 32
<211> LENGTH: 19
<212> TYPE: PRT
<213> ORGANISM: Artificial Sequence
<220> FEATURE:
<223> OTHER INFORMATION: Synthetic

<400> SEQUENCE: 32

Asn Ser Lys Glu Glu Thr Gly His Leu Glu Asn Gly Asn Lys Tyr Pro
1               5                   10                  15

Asn Leu Glu

<210> SEQ ID NO 33
<211> LENGTH: 17
<212> TYPE: PRT
<213> ORGANISM: Artificial Sequence
<220> FEATURE:
<223> OTHER INFORMATION: Synthetic

<400> SEQUENCE: 33

```
Lys Glu Glu Thr Gly His Leu Glu Asn Gly Asn Lys Tyr Pro Asn Leu
  1               5                  10                  15

Glu

<210> SEQ ID NO 34
<211> LENGTH: 15
<212> TYPE: PRT
<213> ORGANISM: Artificial Sequence
<220> FEATURE:
<223> OTHER INFORMATION: Synthetic

<400> SEQUENCE: 34

Thr Ser Phe Leu Ser Ile Asn Ser Lys Glu Glu Thr Gly His Leu
  1               5                  10                  15

<210> SEQ ID NO 35
<211> LENGTH: 17
<212> TYPE: PRT
<213> ORGANISM: Artificial Sequence
<220> FEATURE:
<223> OTHER INFORMATION: Synthetic

<400> SEQUENCE: 35

Thr Ser Phe Leu Ser Ile Asn Ser Lys Glu Glu Thr Gly His Leu Glu
  1               5                  10                  15

Asn

<210> SEQ ID NO 36
<211> LENGTH: 19
<212> TYPE: PRT
<213> ORGANISM: Artificial Sequence
<220> FEATURE:
<223> OTHER INFORMATION: Synthetic

<400> SEQUENCE: 36

Thr Ser Phe Leu Ser Ile Asn Ser Lys Glu Glu Thr Gly His Leu Glu
  1               5                  10                  15

Asn Gly Asn

<210> SEQ ID NO 37
<211> LENGTH: 21
<212> TYPE: PRT
<213> ORGANISM: Artificial Sequence
<220> FEATURE:
<223> OTHER INFORMATION: Synthetic

<400> SEQUENCE: 37

Thr Ser Phe Leu Ser Ile Asn Ser Lys Glu Glu Thr Gly His Leu Glu
  1               5                  10                  15

Asn Gly Asn Lys Tyr
              20

<210> SEQ ID NO 38
<211> LENGTH: 23
<212> TYPE: PRT
<213> ORGANISM: Artificial Sequence
<220> FEATURE:
<223> OTHER INFORMATION: Synthetic

<400> SEQUENCE: 38

Thr Ser Phe Leu Ser Ile Asn Ser Lys Glu Glu Thr Gly His Leu Glu
  1               5                  10                  15

Asn Gly Asn Lys Tyr Pro Asn
```

<210> SEQ ID NO 39
<211> LENGTH: 346
<212> TYPE: DNA
<213> ORGANISM: Artificial Sequence
<220> FEATURE:
<223> OTHER INFORMATION: Synthetic

<400> SEQUENCE: 39

```
gaacctgaag tcacccagac tcccagccat caggtcacac agatgggaca ggaagtgatc      60
ttgcgctgtg tccccatctc taatcactta tacttctatt ggtacagaca aatcttgggg     120
cagaaagtcg agtttctggt ttccttttat aataatgaaa tctcagagaa gtctgaaata     180
ttcgatgatc aattctcagt tgaaaggcct gatggatcaa atttcactct gaagatccgg     240
tccacaaagc tggaggactc agccatgtac ttctgtgcca gcagcctggg tgacaggggt     300
aatgaaaaac tgttttttgg cagtggaacc cagctctctg tcttgg                    346
```

<210> SEQ ID NO 40
<211> LENGTH: 114
<212> TYPE: PRT
<213> ORGANISM: Artificial Sequence
<220> FEATURE:
<223> OTHER INFORMATION: Synthetic

<400> SEQUENCE: 40

```
Glu Pro Glu Val Thr Gln Thr Pro Ser His Gln Val Thr Gln Met Gly
1               5                   10                  15
Gln Glu Val Ile Leu Arg Cys Val Pro Ile Ser Asn His Leu Tyr Phe
                20                  25                  30
Tyr Tyr Arg Gln Ile Leu Gly Gln Lys Val Glu Phe Leu Val Ser Phe
            35                  40                  45
Tyr Asn Asn Glu Ile Ser Glu Lys Ser Glu Ile Phe Asp Asp Gln Phe
        50                  55                  60
Ser Val Glu Arg Pro Asp Gly Ser Asn Phe Thr Leu Lys Ile Arg Ser
65                  70                  75                  80
Thr Lys Leu Glu Asp Ser Ala Met Tyr Phe Cys Ala Ser Ser Leu Gly
                85                  90                  95
Asp Arg Gly Asn Glu Lys Leu Phe Phe Gly Ser Gly Thr Gln Leu Ser
            100                 105                 110
Val Leu
```

<210> SEQ ID NO 41
<211> LENGTH: 331
<212> TYPE: DNA
<213> ORGANISM: Artificial Sequence
<220> FEATURE:
<223> OTHER INFORMATION: Synthetic

<400> SEQUENCE: 41

```
gatgctaaga ccacacagcc aaattcaatg gagagtaacg aagaagagcc tgttcacttg      60
ccttgtaacc actccacaat cagtggaact gattacatac attggtatcg acagcttccc     120
tcccagggtc agagtacgt gattcatggt cttacaagca atgtgaacaa cagaatggcc      180
tctctggcaa tcgctgaaga cagaaagtcc agtaccttga tcctgcaccg tgctaccttg     240
agagatgctg ctgtgtacta ctgcatcctg agacgtctta cgactacaa gctcagcttt      300
ggagccggaa ccacagtaac tgtaagagca a                                    331
```

<210> SEQ ID NO 42
<211> LENGTH: 110
<212> TYPE: PRT
<213> ORGANISM: Artificial Sequence
<220> FEATURE:
<223> OTHER INFORMATION: Synthetic

<400> SEQUENCE: 42

```
Asp Ala Lys Thr Thr Gln Pro Asn Ser Met Glu Ser Asn Glu Glu
1               5                   10                  15

Pro Val His Leu Pro Cys Asn His Ser Thr Ile Ser Gly Thr Asp Tyr
                20                  25                  30

Ile His Trp Tyr Arg Gln Leu Pro Ser Gln Gly Pro Glu Tyr Val Ile
            35                  40                  45

His Gly Leu Thr Ser Asn Val Asn Asn Arg Met Ala Ser Leu Ala Ile
        50                  55                  60

Ala Glu Asp Arg Lys Ser Ser Thr Leu Ile Leu His Arg Ala Thr Leu
65                  70                  75                  80

Arg Asp Ala Ala Val Tyr Tyr Cys Ile Leu Arg Arg Leu Asn Asp Tyr
                85                  90                  95

Lys Leu Ser Phe Gly Ala Gly Thr Thr Val Thr Val Arg Ala
            100                 105                 110
```

<210> SEQ ID NO 43
<211> LENGTH: 343
<212> TYPE: DNA
<213> ORGANISM: Artificial Sequence
<220> FEATURE:
<223> OTHER INFORMATION: Synthetic

<400> SEQUENCE: 43

```
gacgctggag tcacccaaag tcccacacac ctgatcaaaa cgagaggaca gcaagtgact      60
ctgagatgct ctcctaagtc tgggcatgac actgtgtcct ggtaccaaca ggccctgggt    120
caggggcccc agtttatctt tcagtattat gaggaggaag agacagag aggcaacttc     180 cctgatcgat tctcaggtca ccagttccct aactatagct ctgagctgaa tgtgaacgcc    240
ttgttgctgg gggactcggc cctctatctc tgtgccagca gcaaaggccc gggaggcaac    300
tacgagcagt acttcgggcc gggcaccagg ctcacggtca cag                       343
```

<210> SEQ ID NO 44
<211> LENGTH: 114
<212> TYPE: PRT
<213> ORGANISM: Artificial Sequence
<220> FEATURE:
<223> OTHER INFORMATION: Synthetic

<400> SEQUENCE: 44

```
Asp Ala Gly Val Thr Gln Ser Pro Thr His Leu Ile Lys Thr Arg Gly
1               5                   10                  15

Gln Gln Val Thr Leu Arg Cys Ser Pro Lys Ser Gly His Asp Thr Val
                20                  25                  30

Ser Trp Tyr Gln Gln Ala Leu Gly Gln Gly Pro Gln Phe Ile Phe Gln
            35                  40                  45

Tyr Tyr Glu Glu Glu Glu Arg Gln Arg Gly Asn Phe Pro Asp Arg Phe
        50                  55                  60

Ser Gly His Gln Phe Pro Asn Tyr Ser Ser Glu Leu Asn Val Asn Ala
65                  70                  75                  80

Leu Leu Leu Gly Asp Ser Ala Leu Tyr Leu Cys Ala Ser Ser Lys Gly
```

```
                    85                  90                  95
Pro Gly Gly Asn Tyr Glu Gln Tyr Phe Gly Pro Gly Thr Arg Leu Thr
                100                 105                 110

Val Thr

<210> SEQ ID NO 45
<211> LENGTH: 25
<212> TYPE: PRT
<213> ORGANISM: Artificial Sequence
<220> FEATURE:
<223> OTHER INFORMATION: Synthetic

<400> SEQUENCE: 45

Thr Ser Phe Leu Ser Ile Asn Ser Lys Glu Glu Thr Glu His Leu Glu
1               5                   10                  15

Asn Gly Asn Lys Tyr Pro Asn Leu Glu
            20                  25

<210> SEQ ID NO 46
<211> LENGTH: 25
<212> TYPE: PRT
<213> ORGANISM: Artificial Sequence
<220> FEATURE:
<223> OTHER INFORMATION: Synthetic

<400> SEQUENCE: 46

Arg Val Leu Lys Gly Gly Ser Val Arg Lys Leu Arg His Ala Lys Gln
1               5                   10                  15

Leu Val Leu Glu Leu Gly Glu Glu Ala
            20                  25

<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
tgttgactca acagccacag                                          20

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
ctggaccact tttctgaggg                                          20

<210> SEQ ID NO 49
<211> LENGTH: 26
<212> TYPE: DNA
<213> ORGANISM: Artificial Sequence
<220> FEATURE:
<223> OTHER INFORMATION: Synthetic

<400> SEQUENCE: 49
gccacagcac tgtgctcttg aagtcc                                   26

<210> SEQ ID NO 50
<211> LENGTH: 24
<212> TYPE: DNA
```

```
<213> ORGANISM: Artificial Sequence
<220> FEATURE:
<223> OTHER INFORMATION: Synthetic

<400> SEQUENCE: 50
caggcagtat ctggagtcat tgag                                              24

<210> SEQ ID NO 51
<211> LENGTH: 25
<212> TYPE: DNA
<213> ORGANISM: Artificial Sequence
<220> FEATURE:
<223> OTHER INFORMATION: Synthetic

<400> SEQUENCE: 51
caccatggat acctggctcg tatgc                                             25

<210> SEQ ID NO 52
<211> LENGTH: 18
<212> TYPE: DNA
<213> ORGANISM: Artificial Sequence
<220> FEATURE:
<223> OTHER INFORMATION: Synthetic

<400> SEQUENCE: 52
attcacccac cagctcag                                                     18

<210> SEQ ID NO 53
<211> LENGTH: 15
<212> TYPE: PRT
<213> ORGANISM: Artificial Sequence
<220> FEATURE:
<223> OTHER INFORMATION: Synthetic

<400> SEQUENCE: 53

Glu Thr Gly His Leu Glu Asn Gly Asn Lys Tyr Pro Asn Leu Glu
1               5                   10                  15

<210> SEQ ID NO 54
<211> LENGTH: 9
<212> TYPE: PRT
<213> ORGANISM: Artificial Sequence
<220> FEATURE:
<223> OTHER INFORMATION: Synthetic

<400> SEQUENCE: 54

Ala Ala Gly Ile Gly Ile Leu Thr Val
1               5

<210> SEQ ID NO 55
<211> LENGTH: 10
<212> TYPE: PRT
<213> ORGANISM: Artificial Sequence
<220> FEATURE:
<223> OTHER INFORMATION: Synthetic

<400> SEQUENCE: 55

Arg Leu Phe Pro Gly Leu Thr Ile Lys Ile
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Synthetic
```

```
<400> SEQUENCE: 56

Thr Arg Ser Ser Gly Ser His Phe Val Phe
1               5                   10

<210> SEQ ID NO 57
<211> LENGTH: 25
<212> TYPE: PRT
<213> ORGANISM: Artificial Sequence
<220> FEATURE:
<223> OTHER INFORMATION: Synthetic

<400> SEQUENCE: 57

Asp Ser Ser Leu Gln Ala Arg Leu Phe Pro Gly Leu Thr Ile Lys Ile
1               5                   10                  15

Gln Arg Ser Asn Gly Leu Ile His Ser
            20                  25

<210> SEQ ID NO 58
<211> LENGTH: 10
<212> TYPE: PRT
<213> ORGANISM: Artificial Sequence
<220> FEATURE:
<223> OTHER INFORMATION: Synthetic

<400> SEQUENCE: 58

Arg Leu Phe Pro Gly Leu Ala Ile Lys Ile
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic

<400> SEQUENCE: 59

Arg Leu Phe Pro Gly Leu Thr Ile Lys Ile
1               5                   10

<210> SEQ ID NO 60
<211> LENGTH: 8
<212> TYPE: PRT
<213> ORGANISM: Artificial Sequence
<220> FEATURE:
<223> OTHER INFORMATION: Synthetic

<400> SEQUENCE: 60

Arg Leu Phe Pro Gly Leu Thr Ile
1               5

<210> SEQ ID NO 61
<211> LENGTH: 11
<212> TYPE: PRT
<213> ORGANISM: Artificial Sequence
<220> FEATURE:
<223> OTHER INFORMATION: Synthetic

<400> SEQUENCE: 61

Leu Thr Ile Lys Ile Gln Arg Ser Asn Gly Leu
1               5                   10

<210> SEQ ID NO 62
<211> LENGTH: 11
<212> TYPE: PRT
<213> ORGANISM: Artificial Sequence
<220> FEATURE:
```

<223> OTHER INFORMATION: Synthetic

<400> SEQUENCE: 62

Leu Gln Ala Arg Leu Phe Pro Gly Leu Thr Ile
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic

<400> SEQUENCE: 63

Leu Gln Ala Arg Leu Phe Pro Gly Leu Thr
1               5                   10

<210> SEQ ID NO 64
<211> LENGTH: 25
<212> TYPE: PRT
<213> ORGANISM: Artificial Sequence
<220> FEATURE:
<223> OTHER INFORMATION: Synthetic

<400> SEQUENCE: 64

Thr Ile Ile Glu Gly Thr Arg Ser Ser Gly Ser His Phe Val Phe Val
1               5                   10                  15

Pro Ser Leu Arg Asp Val His His Glu
            20                  25

<210> SEQ ID NO 65
<211> LENGTH: 25
<212> TYPE: PRT
<213> ORGANISM: Artificial Sequence
<220> FEATURE:
<223> OTHER INFORMATION: Synthetic

<400> SEQUENCE: 65

Asp Ser Ser Leu Gln Ala Arg Leu Phe Pro Gly Leu Ala Ile Lys Ile
1               5                   10                  15

Gln Arg Ser Asn Gly Leu Ile His Ser
            20                  25

<210> SEQ ID NO 66
<211> LENGTH: 25
<212> TYPE: PRT
<213> ORGANISM: Artificial Sequence
<220> FEATURE:
<223> OTHER INFORMATION: Synthetic

<400> SEQUENCE: 66

Thr Ile Ile Glu Gly Thr Arg Ser Ser Gly Ser His Leu Val Phe Val
1               5                   10                  15

Pro Ser Leu Arg Asp Val His His Glu
            20                  25

<210> SEQ ID NO 67
<211> LENGTH: 10
<212> TYPE: PRT
<213> ORGANISM: Artificial Sequence
<220> FEATURE:
<223> OTHER INFORMATION: Synthetic

<400> SEQUENCE: 67

Thr Arg Ser Ser Gly Ser His Leu Val Phe

```
<210> SEQ ID NO 68
<211> LENGTH: 10
<212> TYPE: PRT
<213> ORGANISM: Artificial Sequence
<220> FEATURE:
<223> OTHER INFORMATION: Synthetic

<400> SEQUENCE: 68

Thr Arg Ser Ser Gly Ser His Phe Val Phe
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Synthetic

<400> SEQUENCE: 69

Thr Arg Ser Ser Gly Ser His Phe Val Phe Val
1               5                   10

<210> SEQ ID NO 70
<211> LENGTH: 9
<212> TYPE: PRT
<213> ORGANISM: Artificial Sequence
<220> FEATURE:
<223> OTHER INFORMATION: Synthetic

<400> SEQUENCE: 70

Thr Arg Ser Ser Gly Ser His Phe Val
1               5

<210> SEQ ID NO 71
<211> LENGTH: 8
<212> TYPE: PRT
<213> ORGANISM: Artificial Sequence
<220> FEATURE:
<223> OTHER INFORMATION: Synthetic

<400> SEQUENCE: 71

Thr Arg Ser Ser Gly Ser His Phe
1               5

<210> SEQ ID NO 72
<211> LENGTH: 10
<212> TYPE: PRT
<213> ORGANISM: Artificial Sequence
<220> FEATURE:
<223> OTHER INFORMATION: Synthetic

<400> SEQUENCE: 72

Phe Val Phe Val Pro Ser Leu Arg Asp Val
1               5                   10

<210> SEQ ID NO 73
<211> LENGTH: 25
<212> TYPE: PRT
<213> ORGANISM: Artificial Sequence
<220> FEATURE:
<223> OTHER INFORMATION: Synthetic

<400> SEQUENCE: 73

Thr Ser Phe Leu Ser Ile Asn Ser Lys Glu Glu Thr Gly His Leu Glu
1               5                   10                  15
```

```
Asn Gly Asn Lys Tyr Pro Asn Leu Glu
            20                  25
```